United States Patent
Butlin et al.

(10) Patent No.: US 9,273,059 B2
(45) Date of Patent: Mar. 1, 2016

(54) MACROCYCLIC HOPO CHELATORS

(75) Inventors: Nathaniel G. Butlin, Pacifica, CA (US); Kenneth N. Raymond, Berkeley, CA (US); Jide Xu, Richmond, CA (US); Anthony D'Aleo, Berkeley, CA (US)

(73) Assignee: LUMIPHORE, INC., Berkeley, CA (US)

(*) Notice: Subject to any disclaimer, the term of this patent is extended or adjusted under 35 U.S.C. 154(b) by 529 days.

(21) Appl. No.: 13/392,506

(22) PCT Filed: Aug. 24, 2010

(86) PCT No.: PCT/US2010/046517
§ 371 (c)(1),
(2), (4) Date: May 7, 2012

(87) PCT Pub. No.: WO2011/025790
PCT Pub. Date: Mar. 3, 2011

(65) Prior Publication Data
US 2012/0214253 A1    Aug. 23, 2012

Related U.S. Application Data

(60) Provisional application No. 61/236,468, filed on Aug. 24, 2009.

(51) Int. Cl.
*G01N 21/76* (2006.01)
*C07D 487/18* (2006.01)
*C07D 498/22* (2006.01)
*G01N 33/533* (2006.01)

(52) U.S. Cl.
CPC ............ *C07D 487/18* (2013.01); *C07D 498/22* (2013.01); *G01N 33/533* (2013.01)

(58) Field of Classification Search
None
See application file for complete search history.

(56) References Cited

U.S. PATENT DOCUMENTS

| 2,977,332 A | 3/1961 | Zumstein |
| 4,181,654 A | 1/1980 | Weitl et al. |
| 4,309,305 A | 1/1982 | Weitl et al. |

(Continued)

FOREIGN PATENT DOCUMENTS

| CA | 2099542 A1 | 1/1994 |
| EP | 0578067 A1 | 1/1994 |

(Continued)

OTHER PUBLICATIONS

Aime et al., Determination of the Prototropic Exchange Rate at the Water Molecule Coordinated to an Anionic Paramagnetic GdIII Chelate. Eur. J. Inorg. Chem. 1998, 1998 (9): 1283-1289.

(Continued)

*Primary Examiner* — Robert Xu
(74) *Attorney, Agent, or Firm* — Morgan, Lewis & Bockius LLP; Jeffry S. Mann

(57) ABSTRACT

The present invention provides a novel class of macrocyclic compounds as well as complexes formed between a metal (e.g., lanthanide) ion and the compounds of the invention. Preferred complexes exhibit high stability as well as high quantum yields of lanthanide ion luminescence in aqueous media without the need for secondary activating agents. Preferred compounds comprise hydroxypyridinonyl moieties within their macrocyclic structure and are characterized by surprisingly low, non-specific binding to a variety of polypeptides such as antibodies and proteins as well as high kinetic stability.

31 Claims, 20 Drawing Sheets

(56) References Cited

U.S. PATENT DOCUMENTS

| | | | |
|---|---|---|---|
| 4,442,305 A | 4/1984 | Weitl et al. |
| 4,543,213 A | 9/1985 | Weitl et al. |
| 4,666,927 A | 5/1987 | Hider et al. |
| 4,698,431 A | 10/1987 | Raymond et al. |
| 4,748,184 A | 5/1988 | Stout et al. |
| 4,855,225 A | 8/1989 | Fung et al. |
| 4,868,103 A | 9/1989 | Stavrianopoulos et al. |
| 4,939,254 A | 7/1990 | McMurry et al. |
| 4,978,614 A | 12/1990 | Bronstein |
| 5,010,191 A | 4/1991 | Engelstad et al. |
| 5,047,519 A | 9/1991 | Hobbs, Jr. et al. |
| 5,049,280 A | 9/1991 | Raymond et al. |
| 5,252,462 A | 10/1993 | Drevin et al. |
| 5,435,990 A | 7/1995 | Cheng et al. |
| 5,470,896 A | 11/1995 | Wegmann et al. |
| 5,478,741 A | 12/1995 | Maret et al. |
| 5,482,698 A | 1/1996 | Griffiths |
| 5,601,800 A | 2/1997 | Katti et al. |
| 5,624,901 A | 4/1997 | Raymond et al. |
| 5,820,849 A | 10/1998 | Schmitt-Willich et al. |
| 5,892,029 A | 4/1999 | Raymond et al. |
| 5,989,823 A | 11/1999 | Jayasena et al. |
| 5,998,146 A | 12/1999 | Latva et al. |
| 6,221,476 B1 | 4/2001 | Bruening et al. |
| 6,406,297 B1 | 6/2002 | Raymond et al. |
| 6,515,113 B2 | 2/2003 | Raymond et al. |
| 6,846,915 B2 | 1/2005 | Raymond et al. |
| 6,864,103 B2 | 3/2005 | Raymond et al. |
| 7,018,850 B2 | 3/2006 | Raymond et al. |
| 7,404,912 B2 | 7/2008 | Raymond et al. |
| 7,442,558 B2 | 10/2008 | Raymond et al. |
| 7,718,781 B2 | 5/2010 | Raymond et al. |
| 7,794,691 B2 | 9/2010 | Morgenstern et al. |
| 8,173,800 B2 | 5/2012 | Raymond et al. |
| 8,507,199 B2 | 8/2013 | Butlin et al. |
| 8,551,453 B2 | 10/2013 | Raymond et al. |
| 8,557,601 B2 | 10/2013 | Raymond et al. |
| 8,729,258 B2 | 5/2014 | Raymond et al. |
| 2002/0128451 A1 | 9/2002 | Raymond et al. |
| 2002/0188111 A1 | 12/2002 | Raymond et al. |
| 2003/0027189 A1 | 2/2003 | Raymond et al. |
| 2003/0095922 A1 | 5/2003 | Raymond et al. |
| 2003/0199688 A1 | 10/2003 | Kriesel et al. |
| 2004/0028611 A1 | 2/2004 | Frangioni |
| 2004/0249586 A1 | 12/2004 | Boge et al. |
| 2005/0008570 A1 | 1/2005 | Raymond et al. |
| 2005/0058604 A1 | 3/2005 | Raymond et al. |
| 2006/0135842 A1 | 6/2006 | Larsen et al. |
| 2006/0228297 A1 | 10/2006 | Larsen et al. |
| 2006/0286567 A1 | 12/2006 | Raymond et al. |
| 2007/0134160 A1 | 6/2007 | Leif et al. |
| 2008/0213780 A1 | 9/2008 | Butlin et al. |
| 2008/0213917 A1 | 9/2008 | Raymond et al. |
| 2008/0293155 A1 | 11/2008 | Raymond et al. |
| 2009/0023928 A1 | 1/2009 | Raymond et al. |
| 2009/0036537 A1 | 2/2009 | Raymond et al. |
| 2010/0015725 A1 | 1/2010 | Raymond et al. |
| 2010/0151591 A1 | 6/2010 | Butlin et al. |
| 2010/0167289 A1 | 7/2010 | Butlin et al. |
| 2011/0189088 A1 | 8/2011 | Xu et al. |
| 2012/0190012 A1 | 7/2012 | Butlin et al. |
| 2012/0214253 A1 | 8/2012 | Butlin et al. |
| 2012/0214843 A1 | 8/2012 | Durbin-Heavey et al. |
| 2012/0329174 A1 | 12/2012 | Raymond et al. |
| 2014/0039169 A1 | 2/2014 | Raymond et al. |

FOREIGN PATENT DOCUMENTS

| | | | |
|---|---|---|---|
| EP | 2423201 A1 | 2/2012 | |
| JP | 2003-535812 A | 12/2003 | |
| WO | 89/11475 A1 | 11/1989 | |
| WO | 91/12530 A1 | 8/1991 | |
| WO | 92/11039 A1 | 7/1992 | |
| WO | 97/00245 A1 | 1/1997 | |
| WO | 97/45539 A1 | 12/1997 | |
| WO | 00/48990 A1 | 8/2000 | |
| WO | 00/48991 A1 | 8/2000 | |
| WO | 03/016923 A2 | 2/2003 | |
| WO | 2005/030711 A2 | 4/2005 | |
| WO | 2005/030727 A1 | 4/2005 | |
| WO | 2006/001835 A2 | 1/2006 | |
| WO | 2007/121453 A2 | 10/2007 | |
| WO | 2008/008797 A2 | 1/2008 | |
| WO | WO 2008/008797 | * 1/2008 | ............... C07F 5/00 |
| WO | 2008/063721 A2 | 5/2008 | |
| WO | WO 2008/063721 | * 5/2008 | ............ A61K 49/00 |
| WO | 2008/092120 A1 | 7/2008 | |
| WO | 2010/034931 A1 | 4/2010 | |
| WO | 2010/051544 A2 | 5/2010 | |
| WO | 2011/025790 A1 | 3/2011 | |
| WO | 2011/098611 A2 | 8/2011 | |
| WO | 2013/167754 A1 | 11/2013 | |
| WO | 2013/167755 A1 | 11/2013 | |
| WO | 2013/167756 A1 | 11/2013 | |

OTHER PUBLICATIONS

Aime et al., Paramagnetic GdIII FeIII heterobimetallic complexes of DTPA-bis-salicylamide. Spectrochim. Acta A 1993, 49 (9), 1315-1322.

Alaverdian et al., A family of novel DNA sequencing instruments based on single-photon detection. Electrophoresis 2002, 23 (16): 2804-2817.

Allicotti et al., A time-resolved fluorescence immunoassay (DELFIA) increases the sensitivity of antigen-driven cytokine detection. J. Immunoassay Immunochem. 2003, 24 (4), 345-358.

Alpha et al., Luminescence Probes: The Eu3⊕- and Tb3⊕-Cryptates of Polypyridine Macrobicyclic Ligands. Angew. Chem. Int. Ed. Engl. 1987, 26 (12), 1266-1267.

Anderson and Welch, Radiometal-Labeled Agents (Non-Technetium) for Diagnostic Imaging. Chem. Rev. 1999, 99 (9), 2219-2234.

Arnaud et al., Synthesis of macrocyclic polyhydroxy tetralactams derived from L-tartaric acid and β-hydroxyglutaric acid. Tetrahedron 1997, 53 (40), 13757-13768.

Bai et al., Photocleavage of a 2-nitrobenzyl linker bridging a fluorophore to the 5' end of DNA. Proc. Natl. Acad. Sci. U.S.A. 2003, 100 (2), 409-413.

Bailly and Burgada, Nouvelle methode de synthese du 3,4,3 LI 1,2 HOPO (1,5,10,14-tetra(1-hydroxy-2-pyridone-6 oyl) 1,5,10,14 tetraazatetradecane). C. R. Acad. Sci., Ser. IIc: Chim. 1998, 1 (4), 241-245.

Batard et al., Use of Phycoerythrin and Allophycocyanin for Fluorescence Resonance Energy Transfer Analyzed by Flow Cytometry: Advantages and Limitations. Cytometry 2002, 48 (2), 97-105.

Beeby et al., Luminescence imaging microscopy and lifetime mapping using kinetically stable lanthanide(III) complexes. J. Photochem. Photobiol. B 2000, 57 (2-3), 83-89.

Bergeron and Navratil, Catecholamide Chelators for Actinide Environmental and Human Decontamination. Chem. Abstr. 1986, 105, 221872z.

Blomberg et al., Terbium and rhodamine as labels in a homogeneous time-resolved fluorometric energy transfer assay of the beta subunit of human chorionic gonadotropin in serum. Clin Chem 1999, 45 (6 Pt 1), 855-861.

Bodanszky and Bodanszky, Activation and Coupling [excerpt]. In The Practice of Peptide Synthesis, 2nd ed.; Springer-Verlag Berlin Heidelberg, 1984; pp. 96-125.

Boswell and Brechbiel, Development of radioimmunotherapeutic and diagnostic antibodies: an inside-out view. Nucl. Med. Biol. 2007, 34 (7), 757-778.

Brooker et al., Figure-of-eight Shaped Metal-free Amide-containing Schiff-base Macrocycles and Two Dicobalt(III) Amide Complexes. Chemical Abstracts 2002, HCAplus Accession No. 2002:593344.

Bruchez et al., Semiconductor Nanocrystals as Fluorescent Biological Labels. Science 1998, 281 (5385), 2013-2016.

Brumley and Smith, Rapid DNA sequencing by horizontal ultrathin gel electrophoresis. Nucleic Acids Res. 1991, 19 (15), 4121-4126.

(56) References Cited

OTHER PUBLICATIONS

Brunet et al., Lanthanide complexes of polycarboxylate-bearing dipyrazolylpyridine ligands with near-unity luminescence quantum yields: the effect of pyridine substitution. Photochem. Photobiol. Sci. 2002, 1 (8), 613-618.
Bryant et al., Synthesis and relaxometry of high-generation {G=5, 7, 9, and 10} PAMAM dendrimer-DOTA-gadolinium chelates. J. Magn. Reson. Imaging 1999, 9 (2), 348-352.
Budimir et al., Study of metal complexes of a tripodal hydroxypyridinone ligand by electrospray tandem mass spectrometry, Rapid Commun. Mass Spectrom. 2005, 19 (13), 1822-1828.
Bulman et al., An examination of some complexing agents for ability to remove intracellularly deposited plutonium. Chem. Abstr. 1980, 92, 106582f.
Bunzli et al., Towards materials with planned properties: dinuclear f-f helicates and d-f nonconvalent podates based on benzimidazole-pyridine binding units. J. Alloys Compd. 1997, 249 (1-2), 14-24.
Burgada et al., Synthesis of 3,4,3 LI 1,2 HOPO labelled with 14C. J. Label. Compd. Radiopharm. 2001, 44 (1), 13-19.
Cardullo et al., Detection of nucleic acid hybridization by nonradiative fluorescence resonance energy transfer. Proc. Natl. Acad. Sci. USA 1988, 85 (23), 8790-8794.
Chan and Nie, Quantum Dot Bioconjugates for Ultrasensitive Nonisotopic Detection. Science 1998, 281 (5385), 2016-2018.
Chen and Selvin, Lifetime- and color-tailored fluorophores in the micro- to millisecond time regime. J. Am. Chem. Soc. 2000, 122 (4), 657-660.
Chen and Selvin, Thiol-reactive luminescent chelates of terbium and europium. Bioconjug. Chem. 1999, 10 (2), 311-315.
Choudhary et al., New compounds of tetradentate Schiff bases with vanadium (IV) and vanadium (V). J. Chem. Soc., Dalton Trans. 1999, 24, 4437-4446.
Clarke et al., Crystal structure of the tris 1,2-dimethyl-3-hydroxy-4-pyridinone (DMHP) complex with the Fe(III) ion. Inorg. Chim. Acta 1992, 196 (2), 177-183.
Cohen et al., A Novel Salicylate-Based Macrobicycle with a "Split Personality". Inorg. Chem. 1999, 38 (20), 4522-4529.
Cohen et al., Syntheses and relaxation properties of mixed gadolinium hydroxypyridinonate MRI contrast agents. Inorg. Chem. 2000, 39 (25), 5747-5756.
Collins et al., A vision for the future of genomics research. Nature 2003, 422 (6934), 835-847.
Comby et al., Stable 8-hydroxyquinolinate-based podates as efficient sensitizers of lanthanide near-infrared luminescence. Inorg. Chem. 2006, 45 (2), 732-743.
Curtet, C., In Vivo diagnosis and therapy of human tumors with monoclonal antibodies. Int. J. Radiat. Appl. Instrum., Part B, 1989, 16 (2), 180.
Dahlen, P., Detection of Biotinylated DNA Probes by Using Eu-Labeled Streptavidin and Time-Resolved Fluorometry. Anal. Biochem. 1987, 164 (1), 78-83.
de Sa et al., Spectroscopic properties and design of highly luminescent lanthanide coordination complexes. Coord. Chem. Rev. 2000, 196 (1), 165-195.
Demas and Crosby, Measurement of Photoluminescence Quantum Yields. A Review. J. Phys. Chem. 1971, 75 (8), 991-1024.
Dexter, D.L., A Theory of Sensitized Luminescence in Solids. J. Chem. Phys. 1953, 21 (5), 836-850.
Dickins et al., Synthesis, time-resolved luminescence, NMR spectroscopy, circular dichroism and circularly polarised luminescence studies of enantiopure macrocyclic lanthanide tetraamide complexes. Chem. Eur. J. 1999, 5 (3), 1095-1105.
Dickson et al., Time-resolved detection of lanthanide luminescence for ultrasensitive bioanalytical assays. J. Photochem. Photobiol. B. 1995, 27 (1), 3-19.
Doble et al., Toward optimized high-relaxivity MRI agents: the effect of ligand basicity on the thermodynamic stability of hexadentate hydroxypyridonate/catecholate gadolinium(III) complexes. Inorg. Chem. 2003, 42 (16), 4930-4937.

Durbin et al., In vivo chelation of Am(III), Pu(IV), Np(V) and U(VI) in mice by TREN-(Me-3,2-HOPO). Chem. Abstr. 1995, 122, 4449p.
Durbin et al., Specific sequestering agents for the actinides: 10. Enhancement of plutonium-238 elimination from mice by poly(catechoylamide) ligands. Chem. Abstr. 1984, 101, 125980e.
Eid et al., Real-Time DNA Sequencing from Single Polymerase Molecules. Science 2009, 323 (5910), 133-138.
Edelstein et al. Optical properties of Cm(III) in crystals and solutions and their application to Cm(III) speciation. Coord. Chem. Rev. 250, 2006, 948-973.
Farkas et al., Equilibrium studies on copper(II)- and iron(III)-monohydroxamates. Polyhedron 1998, 17 (19), 3331-3342.
Förster, T., Transfer Mechanisms of Electronic Excitation. Discuss. Faraday Soc. 1959, 27, 7-17.
Förster, T., Zwischenmolekulare Energiewanderung und Fluoreszenz. Ann. Phys. 1948, 437 (1-2), 55-75.
Frank et al., Detection of pulmonary emboli by using MR angiography with MPEG-PL-GdDTPA: an experimental study in rabbits. AJR Am. J. Roentgenol. 1994, 162 (5), 1041-1046.
Galaup et al., Mono(di)nuclear eropium(III) complexes of macrobi(tri)cyclic cryptands derived from diazatetralactams as luminophores in aqueous solution. Helv. Chim. Acta. 1999, 82 (4), 543-560.
Glazer, A. N., Light Harvesting by Phycobilisomes. Annu. Rev. Biophys. Biophys. Chem. 1985, 14, 47-77.
Gong, B., Crescent oligoamides: From acyclic "Macrocycles" to folding nanotubes. Chem Eur J 2001, 7 (20), 4336-4342.
Hajela et al., A tris-hydroxymethyl-substituted derivative of Gd-TREN-Me-3,2-HOPO: An MRI relaxation agent with improved efficiency. J. Am. Chem. Soc. 2000, 122 (45), 11228-11229.
Hajela et al., Synthesis of homochiral tris(2-alkyl-2-aminoethyl) amine derivatives from chiral a-amino aldehydes and their application in the synthesis of water soluble chelators. Inorg. Chem. 2001, 40 (13), 3208-3216.
Heid et al., Real time quantitative PCR. Genome Res. 1996, 6 (10), 986-994.
Hemmila et al., Development of luminescent lanthanide chelate labels for diagnostic assays. J. Alloys Compd. 1997, 249 (1-2), 158-162.
Hemmilä et al., Europium as a label in time-resolved immunofluorometric assays. Anal. Biochem. 1984, 137 (2), 335-343.
Hemmila, I. A. In Immunochemistry 1; Johnstone, A. P., Turner, M. W., Eds.; IRL Press: Oxford, U.K., 1997; pp. 193-214.
Hemmilä, I., LANCE™: Homogeneous Assay Platform for HTS. J. Biomol. Screening 1999, 4 (6), 303-307.
Hemmilä, I., Luminescent lanthanide chelates—a way to more sensitive diagnostic methods. J. Alloys Compd. 1995, 225 (1-2), 480-485.
Higuchi. et al., Simultaneous Amplification and Detection of Specific DNA Sequences. Biotechnology (NY) 1992, 10 (4), 413-417.
Hochstrasser et al., Distance distribution in a dye-linked oligonucleotide determined by time-resolved fluorescence energy transfer. Biophys. Chem. 1992, 45 (2), 133-141.
Holland et al., Detection of specific polymerase chain reaction product by utilizing the 5'.fwdarw. 3'exonuclease activity of Thermus aquaticus DNA polymerase. Proc. Nat. Acad. Sci. USA 1991, 88 (16), 7276-7280.
Jaakkola et al., Solid-phase synthesis of oligonucleotides labeled with luminescent lanthanide(III) chelates. Bioconjug. Chem. 2005, 16 (3), 700-709.
Jagannathan and Soundararajan, "Complexes of lanthanide perchlorated with N,N,N'n'-tetra-amethyl-α-carboxamido-o-anisamide and N, N'-di-t-butyl-α-carboxamido-o-anisamide" Inorganica Chim. Acta 1979, 37, L449-L451.
Johansson et al., Time Gating Improves Sensitivity in Energy Transfer Assays with Terbium Chelate/Dark Quencher Oligonucleotide Probes. J. Am. Chem. Soc. 2004, 126 (50), 16451-16455.
Johnson et al., Synthesis of a ligand based upon a new entry into the 3-hydroxy-N-alkyl-2(1H0-pyridinone ring system and thermodynamic evaluation of its gadolinium complex. Inorg. Chem. 2000, 39 (12), 2652-2660.

(56) References Cited

OTHER PUBLICATIONS

Ju et al., Fluorescence energy transfer dye-labeled primers for DNA sequencing and analysis. Proc. Natl. Acad. Sci. U.S.A. 1995, 92 (10), 4347-4351.

Karpishin et al., Stereoselectivity in chiral iron(III) and gallium(III) tris(catecholate) complexes effected by nonbonded weakly polar interactions. J. Am. Chem. Soc. 1993, 115 (14), 6115-6125.

Kelly and Lang, Total Synthesis of Dimethyl Sulfomycinamate. J. Org. Chem. 1996, 61 (14), 4623-4633.

Kheterpal et al., DNA sequencing using a four-color confocal fluorescence capillary array scanner. Electrophoresis 1996, 17 (12): 1852-1859.

Kling, J., Ultrafast DNA sequencing. Nat. Biotechnol. 2003, 21 (12), 1425-1427.

Knight, C.G., Fluorimetric Assays of Proteolytic Enzymes. Methods Enzymol. 1995, 248: 18-34.

Kostrikis et al., Spectral Genotyping of Human Alleles. Science 1998, 279 (5354), 1228-1229.

Kulmala et al, Electrochemiluminescent labels for applications in fully aqueous solutions at oxide-covered aluminium electrodes. Anal. Chim. Acta 1999, 386 (1-2), 1-6.

Kunkely and Vogler, Photoluminescence of thorium(IV) 2-methyl-8-quinolinolate. Chem. Phys. Lett. 304, 1999, 187-190.

Lassiter et al., Time-resolved fluorescence imaging of slab gels for lifetime base-calling in DNA sequencing applications. Anal. Chem. 2000, 72 (21), 5373-5382.

Lee et al., Allelic discrimination by nick-translation PCR with fluorogenic probes. Nucleic Acids Res. 1993, 21 (16), 3761-3766.

Lee et al., New energy transfer dyes for DNA sequencing. Nucleic Acids Res. 1997, 25 (14), 2816-2822.

Lee et al., Seven-Color, Homogeneous Detection of Six PCR Products. Biotechniques 1999, 27 (2), 342-349.

Li et al., A photocleavable fluorescent nucleotide for DNA sequencing and analysis. Proc. Natl. Acad. Sci. U.S.A. 2003, 100 (2), 414-419.

Li et al., Shape-persistent aromatic amide oligomers: new tools for supramolecular chemistry, Chem. Asian J. 2006, 1 (6), 766-778.

Lichtenberger and Geyer, Cyanoethylation. II. Substituted β-phenoxypropionic acids. Bull. Soc. Chim. Fr. 1963, 275-282.

Lieberwirth et al., Multiplex dye DNA sequencing in capillary gel electrophoresis by diode laser-based time-resolved fluorescence detection. Anal. Chem. 1998, 70 (22), 4771-4779.

Margulies et al., Genome sequencing in microfabricated high-density picolitre reactors. Nature 2005, 437 (7057), 376-380.

Mathis, G., HTRF® Technology. J. Biomol. Screen. 1999, 4 (6), 309-314.

Mathis, G., Rare earth cryptates and homogeneous fluoroimmunoassays with human sera. Clin. Chem. 1993, 39 (9), 1953-1959.

Mattoussi et al., Self-Assembly of CdSe—ZnS Quantum Dot Bioconjugates Using an Engineered Recombinant Protein. J. Am. Chem. Soc. 2000, 122 (49), 12142-12150.

Metzker et al., Electrophoretically uniform fluorescent dyes for automated DNA sequencing. Science 1996, 271 (5254), 1420-1422.

Metzker, M. L., Emerging technologies in DNA sequencing. Genome Res. 2005, 15 (12), 1767-1776.

Mikola et al., Syntheses and properties of luminescent lanthanide chelate labels and labeled haptenic antigens for homogeneous immunoassays. Bioconjug. Chem. 1995, 6 (3), 235-241.

Momany et al. Crystal structure of dimeric HIV-1 capsid protein. Nat. Struct. Biol. 1996, 3 (9), 763-770.

Moore et al., "Cymothoe sangaris": An Extremely Stable and Highly Luminescent 1,2-Hydroxypyridinonate Chelate of Eu(III). J. Am. Chem. Soc. 2006, 128 (33), 10648-10649.

Moore et al., An octadentate luminescent Eu(III) 1,2-HOPO chelate with potent aqueous stability. Inorg. Chem. 2007, 46 (14), 5468-5470.

Moore et al., Eu (III) Complexes of Functionalized Octadentate 1-Hydroxypyridin-2-ones: Stability, Bioconjugation, and Luminescence Resonance Energy Transfer Studies. Inorg. Chem. 2010, 49, 9928-9939.

Moyer et al. Enhanced liquid-liquid anion exchange using macrocyclic anion receptors: effect of receptor structure on sulphate—nitrate exchange selectivity. Supra Molecular Chemistry. 2010 vol. 22, pp. 653-671.

Mugabe et al., Liposome-mediated gentamicin delivery: development and activity against resistant strains of Pseudomonas aeruginosa isolated from cystic fibrosis patients. J. Antimicrob. Chemother. 2005, 55 (2), 269-271.

Nazarenko et al., A closed tube format for amplification and detection of DNA based on energy transfer. Nucleic Acids Res. 1997, 25 (12), 2516-2521.

Nunnally et al., Characterization of visible dyes for four-decay fluorescence detection in DNA sequencing. Anal. Chem. 1997, 69 (13), 2392-2397.

Okawa et al., Binuclear metal complexes. V. Template synthesis of a binuclear copper(II) complex of a macrocycle containing amino groups. Chem. Lett. 1972, 10, 1027-1030.

Ost, H., Synthese mehrbasischer Säuren aus Salicylsäure and Kohlensäure. J. Prakt. Chem. 1876, 14 (1), 93-124.

Petoud et al., Stable Lanthanide Luminescence Agents Highly Emissive in Aqueous Solution: Multidentate 2-Hydroxyisophthalamide Complexes of Sm3+, Eu3+, Tb3+, Dy3+. J. Am. Chem. Soc. 2003, 125 (44), 13324-13325.

Pierre et al., Substituent effects on Gd(III)-based MRI contrast agents: optimizing the stability and selectivity of the complex and the number of coordinated water molecules. Inorg. Chem. 2006, 45 (20), 8355-8364.

Poole et al., Synthesis and characterisation of highly emissive and kinetically stable lanthanide complexes suitable for usage "in cellulo". Org. Biomol. Chem. 2005, 3 (6), 1013-1024.

Prober et al., A System for Rapid DNA Sequencing with Fluorescent Chain-Terminating Dideoxynucleotides. Science 1987, 238 (4825), 336-341.

Puerta et al., Tris(pyrone) Chelates of Gd(III) as High Solubility MRI-CA. J. Am. Chem. Soc. 2006, 128 (7), 2222-2223.

Rajapakse et al., Luminescent Terbium Protein Labels for Time-Resolved Microscopy and Screening. Angew. Chem. Int. Ed. Engl. 2009, 48 (27), 4990-4992.

Raymond and Pierre, Next Generation, High Relaxivity Gadolinium MRI Agents. Bioconjug. Chem. 2005, 16 (1), 3-8.

Riehl and Richardson, Circularly Polarized Luminescence Spectroscopy. Chem. Rev. 1986, 86 (1), 1-16.

Ruparel et al., Design and synthesis of a 3'-O-allyl photocleavable fluorescent nucleotide as a reversible terminator for DNA sequencing by synthesis. Proc. Natl. Acad. Sci. U.S.A. 2005, 102 (17), 5932-5937.

Sabbatini et al., Luminescent lanthanide complexes as photochemical supramolecular devices. Coord. Chem. Rev. 1993, 123 (1), 201-228.

Saha et al., Time-resolved fluorescence new europium chelate complex: Demonstration of highly sensitive detection of protein and DNA samples. J. Am. Chem. Soc. 1993, 115 (23), 11032-11033.

Scarrow et al., Ferric ion sequestering agents. 14. 1-Hydroxy-2(1H)-pyridinone complexes: properties and structure of a novel iron—iron dimer. J. Am. Chem. Soc. 1985, 107 (23), 6540-6546.

Schoket et al., Increased sensitivity for determination of polycyclic aromatic hydrocarbon-DNA adducts in human DNA samples by dissociation-enhanced lanthanide fluoroimmunoassay (DELFIA). Cancer Epidemiol. Biomarkers Prev. 1993, 2 (4), 349-353.

Selvin, P. R., Principles and biophysical applications of lanthanide-based probes. Annu. Rev. Biophys. Biomol. Struct. 2002, 31, 275-302.

Selvin, P., Fluorescence Resonance Energy Transfer. Methods Enzymol. 1995, 246, 300-334.

Seo et al., Four-color DNA sequencing by synthesis on a chip using photocleavable fluorescent nucleotides. Proc. Natl. Acad. Sci. U.S.A. 2005. 102 (17), 5926-5931.

Sequoia, E., Complexes of Lanthanide Perchlorates. Inorganica Chim. Acta 1979, 37 (1), L449-L451.

Smith et al., Fluorescence detection in automated DNA sequence analysis. Nature 1986, 321 (6071), 674-679.

(56) References Cited

OTHER PUBLICATIONS

Soini et al., Time-resolved fluorescence of lanthanide probes and applications in biotechnology. CRC Crit. Rev. Anal. Chem. 1987, 18 (2), 105-154.
Soulere et al., Selective Inhibition of Fe-versus Cu/Zn-Superoxide Dismutases by 2,3-Dihydrosybenzoic Acid Derivavtives. Chem. Pharm. Bull. (Tokyo) 2002, 50 (5), 578-582.
Southwood-Jones et al. Oxygen-17 NMR and EPR studies of water exchange from the first coordination sphere of gadolinium(III) aquoion and gadolinium(III) propylenediaminetetra-acetate. J. Chem. Phys. 1980, 73 (12), 5909-5918.
Stack et al. Rational reduction of the conformational space of a siderophore analog through nonbonded interactions: the role of entropy in enterobactin. J. Am. Chem. Soc. 1993, 115 (14), 6466-6467.
Steemers et al. Water-soluble neutral calix[4]arene-lanthanide complexes: Synthesis and luminescence properties. J. Org. Chem. 1997, 62 (13), 4229-4235.
Steinberg, I., Long-Range Nonradiative Transfer of Electronic Excitation Energy in Proteins and Polypeptides. Annu. Rev. Biochem. 1971, 40, 83-114.
Stenroos et al., Homogeneous time-resolved IL-21L-R.alpha. assay using fluorescence resonance energy transfer. Cytokine 1998, 10 (7), 495-499.
Streater et al., Novel 3-hydroxy-2(1H)-pyridinones. Synthesis, Iron(III)-Chelating Properties, and Biological Activity. J. Med. Chem. 1990, 33 (6), 1749-1755.
Stryer, L., Fluorescence Energy Transfer as a Spectroscopic Ruler. Ann. Rev. Biochem. 1978, 47, 819-846.
Sunderland et al., 6-Carboxamido-5, 4-Hydroxypyrimidinones: A New Class of Heterocyclic Ligands and Their Evaluation as Gadolinium Chelating Agents. Inorg. Chem. 2001, 40 (26), 6746-6756.
Syvanen et al., Time-resolved fluorometry: a sensitive method to quantify DNA-hybrids. Nucleic Acids Res. 1986, 14 (2), 1017-1028.
Takalo et al., Synthesis of europium(III) chelates suitable for labeling of bioactive molecules Bioconjug. Chem. 1994, 5 (3), 278-282.
Tedeschi et al. A solid-state study of eight-coordinate lanthanide(III) complexes (Ln=Eu, Gd, Tb, Dy) with 1-hydroxy-2-pyridinone. Dalton Trans. 2003, 9, 1738-1745.
Tsien, R. Y., The Green Fluorescent Protein. Annu. Rev. Biochem. 1998, 67, 509-544.
Tyagi et al., Molecular Beacons: Probes that Fluoresce upon Hybridization. Nat. Biotechnol 1996, 14 (3), 303-308.
Tyagi et al., Multicolor molecular beacons for allele discrimination. Nat. Biotechnol. 1998, 16 (1), 49-53.
Uhlir et al., Specific Agents for the Actinides. 21. Synthesis and Initial Biological Testing of Octadentate Mixed Catecholate-Hydroxypridinoate Ligands. J. Med. Chem. 1993, 36 (4), 504-509.
Uhlir, L. C., Mixed Functionality Actinide Sequestering Agents. Ph.D. Thesis, University of California, Berkeley, CA, 1992.
Ullman et al., Fluorescent excitation transfer immunoassay. A general method for determination of antigens. J. Biol. Chem. 1976, 251 (14), 4172-4178.
Unger et al., Gadolinium-containing copolymeric chelates—a new potential MR contrast agent Magn. Reson. Mater. Phys., Biol. Med. 1999, 8 (3), 154-162.
Vander Elst et al., Stereospecific binding of MRI contrast agents to human serum albumin: the case of Gd—(S)-EOB-DTPA (Eovist) and its (R) isomer. J. Biol. Inorg. Chem. 2001, 6 (2), 196-200.
Veiopoulou et al., Comparative study of fluorescent ternary terbium complexes. Application in enzyme amplified fluorimetric immunoassay for .alpha.-fetoprotein. Anal. Chim. Acta 1996, 335 (1-2), 177-184.
Vereb et al., Temporally and Spectrally Resolved Imaging Microscopy of Lanthanide Chelates Biophys. J. 1998, 74 (5), 2210-2222.
Vicentini et al., Luminescence and structure of europium compounds. Coord. Chem. Rev. 2000, 196 (1), 353-382.
Villa et al., Force Field Parametrization for Gadolinium Complexes Based on ab Initio Potential Energy Surface Calculations. J. Phys. Chem. A 2000, 104 (15), 3421-3429.
Voss et al., Direct genomic fluorescent on-line sequencing and analysis using in vivo amplification of DNA. Nucleic Acids Res. 1989, 17 (7), 2517-2527.
Wagnon and Jackels, Synthesis, characterization, and aqueous proton relaxation enhancement of a manganese(II) heptaaza macrocyclic complex having pendant arms. Inorg. Chem. 1989, 28 (10), 1923-1927.
Wang et al., Design and Synthesis of New Fluorogenic HIV Protease Substrates Based on Resonance Energy Transfer. Tetrahedron Lett. 1990, 31 (45), 6493-6496.
Wang et al., Rapid Sizing of Short Tandem Repeat Alleles Using Capillary Array Electrophoresis and Energy-Transfer Fluorescent Primers. Anal. Chem. 1995, 67 (7), 1197-1203.
Wang et al., Unnatural Amino Acid Mutagenesis of Green Fluorescent Protein. J. Org. Chem. 2003, 68 (1), 174-176.
Weibel et al., Engineering of highly luminescent lanthanide tags suitable for protein labeling and time-resolved luminescence imaging. J. Am. Chem. Soc. 2004, 126 (15), 4888-4896.
Werner et al., Highly Soluble Tris-hydroxypyridonate Gd(III) Complexes with Increased Hydration Number, Fast Water Exchange, Slow Electronic Relaxation, and High Relaxivity. J. Am. Chem. Soc. 2007, 129 (7), 1870-1871.
Whitcombe et al., Detection of PCR products using self-probing amplicons and fluorescence. Nat. Biotechnol. 1999, 17 (8), 804-807.
White et al., Specific Sequestering Agents for the Actinides. 16. Synthesis and Initial Bioological Testing of Polydentate Oxohydroxypyridinecarboxylate Ligands. J. Med. Chem. 1988, 31 (1), 11-18.
Xiao and Selvin, Quantum yields of luminescent lanthanide chelates and far-red dyes measured by resonance energy transfer. J. Am. Chem. Soc. 2001, 123 (29), 7067-7073.
Xu et al., Gadolinium (III) 1,2-hydroxypyridonate-based complexes: toward MRI contrast agents of high relaxivity. Inorg. Chem. 2004, 43 (18), 5492-5494.
Xu et al., Gadolinium complex of tris[(3-hydroxy-1-methyl-2-oxo-1,2-didehydropyridine-4-carboxamido)ethyl]-amine: A new class of gadolinium magnetic resonance relaxation agents. J. Am. Chem. Soc. 1995, 117 (27), 7245-7246.
Xu et al., Gadolinium(III) 1,2-hydroxypyridonate-based complexes: toward MRI contrast agents of high relaxivity. Inorg. Chem. 2004, 43 (18), 5492-5494.
Xu et al., Plutonium(IV) Sequestration: Structural and Thermodynamic Evaluation of the Extraordinarily Stable Cerium(IV) Hydroxypyridinonate Complexes. Inorg. Chem. 2000, 39 (18), 4156-4164.
Xu et al., Specific Sequestering Agents for the Actinides. 28. Synthesis and Initial Evaluation of Multidentate 4-Carbamoyl-3-hydroxy-l-methyl-2-(1H)-pyridinone Ligands for in Vivo Plutonium (IV) Chelation. J. Med. Chem. 1995, 38 (14), 2606-2614.
Yamada et al., Selective Modification of Asparatic Acid-101 in Lysozyme by Carbodiimide Reaction. Biochemistry. 1981, 20, 4836-4842.
Yue et al., Potentiometric and spectrophotometric determination of stabilities of the 1-hydroxy-2-pyridinone complexes of trivalent and divalent metal ions. Inorg. Chim. Acta 1993, 214 (1-2), 103-111.

\* cited by examiner

FIG. 2

| Acceptor | Absorbance (nm) | Emission (nm) |
|---|---|---|
| Fluorescein (FITC) | 494 | 518 |
| Eosin | 524 | |
| TRITC | 543 | |
| Rhodamine 101 | 496 | 520 |
| Rhodamine Red | 570 | |
| Texas Red | 595 | 615 |
| Alexa 488 | 495 | 519 |
| Alexa 532 | 530 | |
| Alexa 546 | 555 | 573 |
| Cy2 | 489 | 506 |
| Cy3 | 548 | 562 |
| Cy5 | 649 | 670 |
| Malachite Green | 630 | |
| TAMRA | 555 | 580 |
| Acridine orange | 500 | 530 |
| Bodipy 530/550 | 534 | 554 |
| BODIPY TR-X | 588 | 616 |
| GFP | 489 | 509 |
| Nile Red | 485 | 525 |
| Oregon Green 488 | 493 | 520 |
| YOYO-1 | 491 | 509 |
| YOYO-2 | 612 | 631 |
| Ca-Green | 506 | 534 |
| Ca-Orange | 555 | 576 |
| Ca-Crimson | 588 | 610 |
| Mg-Green | 506 | 532 |
| Na-Green | 507 | 532 |

[Eu(L-1,2-HOPO)]°

[Eu(L-1,2-HOPO)]°

MACROCYCLIC HOPO CHELATORS

CROSS-REFERENCE TO RELATED APPLICATION

This application is a 371 national phase filing of PCT Application PCT/US2010/046517, filed Aug. 24, 2010, which claims, under 35 USC 119(e)(1), the benefit of U.S. Application 61/236,468, filed Aug. 24, 2009, which is hereby incorporated by reference in its entirety.

FIELD OF THE INVENTION

This invention relates to macrocyclic ligands and metallic complexes thereof. Exemplary ligands or complexes are bound to a carrier or a support through a linker.

BACKGROUND OF THE INVENTION

There is a continuous and expanding need for rapid, highly specific methods of detecting and quantifying chemical, biochemical and biological substances as analytes in research and diagnostic mixtures. Of particular value are methods for measuring small quantities of nucleic acids, peptides, pharmaceuticals, metabolites, microorganisms and other materials of diagnostic value. Examples of such materials include small molecular bioactive materials (e.g., narcotics and poisons, drugs administered for therapeutic purposes, hormones), pathogenic microorganisms and viruses, antibodies, and enzymes and nucleic acids, particularly those implicated in disease states.

The presence of a particular analyte can often be determined by binding methods that exploit the high degree of specificity, which characterizes many biochemical and biological systems. Frequently used methods are based on, for example, antigen-antibody systems, nucleic acid hybridization techniques, and protein-ligand systems. In these methods, the existence of a complex of diagnostic value is typically indicated by the presence or absence of an observable "label" which is attached to one or more of the interacting materials. The specific labeling method chosen often dictates the usefulness and versatility of a particular system for detecting an analyte of interest. Preferred labels are inexpensive, safe, and capable of being attached efficiently to a wide variety of chemical, biochemical, and biological materials without significantly altering the important binding characteristics of those materials.

A wide variety of labels are known, each with particular advantages and disadvantages. For example, radioactive labels are quite versatile, and can be detected at very low concentrations. Such labels are, however, expensive, hazardous, and their use requires sophisticated equipment and trained personnel. Thus, there is wide interest in non-radioactive labels, particularly labels observable by spectrophotometric, spin resonance, and luminescence techniques, and reactive materials, such as enzymes that produce such molecules.

Labels that are detectable using fluorescence spectroscopy are of particular interest, because of the large number of such labels that are known in the art. Moreover, the literature is replete with syntheses of fluorescent labels that are derivatized to allow their facile attachment to other molecules, and many such fluorescent labels are commercially available.

In addition to being directly detected, many fluorescent labels operate to quench the fluorescence of an adjacent second fluorescent label. Because of its dependence on the distance and the magnitude of the interaction between the quencher and the fluorophore, the quenching of a fluorescent species provides a sensitive probe of molecular conformation and binding, or other, interactions. An excellent example of the use of fluorescent reporter quencher pairs is found in the detection and analysis of nucleic acids.

Conventional organic fluorophores generally have short fluorescence lifetimes, on the order of nanoseconds (ns) which is generally too short for optimal discrimination from background fluorescence. An alternative detection scheme, which is theoretically more sensitive than conventional fluorescence, is time-resolved fluorimetry. According to this method, a chelated lanthanide metal with a long radiative lifetime is attached to a molecule of interest. Pulsed excitation combined with a gated detection system allows for effective discrimination against short-lived background emission. For example, using this approach, the detection and quantification of DNA hybrids via an europium-labeled antibody has been demonstrated (Syvanen et al., *Nucleic Acids Research* 14: 1017 1028 (1986)). In addition, biotinylated DNA was measured in microtiter wells using Eu-labeled strepavidin (Dahlen, *Anal. Biochem.* (1982), 164: 78 83). A disadvantage, however, of these types of assays is that the label must be washed from the probe and its fluorescence developed in an enhancement solution.

Lanthanide chelates, particularly coordinatively saturated chelates that exhibit excellent fluorescence properties are highly desirable. Alternatively, coordinatively unsaturated lanthanide chelates exhibiting acceptable fluorescence in the presence of water are also advantageous. Such chelates that are derivatized to allow their conjugation to one or more components of an assay, find use in a range of different assay formats.

The present invention provides these and other such compounds and assays using these compounds. Complexes of lanthanide ions such as $Tb^{3+}$ and $Eu^{3+}$ are potentially useful in a variety of biological applications. Of particular importance for biological applications is that these complexes exhibit kinetic stability at high dilution in aqueous solutions, i.e., concentrations at or below nM levels.

Hydroxyisophthalamide ligands useful in applications requiring luminescence have been described (Petoud et al., *J. Am. Chem. Soc.* 2003, 125, 13324-13325; U.S. Pat. No. 7,018,850 to Raymond et al.), and Johansson et al., *J. Am. Chem. Soc.* 2004, 126(50):16451-16455).

However, a need for luminescent complexes, which are stable under biological relevant conditions and at low concentrations, and which simultaneously exhibit low non-specific interactions with proteins, remains. The current invention addresses these and other needs.

SUMMARY OF THE INVENTION

The invention provides a new class of macrocyclic ligands and metal complexes of these ligands. Also provided are conjugates of these ligands with carrier moieties, which are of use in single fluorophore and multiplex applications. The invention also provides mixtures of carrier moieties, each conjugated to a chelate of the invention. Moreover, there are provided mixtures of carrier moieties in which one or more of a first carrier moiety species is conjugated to a chelate of the invention and one or more of a second carrier moiety species is conjugated to a fluorophore different in structure from the chelate attached to the first carrier moiety species. The invention also provides single fluorophore and multiplex assays incorporating one or more chelates of the invention. It is generally preferred that the chelates be bound to a metal ion, which in some embodiments, together with the chelate forms a luminescent metal ion complex.

In particular, the invention provides complexes, e.g., luminescent lanthanide (e.g., terbium and europium) complexes and conjugates of these complexes with a carrier moiety. These complexes exhibit high stability and solubility in aqueous media as well as high quantum yields of luminescence in water without external augmentation (e.g., by micelles or fluoride). The complexes are formed between a metal ion, e.g., of the lanthanide series and a new class of macrocyclic ligands provided by the invention. Preferred ligands incorporate a hydroxy-containing aromatic building block, such as 1,2-hydroxypyridinonyl (1,2-HOPO) or 2,3-hydroxypyridinonyl (2,3-HOPO) moieties within their structure and are characterized by surprisingly low non-specific binding to a variety of different polypeptides such as antibodies and proteins. Because of their unique chemical and physicochemical properties, the complexes of the present invention find use in any application requiring luminescence, particularly in aqueous media, including medical diagnostics and bioanalyical assay systems.

In one aspect, the invention provides a complex formed between at least one metal ion and a chelate according to Formulas I or II (and any other depicted structure), described below. Generally, when a compound of Formula I or II is referred to, other compounds described herein are also contemplated. In contrast to organic fluorophores that have a fluorescence lifetime of about 10 ns, lanthanide chelates of the invention preferably have emission lifetimes greater than 100 microseconds, preferably at least 500 microseconds and even more preferably at least 1 ms. The mechanism that is responsible for the long lifetime emission of lanthanide chelates involves energy transfer from the triplet state of the aromatic ligand. Specifically, upon excitation the ligand is excited to its singlet state and then undergoes an intersystem transition to its triplet state, transferring the energy to the lanthanide ion. Fluorescence is then emitted from the lanthanide ion as it returns to the ground state. Since such fluorescence emission does not result from a singlet-to-singlet transition, the use of lanthanide chelates as a donor results in luminescent resonance energy transfer (LRET). Therefore, by using pulse excitation and time-gating techniques, emission from the fluorophore can be selectively recorded after the background fluorescence from organic dyes, scattering, and autofluorescence has decayed. The only signals remaining in this long-time domain are the emission from the lanthanide chelate and from acceptor fluorophores that have participated in LRET. In this case the narrow emission peaks of a lanthanide chelate render the background fluorescence close to zero at certain wavelengths, leading to extremely large signal-to-background ratio.

In one aspect, the invention provides a compound according to Formula I or II (or other compound, described herein) in a mixture with an analyte. Exemplary analytes include nucleic acids, peptides, antibodies, antigens, lectins, saccharides, cells and receptors.

In one aspect, the invention provides a method of detecting an analyte in a sample, said method comprising: (a) contacting said analyte with a solid support comprising a luminescent complex of the invention, wherein said analyte forms an analyte complex; (b) exciting said luminescent complex such that said luminescent complex transfers excitation energy to said analyte complex; and (c) detecting energy emitted by said analyte complex, thereby detecting said analyte.

In yet a further example, the luminescence modifying group and/or the fluorophore and/or the complex of the invention is a component covalently bound to the analyte.

BRIEF DESCRIPTION OF THE DRAWINGS

FIG. 2 is a table of exemplary fluorophores of use in the compounds of the invention.

DETAILED DESCRIPTION OF THE INVENTION

Definitions

Figure 1:
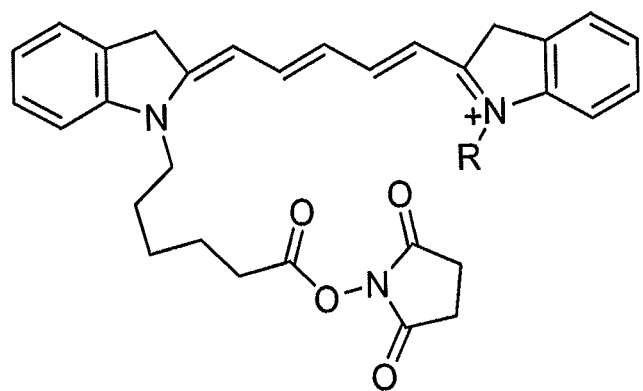
FIG. 1 Exemplary fluorophore acceptor. Cy5 with 649 nm excitation by Eu Donor Peak at 620 nm and a 670 nm emission.
Figure 3A:
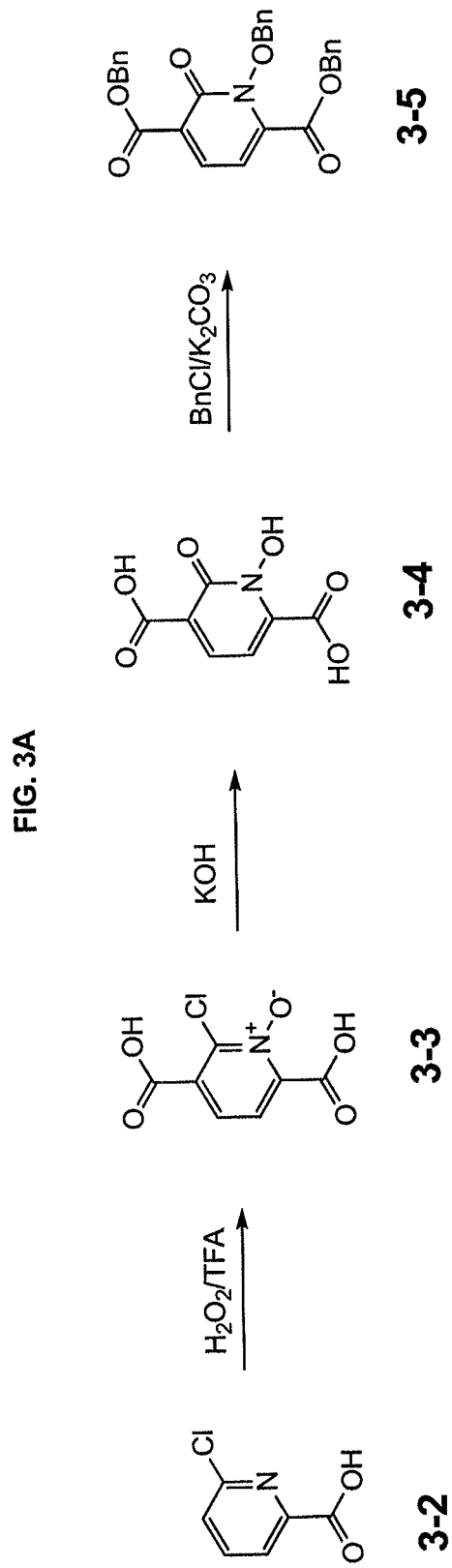
FIG. 3 shows a reaction scheme for synthesizing a macrocyclic 1,2-HOPO chelator that is substituted by a linking arm.
Figure 3B:
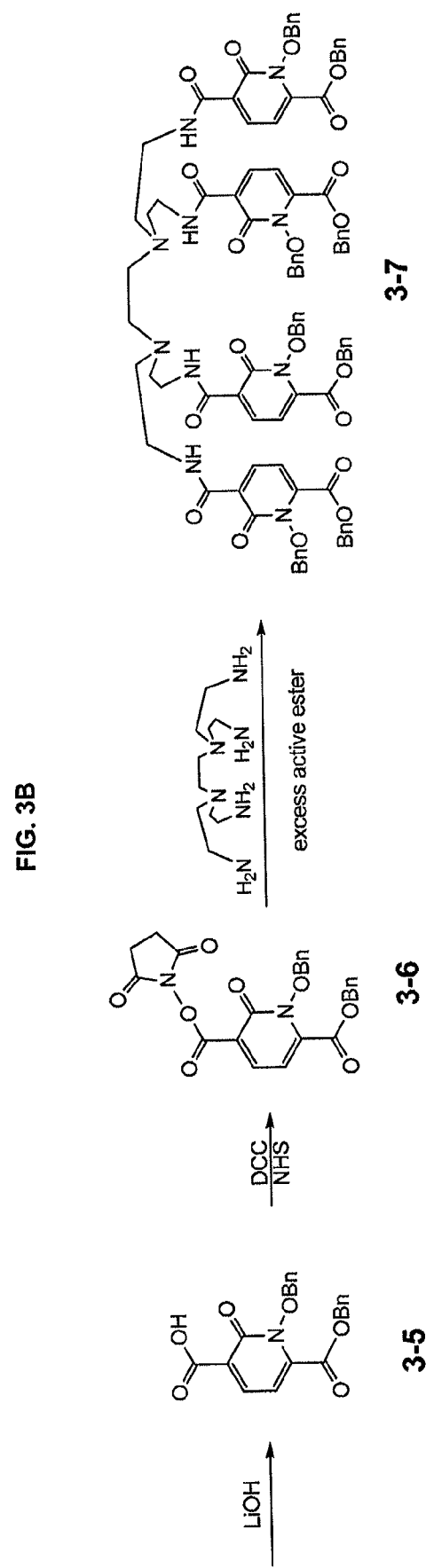
Figure 3C:
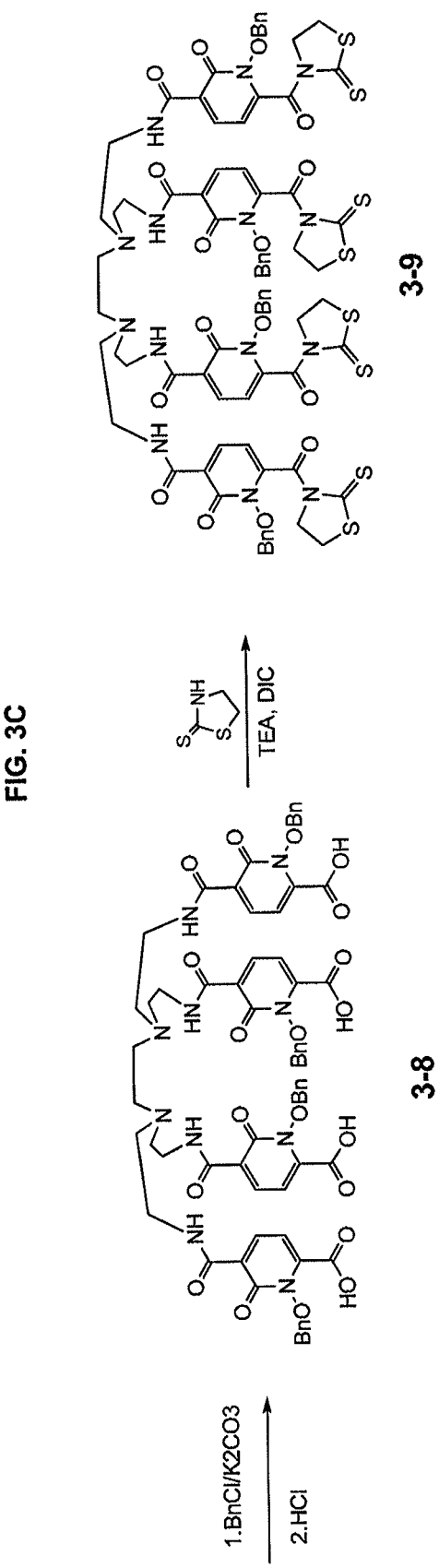
Figure 3D:
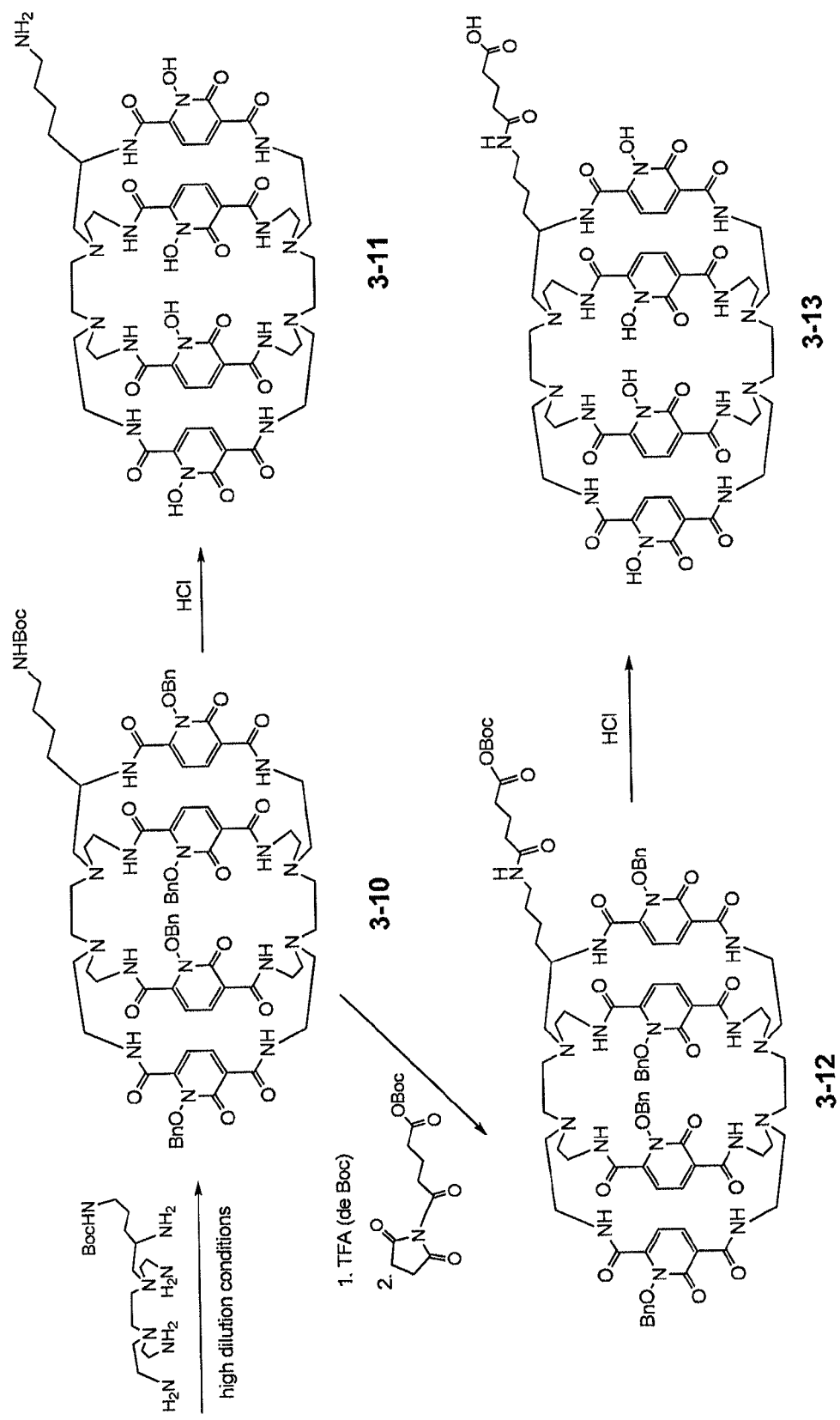
Figure 4A:
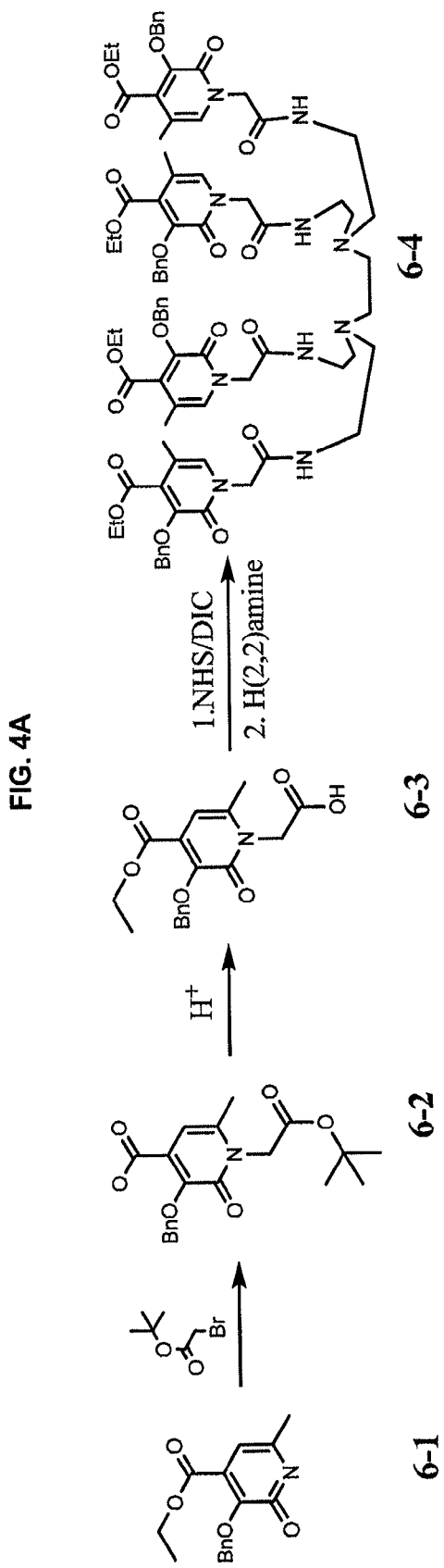
FIG. 4 shows a reaction scheme for synthesizing a macrocyclic 6-Me-3,2-HOPO chelator that is substituted by a linking arm.
Figure 4B:
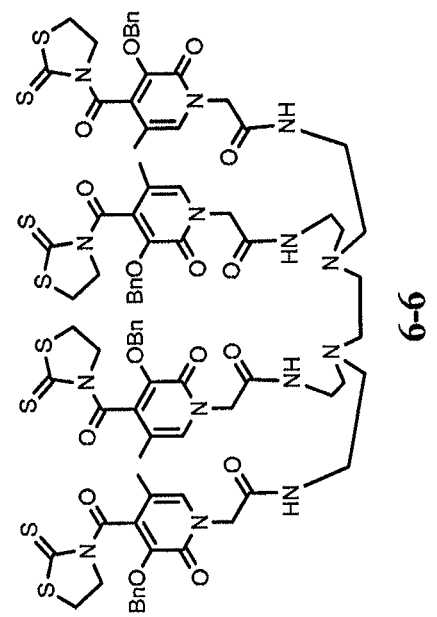
Figure 4B:
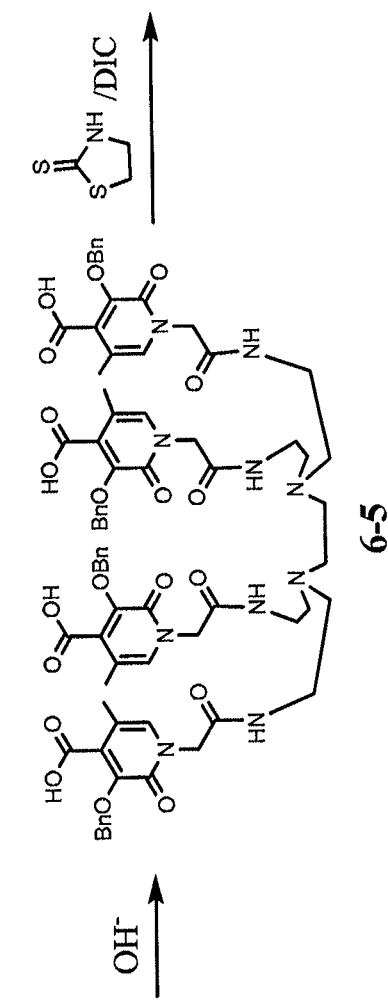
Figure 4C:
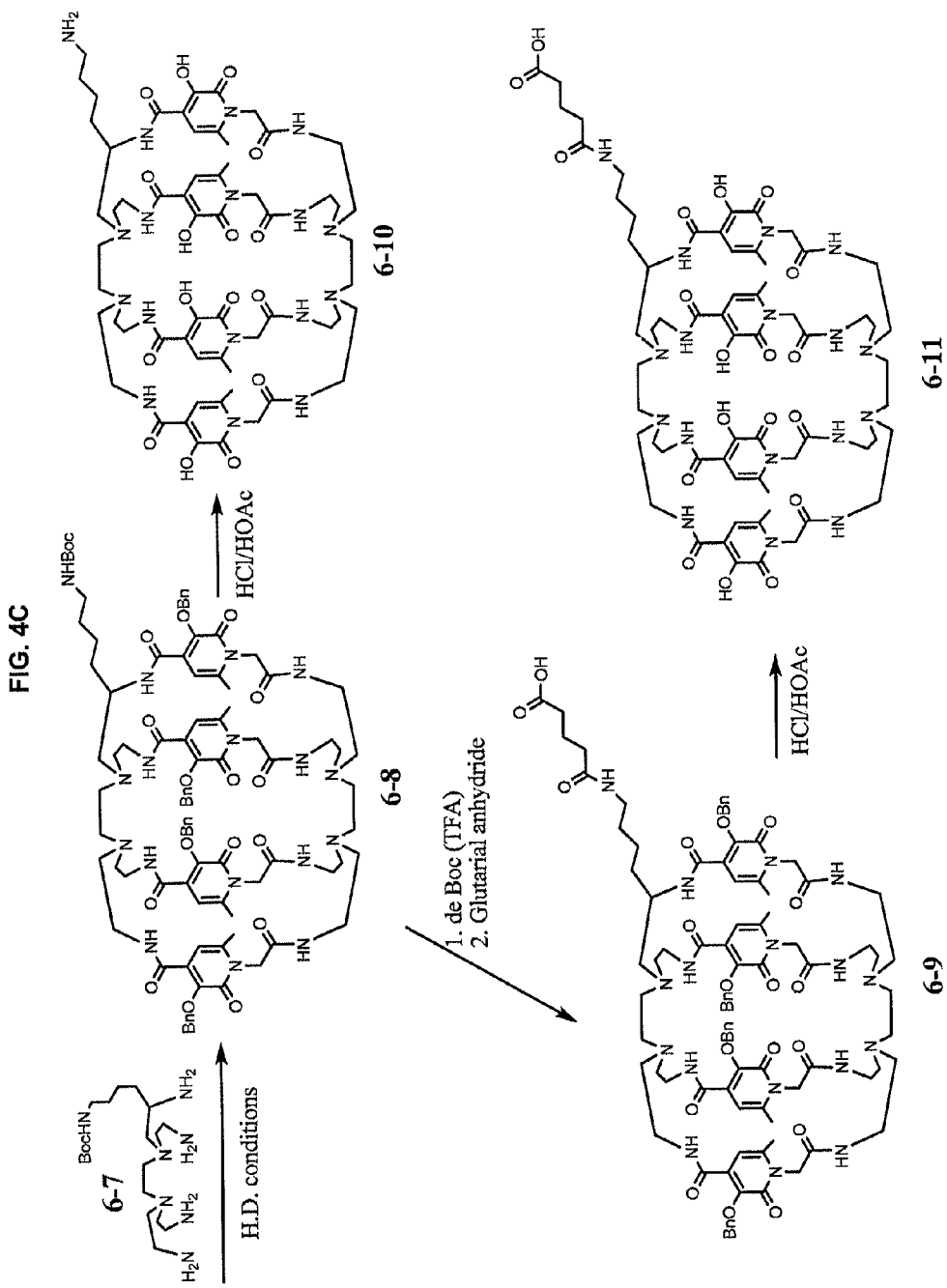
Figure 5A:
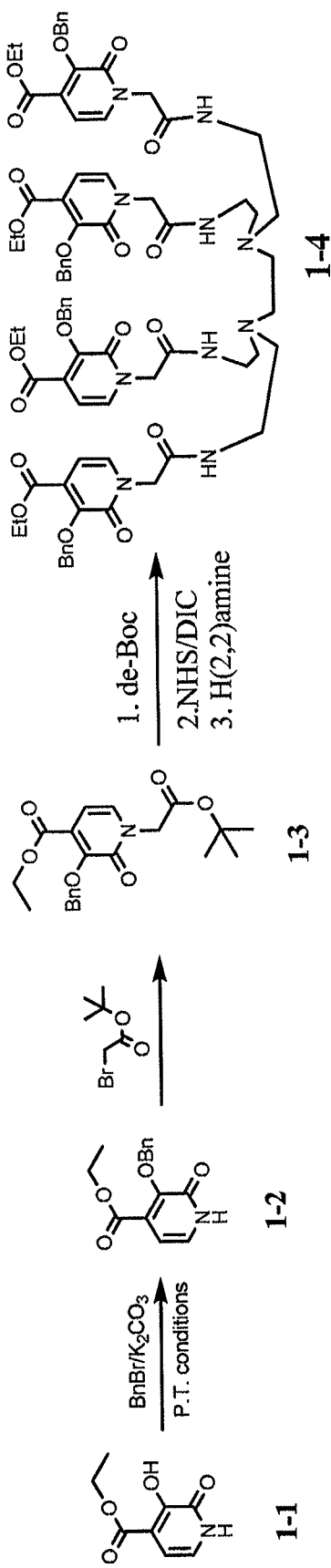
FIG. 5 shows a reaction scheme for synthesizing a macrocyclic 3,2-HOPO chelator that is substituted by a linking arm.
Figure 5B:
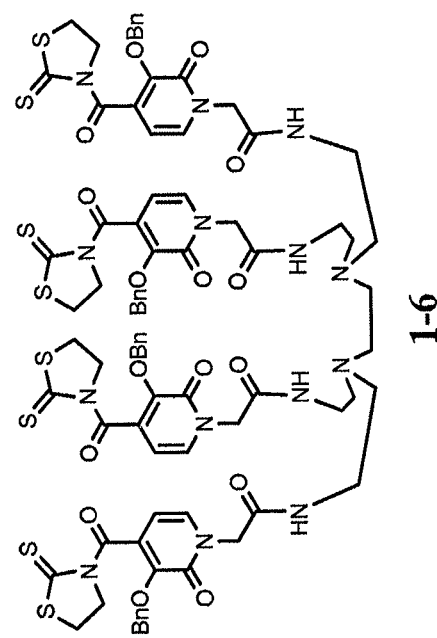
Figure 5B:
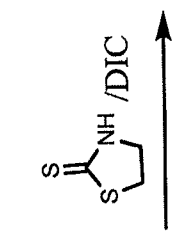
Figure 5B:
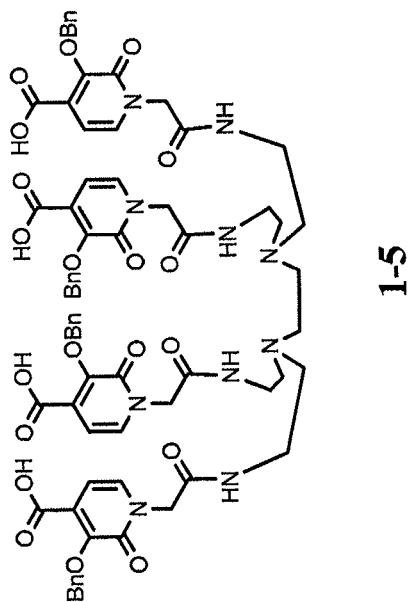
Figure 5B:
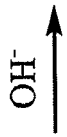
Figure 5C:
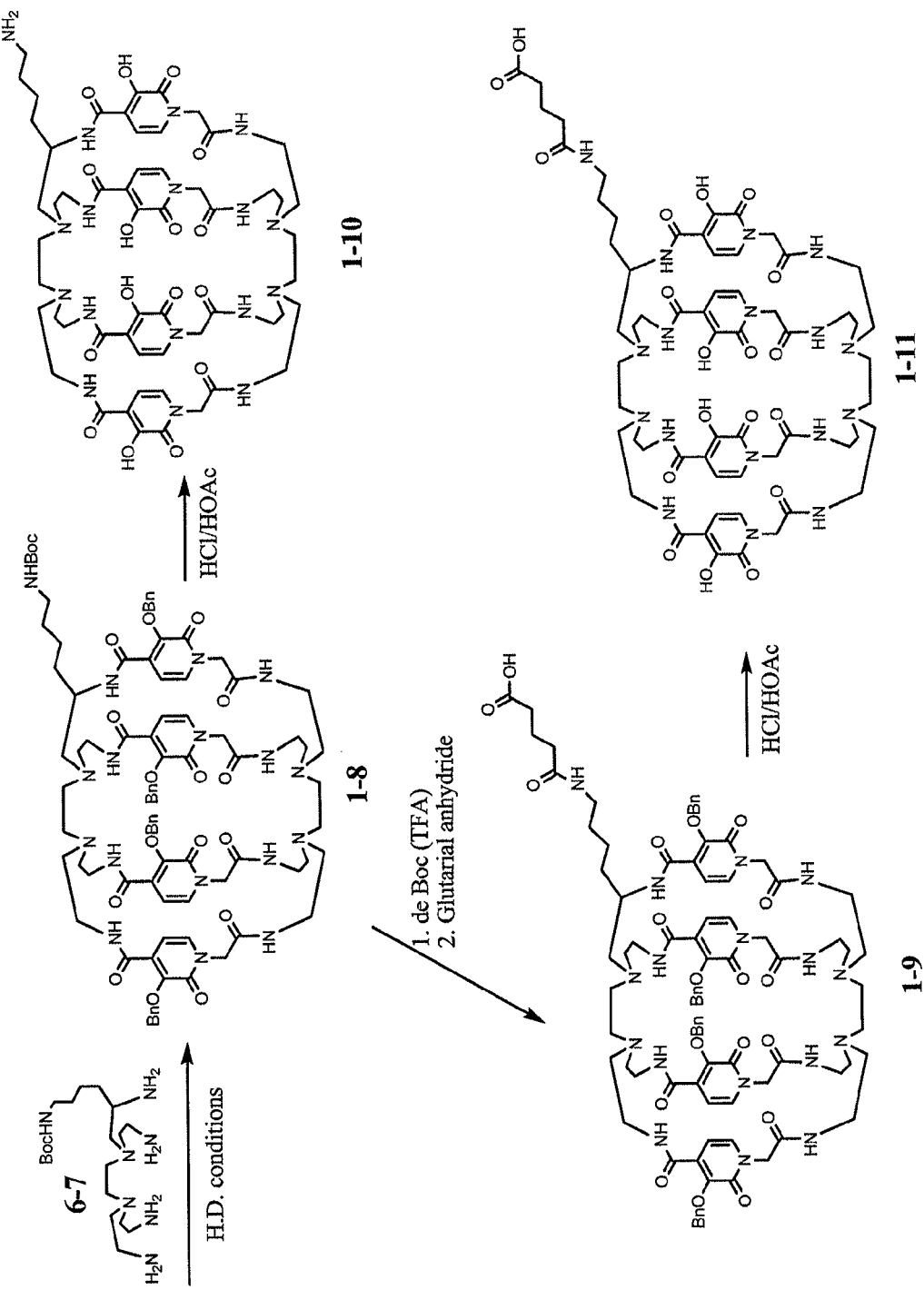

"Analyte", as used herein, means any compound or molecule of interest for which a diagnostic test is performed, such as a biopolymer or a small molecular bioactive material. An analyte can be, for example, a cell, a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, nucleic acid, lipid, without limitation. An analyte can have bound thereto a fluorophore as defined herein and/or a compound according to Formulas I or II. An analyte can be bound to a carrier moiety or to a solid support.

As used herein, "energy transfer" refers to the process by which energy emission of an excited donor (e.g., a luminescent group) is altered by an acceptor (e.g., a luminescence-modifying group). When the luminescence-modifying group is a quenching group then the energy emission from the luminescent group is attenuated (quenched). Energy transfer mechanisms include luminescence resonance energy transfer, e.g., by dipole-dipole interaction (e.g., in longer range energy transfer) or electron transfer (e.g., across shorter distances). An exemplary mechanism involves transfer of energy from a metal chelate to a fluorophore (or a quencher or other luminescence modifying group) covalently bound to the chelating moiety through a linker, such as the compounds of the invention described herein. While energy transfer is often based on spectral overlap of the emission spectrum of the luminescent group and the absorption spectrum of the luminescence-modifying group, (in addition to distance between the groups) it has been demonstrated that spectral overlap is not necessarily required for energy transfer to occur (see, e.g., Latva et al., U.S. Pat. No. 5,998,146, which is incorporated herein by reference) and this type of energy transfer is encompassed within the present invention. Energy transfer between members of an energy transfer pair occurs when the members of the pair are in "operative proximity," which is defined herein as a distance between the members of the pair that allows detectable energy transfer to occur. It is to be understood that any reference to "energy transfer" in the instant application encompasses all mechanistically-similar phenomena.

"Energy transfer pair" is used to refer to a group of molecules that participate in energy transfer. Such complexes may comprise, for example, two luminescent groups, which may be different from one-another and one quenching group, two quenching groups and one luminescent group, or multiple luminescent groups and multiple quenching groups. In cases where there are multiple luminescent groups and/or multiple quenching groups, the individual groups may be different from one another. Typically, one of the molecules acts as a luminescent group, and another acts as a luminescence-modifying group. The preferred energy transfer pair of the invention comprises a luminescent group of the invention and a fluorophore (e.g., an organic fluorophore). The fluorophore can act as a quencher or other luminescence modifying group or, rather than a fluorophore, the acceptor-linker can be conjugated to a quencher or other luminescence modifying moiety. There is no limitation on the identity of the individual members of the energy transfer pair in this application. Generally preferred energy transfer pairs are characterized by a change in the spectroscopic properties of the pair if the distance between the individual members is altered by some critical amount. An exemplary energy transfer pair is a luminescent complex of the invention and an organic fluorophore.

As used herein, "luminescence-modifying group" refers to a molecule of the invention that can alter in any way the luminescence emission from a luminescent group. A luminescence-modifying group generally accomplishes this through an energy transfer mechanism. Depending on the identity of the luminescence-modifying group, the luminescence emission can undergo a number of alterations, including, but not limited to, attenuation, complete quenching, enhancement, a shift in wavelength, a shift in polarity, and a change in luminescence lifetime. One example of a luminescence-modifying group is a fluorophore that participates with a metal complex component of a complex of the invention in fluorescence resonance energy transfer. Another exemplary luminescence-modifying group is a quenching group.

As used herein, "quenching group" refers to any luminescence-modifying group of the invention that can attenuate at least partly the light emitted by a luminescent group. This attenuation is referred to herein as "quenching". Hence, excitation of the luminescent group in the presence of the quenching group leads to an emission signal that is less intense than expected, or even completely absent. Quenching typically occurs through energy transfer between the luminescent group and the quenching group.

"Fluorescence resonance energy transfer" or "FRET" is used interchangeably with and "LRET" and refers to an energy transfer phenomenon in which the excited state energy (e.g., light) emitted by an excited luminescent group is absorbed at least partially by a luminescence-modifying group of the invention and re-emitted at a different (e.g., longer) wavelength by the luminescence-modifying group. FRET depends on energy transfer between the luminescent group and the luminescence-modifying group. The efficiency of FRET depends at least in part on the distance between the luminescence modifying group and the luminescent group. In contrast to excimers and exciplex fluorescence, FRET pairs do not require the dye molecules forming the complexes to be in very close proximity. FRET is commonly used in several detection modes to detect, characterize or identify a variety of biologically active molecules including nucleic acids, e.g., oligonucleotides, peptides (e.g., peptides including one or more protease cleaveage site) and proteins (e.g., antibodies, antigens, receptors). One of the advantages of FRET is that fluorescence arises under physiologically relevant conditions (e.g., pH between about 7 and about 8, e.g., 7.3-7.5) in comparison to exciplex fluorescence which is typically weak under aqueous conditions, requiring the addition of organic solvents or formation in a similar molecular microenvironment. In an one embodiment, the compound according to Formula I or II is incorporated into a nucleic acid having a motif of a known dual- or multiple-labeled nucleic acid probe (e.g., Molecular Beacons, Scorpion probes, TaqMan, and the like). The compound according to Formula I or II and the fluorophore can be positioned analogously to the donor and acceptor moieties of such probes.

"Moiety" refers to the radical of a molecule that is attached to another atom or molecule. The terms "moiety" and "group" are sometimes used interchangeably.

The term "targeting moiety" means any moiety conjugated to the complexes of the invention that targets the complex to a selected target (e.g., a complementary nucleic acid, a receptor structure, an antibody, an antigen, a lectin). The targeting moiety can be a small molecule (e.g., MW<500D), which is intended to include both non-peptides and peptides. The targeting group can also be a macromolecule, which includes saccharides, lectins, receptors, ligands for receptors, proteins such as BSA, antibodies, nucleic acids, solid supports and so forth. The targeting moiety can be a component of the complex of the invention. For example, in one embodiment, the targeting moiety is the acceptor-linker (e.g., the acceptor-linker is a nucleic acid with a sequence sufficiently complementary to the target to allow hybridization between the acceptor-linker and the target). In another embodiment, a targeting moiety is a group conjugated to a functional moiety (e.g., a nucleic acid, antibody, antigen, biotin, avidin, streptavidin, etc.). In exemplary embodiments, the targeting moiety will bind to a target with high binding affinity; a targeting moiety with high binding affinity to a target has a high specificity for or specifically binds to the target. In some embodiments, a high binding affinity is given by a dissociation constant $K_d$ of about $10^{-7}$ M or less. In exemplary embodiments, a high binding affinity is given by a dissociation constant Kd of about $10^{-8}$ M or less, about $10^{-9}$ M or less, about $10^{-10}$ M or less, about $10^{-11}$ M or less, about $10^{-12}$ M or less, about $10^{-13}$ M or less, about $10^{-14}$ M or less or about $10^{-15}$ M or less.

A compound may have a high binding affinity for a target if the compound comprises a targeting moiety that has a high binding affinity for the target.

The term "cleavable group" or "cleavable moiety" refers to a moiety that allows for release of a chelate from the rest of a conjugate by cleaving of a bond linking the chelate (or chelate linker arm construct) to the remainder of the conjugate. A cleavable group or cleavable moiety also refers to a moiety that allows for release of a portion of a chelate from another portion of the chelate. In this way, a cleavable group connects a first portion of a chelate to a second portion of a chelate, and cleavage of the cleavage group causes a separation of the two portions. A cleavable moiety can comprise a "cleaveable bond", which is a bond that undergoes scission under selected conditions. Cleaveable bonds include, but are not limited to, disulfide, imine, carbonate and ester bonds. Cleavage of a cleavable moiety can be, for example, either chemical in nature or enzymatically mediated. Exemplary enzymatically cleavable groups include natural amino acids or peptide sequences that end with a natural amino acid.

In addition to enzymatically cleavable sites, an agent other than an enzyme can be used to cleave a cleavable group. Exemplary non-enzymatic cleavage agents include, but are not limited to, acids, bases, light (e.g., nitrobenzyl derivatives, phenacyl groups, benzoin esters), and heat. Many cleavable groups are known in the art. See, for example, Jung et al, Biochem. Biophys. Acta, 761: 152-162 (1983); Joshi et al, J. Biol. Chem., 265: 14518-14525 (1990); Zarling et al, J. Immunol, 124: 913-920 (1980); Bouizar et al, Eur. J. Biochem., 155: 141-147 (1986); Park et al, J. Biol. Chem., 261: 205-210 (1986); Browning et al, J. Immunol, 143: 1859-1867 (1989). Moreover a broad range of cleavable, bifunctional (both homo- and hetero-bifunctional) spacer arms are commercially available from suppliers such as Pierce.

The term "labile", as understood in the art, refers to a moiety that unusually readily dissociates from the remainder of the molecule to which it is attached. Labile also describes a chemical bond that very easily ruptures or is ruptured. Dissociation of a labile group can be initiated or enhanced by various means as known in the art. Thus, a hydrolytically labile group, an enzymatically labile group, and a metabolically labile group are groups that dissociate under hydrolytic conditions, upon contact with an enzyme or under metabolic conditions, respectively.

"Carrier moiety" or "carrier" as used herein refers to a species to which a compound according to Formula I or II is covalently bound through reaction of a reactive functional group on a functional moiety with a reactive functional group of complementary reactivity on the carrier moiety. Exemplary carrier moieties include nucleic acids (DNA, RNA), peptides (e.g., polypeptides and proteins), antibodies (such as IgG), antibody fragments, antigens, receptors, lectins, saccharides, lipids and the like. Further exemplary carriers include biotin, avidin and streptavidin. A "carrier moiety" can function as a "targeting moiety."

The term, "fluorophore," as used herein refers to a species of excited energy acceptors capable of generating fluorescence when excited, which has a structure other than that shown in Formula I or II or a luminescent metal complex of Formula I or II. Complexes of different metal ions incorporating the structure according to Formula I or II are considered to be different compounds. Thus, for example, if a Tb chelate is a complex according to Formula I or II, an identical Eu complex can be a "fluorophore" according to the present invention. A fluorophore can be covalently bound to a compound according to Formula I or II through a acceptor-linker. Alternatively, the fluorophore can be bound to a first component of an assay, and the compound according to Formula I or II bound to a second component of an assay. Generally, it is preferred that the fluorophore is bound to the first assay component at a position and in a manner that allows energy transfer between the compound according to Formula I or II and the fluorophore when the first and second assay components interact in the assay. An exemplary assay is a hybridization assay in which a fluorophore is bound to a first nucleic acid and a compound according to Formula I or II is bound to a second nucleic acid. Other exemplary acceptors include quenchers and luminescence modifying moieties.

As used herein, "linker", "linking moiety", or "linking group", all used interchangeably, refers to a moiety that joins a chelating moiety (or chelator, for example, any macrocyclic compound) disclosed herein to another species (e.g., carrier moiety or solid support). A "linker", "linking moiety", or "linking group" can also refer to a moiety that joins part of a chelating moiety (or chelator) to another part of a chelator. For example, a linker can be a group that joins $R^{19}$ to any combination of $R^{20}$, $R^{21}$ and $R^{22}$ in the compounds disclosed herein. In some embodiments, a "linker", "linking moiety" or "linking group" refers to a moiety that joins two or more chelating moieties, such as 1,2-HOPO or 3,2-HOPO. Such a linker can be referred to as a "backbone", a "cap", or the like. Examples include those moieties bearing one or more $L^x$ groups and one or more nitrogen atoms as disclosed herein. Exemplary linkers join a reactive functional group (i.e., via a "functional moiety") or a fluorophore (i.e., via an "acceptor-linker") to a chelating moiety or chelator. A linker can be any useful structure including, but not limited to 0-order linkers (i.e., a bond), acyl, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. Further exemplary linkers include substituted or unsubstituted alkyl, substituted or unsubstituted heteroalkyl, substituted or unsubstituted branched or linear $C_1$, $C_2$, $C_3$, $C_4$, $C_5$, $C_6$, $C_7$, $C_8$, $C_9$ or $C_{10}$. Other linkers include nucleic acids and peptides, such as PCR probes, hybridization probes and peptides that include protease cleaveage sites. Still further linkers include antibodies, lectins, haptens and saccharides. Exemplary linking moieties include —C(O)NH—, —C(O)O—, —NH—, —S—, —O—, and the like.

As used herein, "nucleic acid" means DNA, RNA, single-stranded, double-stranded, or more highly aggregated hybridization motifs, and any chemical modifications thereof. Exemplary modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Modifications can also include 3' and 5' modifications such as capping with a quencher, a fluorophore, an intercalator, a minor groove binder or another moiety. Exemplary nucleic acids will bind, preferably under stringent conditions, to a nucleic acid of diagnostic interest. Preferred nucleic acids of diagnostic interest are those that are correlated with a disease, condition or syndrome, or progression, amelioration or treatment of a disease, condition or syndrome. Nonlimiting examples of nucleic acids include those that are sufficiently complementary, to bind under stringent conditions, to a nucleic acid from hepatitis (e.g., A, B or C), human papilloma virus (HPV), human immunodeficiency virus (HIV), influenza, Severe Acute Respiratory Syndrome Virus (SARS), gram positive and gram negative bacteria, and antibiotic resistant bacterial infections, e.g., multiple resistant *Staphylococcus* (MRS).

"Peptide" refers to a homo- or hetero-polymer or -oligomer in which the monomers are amino acids and are joined together through amide bonds, alternatively referred to as a polypeptide. When the amino acids are alpha-amino acids, either the L-optical isomer or the D-optical isomer can be used. Additionally, unnatural amino acids, for example, beta.-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. The term "peptide" or "polypeptide", as used herein, refers to naturally occurring as well as synthetic peptides. In addition, peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

"Reactive functional group," as used herein, has the meaning generally recognized in the art of synthetic chemistry, particularly bioconjugate chemistry. Exemplary reactive functional groups included, without limitation, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Methods to prepare each of these functional groups are well-known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989). Further examples are provided herein.

Where substituent groups are specified by their conventional chemical formulae, written from left to right, they equally encompass the chemically identical substituents, which would result from writing the structure from right to left, e.g., —CH₂O— is intended to also recite —OCH₂—. Similarly,

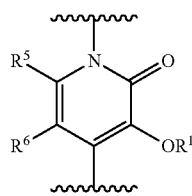

is equivalent to

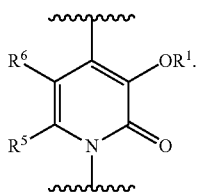

Thus, the incorporation of a moiety depicted with two attachment points into a larger structure is not limited to the depicted orientation of the moiety.

The term "alkyl," by itself or as part of another substituent, means a straight or branched chain, or cyclic hydrocarbon radical, or combination thereof, which may be fully saturated, mono- or polyunsaturated and includes mono-, di- and multivalent radicals, having the number of carbon atoms optionally designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds (i.e., alkenyl and alkynyl moieties). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups that are limited to hydrocarbon groups are termed "homoalkyl". The term "alkyl" can refer to "alkylene", which by itself or as part of another substituent means a divalent radical derived from an alkane, as exemplified, but not limited, by —CH₂CH₂CH₂CH₂—, and further includes those groups described below as "heteroalkylene." Typically, an alkyl (or alkylene) group will have from 1 to 24 carbon atoms, with those groups having 10 or fewer carbon atoms being sometimes preferred. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl and heteroalkyl groups attached to the remainder of the molecule via an oxygen atom, a nitrogen atom (e.g., an amine group), or a sulfur atom, respectively.

The term "heteroalkyl," by itself or in combination with another term, means, unless otherwise stated, a stable straight or branched chain, or cyclic alkyl moiety, or combinations thereof, consisting of a number (e.g., a stated number) of carbon atoms and at least one heteroatom selected from the group consisting of O, N, Si, B and S, and wherein the nitrogen and sulfur atoms may optionally be oxidized and the nitrogen heteroatom may optionally be quaternized. The heteroatom(s) O, N, S, B and Si may be placed at any interior position of the heteroalkyl group or at the position at which the alkyl group is attached to the remainder of the molecule. Examples include, but are not limited to, —CH₂—CH₂—O—CH₃, —CH₂—CH₂—NH—CH₃, —CH₂—CH₂—N(CH₃)—CH₃, —CH₂—S—CH₂—CH₃, —CH₂—CH₂, —S(O)—CH₃, —CH₂—CH₂—S(O)₂—CH₃, —CH=CH—O—CH₃, —Si(CH₃)₃, —CH₂—CH=N—OCH₃, and —CH=CH—N(CH₃)—CH₃. Up to two heteroatoms may be consecutive, such as, for example, —CH₂—NH—OCH₃ and —CH₂—O—Si(CH₃)₃. Similarly, the term "heteroalkylene" by itself or as part of another substituent means a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "acyl" refers to a species that includes the moiety —C(O)R, where R has the meaning defined herein. Exemplary species for R include H, halogen, substituted or unsubstituted alkyl, substituted or unsubstituted aryl, substituted or unsubstituted heteroaryl, and substituted or unsubstituted heterocycloalkyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" or "heteroaryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

In some embodiments, alkyl, heteroalkyl, cycloalkyl, heterocycloalkyl, aryl and heteroaryl may be substituted. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R"', —OC(O)R', —C(O)R', —CO₂R', —CONR'R", —OC(O)NR'R", —NR"C(O)R', —NR'—C(O)NR"R"', —NR"C(O)₂R', —NR—C(NR'R"R"')=NR", —NR—C(NR'R")=NR"', —S(O)R', —S(O)₂R', —S(O)₂NR'R", —NRSO₂R', —CN and —NO₂ in a number ranging from zero to (2m'+1), where m' is the total number of carbon atoms in such radical. In one embodiment, R', R", R"' and R"" each independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. In one embodiment, R', R", R"' and R"" each independently refer to hydrogen, unsubstituted alkyl, unsubstituted heteroalkyl, unsubstituted cycloalkyl, unsubstituted heterocycloalkyl, unsubstituted aryl, unsubstituted heteroaryl, alkoxy or thioalkoxy groups, or arylalkyl groups. When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" can include 1-pyrrolidinyl and 4-morpholinyl.

Similar to the substituents described for the alkyl radical, substituents for the aryl and heteroaryl groups are generically referred to as "aryl group substituents." The substituents are selected from, for example: substituted or unsubstituted alkyl, substituted or unsubstituted heteroalkyl, substituted or unsubstituted heterocycloalkyl, substituted or unsubstituted aryl, substituted or unsubstituted heteroaryl, halogen, —OR', =O, =NR', =N—OR', —NR'R", —SR', -halogen, —SiR'R"R"', —OC(O)R', —C(O)R', —CO₂R', —CONR'R", —OC(O)NR'R", —NR"C(O)R', —NR'—C(O)NR"R"', —NR"C(O)₂R', —NR—C(NR'R"R"')=NR"", —NR—C(NR'R")=NR"', —S(O)R', —S(O)₂R', —S(O)₂NR'R", —NRSO₂R', —CN and —NO₂, —R', —N₃, —CH(Ph)₂, fluoro($C_1$-$C_4$)alkoxy, and fluoro($C_1$-$C_4$)alkyl, in a number ranging from zero to the total number of open valences on the aromatic ring system; and where R', R", R"' and R"" are in some embodiments independently selected from hydrogen, substituted or unsubstituted alkyl, substituted or unsubstituted heteroalkyl, substituted or unsubstituted aryl and substituted or unsubstituted heteroaryl. In some embodiments, R', R", R"' and R"" are independently selected from hydrogen, unsubstituted alkyl, unsubstituted heteroalkyl, unsubstituted aryl and unsubstituted heteroaryl. When a compound of the invention includes more than one R group, for example, each of the R groups is independently selected as are each R', R", R"' and R"" groups when more than one of these groups is present.

Two of the substituents on adjacent atoms of the aryl or heteroaryl ring may optionally be replaced with a substituent of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH₂)$_r$B-, wherein A and B are independently —CRR'—, —O—, —NR—, —S—, —S(O)—, —S(O)₂—, —S(O)₂NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

As used herein, the term "heteroatom" includes oxygen (O), nitrogen (N), sulfur (S), silicon (Si) and boron (B).

A "linkage fragment" (used interchangeably with "linkage") is formed by reaction of a reactive functional group on one species with reactive functional group of complementary reactivity on another species (e.g., a fluorophore and an acceptor-linker, a functional moiety and a carrier moiety (or solid support). Exemplary linkage fragments formed by such reactions include, but are not limited to S, SC(O)NH, SC(O)(NH)$_2$, HNC(O)S, SC(O)O, O, NH, NHC(O), (NH)$_2$C(O), (O)CNH and NHC(O)O, and OC(O)NH, CH$_2$S, CH$_2$O, CH$_2$CH$_2$O, CH$_2$CH$_2$S, (CH$_2$)$_p$O, (CH$_2$)$_p$S or (CH$_2$)$_p$Y'-PEG wherein, Y' is S, NH, NHC(O), C(O)NH, NHC(O)O, OC(O)NH, or O and p is an integer from 1 to 50. In some embodiments, a linkage or linkage fragment is a bond.

Unless otherwise specified, the symbol "R" is a general abbreviation that represents a substituent group that is selected from acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

The present invention includes all salt forms of those molecules that contain ionizable functional groups, such as basic and acidic groups. The term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66: 1-19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

When a residue (such as "R") is defined herein as a single negative charge, then the residue can include a cationic counterion. The resulting salt form of the compound is encompassed in the structure as presented.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The terms "enantiomeric excess" and diastereomeric excess" are used interchangeably herein. Compounds with a single stereocenter are referred to as being present in "enantiomeric excess," those with at least two stereocenters are referred to as being present in "diastereomeric excess." Preferred excesses are at least a percentage selected from 90%, 92%, 94%, 96% and 98%.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Introduction

The present invention provides a class of probes that are based on metal ion (e.g., lanthanide, such as terbium and europium) chelates, which are formed between the metal ion and a novel class of macrocyclic ligands (that is, chelators), such as those set forth in Formula I or II. These complexes exhibit high stability as well as high quantum yields of luminescence in aqueous media without the need for secondary activating agents such micelles or fluoride. Preferred ligands are macrocyclic structures incorporating an aromatic moiety (i.e., a chelating moiety), e.g., hydropyridinonate, within their macrocyclic framework. The macrocycles of the invention may be characterized by surprisingly high kinetic stability and unexpectedly low, non-specific binding to a variety of different polypeptides such as antibodies and proteins. These characteristics distinguish the macrocyclic structures of the invention from known, open-structured ligands.

Lanthanide complexes of the invention exhibit high quantum efficiencies and relatively high absorption coefficients. These properties make metal complexes of ligands of the invention useful for time resolved luminescence resonance energy transfer (TR-LRET) applications (e.g., homogeneous TR-LRET) in which donor and acceptor molecules are used at low concentrations. Complexes of the present invention find use in any application requiring strong luminescence under aqueous conditions including medical diagnostics and bioanalytical assay systems, such as immunoassays, peptide cleavage assays, DNA reporter assays and the like. In addition, these complexes and their derivatives have wide applicability in nanotechnology (incorporation into particles) and material science. In an exemplary embodiment, a complex of the invention is embedded in a solid material, allowing for the transmission of light.

Luminescent metal chelates of the invention can be used with other fluorophores or quenchers as components of energy transfer probes. Many fluorescent labels are useful in combination with the complexes of the invention and many such labels are available from commercial sources, such as SIGMA (Saint Louis) or Invitrogen, that are known to those of skill in the art. Furthermore, those of skill in the art will recognize how to select an appropriate fluorophore for a particular application and, if it is not readily available, will be able to synthesize the necessary fluorophore de novo or synthetically modify commercially available fluorescent compounds to arrive at the desired fluorescent label.

Macrocyclic europium chelates, in particular those incorporating a PEG moiety into their structure, have been discovered to possess advantageous photophysical and spectral properties. The PEG linker effectively increases the overall fluorescent quantum yield through improved water exclusion from the central Eu ion and energy transfer from the ligands to the central metal. This improvement in quantum yield is not accompanied by any significant negative change in emission lifetime, absorption or emission profiles, extinction coefficient or complex thermodynamic stability (pEu). In some cases, a molecule may exhibit 1) a fluorescent quantum yield of at least 16.5%, 2) an absorption maxima between 330-350 nm, 3) a fluorescent lifetime of at least 600 vs, 4) a pEu under standard conditions of at least 18.0 and 5) an extinction coefficient of at least 15,000 $M^{-1} cm^{-1}$. In other cases, a molecule may exhibit 1) a fluorescent quantum yield of at least 5%, 2) an absorption maxima between 330-350 nm, 3) a fluorescent lifetime of at least 600 vs, 4) a pEu under standard conditions of at least 18.0 and 5) an extinction coefficient of at least 12,000 $M^{-1} cm^{-1}$.

In addition to small-molecule fluorophores, naturally occurring fluorescent proteins and engineered analogues of such proteins are useful with the compounds of the present invention. Such proteins include, for example, green fluorescent proteins of cnidarians (Ward et al., *Photochem. Photobiol.* 1982, 35:803-808; Levine et al., *Comp. Biochem. Physiol.* 1982, 72B:77 85), yellow fluorescent protein from *Vibrio fischeri* strain (Baldwin et al., *Biochemistry* 1990, 29:5509 15), Peridinin-chlorophyll from the dinoflagellate *Symbiodinium* sp. (Morris et al., *Plant Molecular Biology* 1994, 24:673:77), phycobiliproteins from marine cyanobacteria, such as Synechococcus, e.g., phycoerythrin and phycocyanin (Wilbanks et al., *J. Biol. Chem.* 1993, 268:1226 35), and the like.

The compounds of the invention can be used as probes, as tools for separating particular ions from other solutes, as probes in microscopy, enzymology, clinical chemistry, molecular biology and medicine. The compounds of the invention are also useful as therapeutic agents and as diagnostic agents in imaging methods. Moreover, the compounds of the invention are useful as components of optical amplifiers of light, waveguides and the like. Furthermore, the compounds of the invention can be incorporated into inks and dyes, such as those used in the printing of currency and other instruments.

In one embodiment, the compounds of the invention show luminescence after exciting them in any manner known in the art, including, for example, with light or electrochemical energy (see, for example, Kulmala et al, *Analytica Chimica Acta* 1999, 386:1). The luminescence can, in the case of chiral compounds of the invention, be circularly polarized (see, for example, Riehl et al., *Chem. Rev.* 1986, 86:1). The present invention provides chiral chelates according to Formula I or II that are enantiomerically or diastereomerically enriched with respect to one enantionmer or diastereomer.

Compositions

In one aspect, the invention provides a compound having a structure according to Formula I:

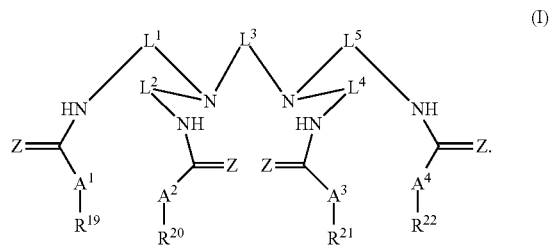

(I)

Each Z is independently selected from O and S. In some embodiments, $L^3$ comprises $—(CH_2CH_2O)_m R^{31}—$ wherein m is an integer selected from 0, 1, 2, 3, 4, 5, 6, 7, 8 and 9. In some embodiments, m is 0. $R^{19}$, $R^{20}$, $R^{21}$ and $R^{22}$ are independently selected from hydroxy, carboxy, amine, amide, ester, a linking member, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $A^1$, $A^2$, $A^3$, $A^4$, $L^1$, $L^2$, $L^4$, $L^5$, $R^{31}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

In exemplary embodiments, at least one of $L^1$, $L^2$, $L^3$, $L^4$ and $L^5$ comprises $-L^{11}-X$ wherein $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and X is a reactive functional group. In some embodiments, $L^1$, $L^2$, $L^3$, $L^4$ and $L^5$ are selected from substituted or unsubstituted alkyl and substituted or unsubstituted heteroalkyl. In some embodiments, $L^1$, $L^2$, $L^3$, $L^4$ and $L^5$ are selected from unsubstituted alkyl and unsubstituted heteroalkyl. In some embodiments, $L^1$, $L^2$, $L^4$ and $L^5$ are selected from unsubstituted alkyl and $L^3$ is unsubstituted heteroalkyl.

At least one of $A^1$, $A^2$, $A^3$ and $A^4$ is selected from

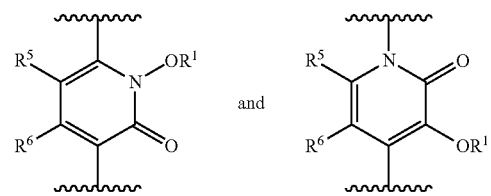

wherein each $R^1$ is independently selected from H, an enzymatically labile group, a hydrolytically labile group, a metabolically labile group, a photolytic group and a single negative charge. Each $R^5$ and $R^6$ is independently selected from H, substituted or unsubstituted alkyl, substituted or unsubstituted heteroalkyl, halogen, CN, $CF_3$, acyl, $—SO_2NR^{17}R_{18}$, $—NR^{17}R^{18}$, $—OR^{17}$, $—S(O)_2R^{17}$, $—COOR^{17}$, $—S(O)_2OR^{17}$, $—OC(O)R^{17}$, $—C(O)NR^{17}R^{18}$, $—NR^{17}C(O)R^{18}$, $—NR^{17}SO_2R^{18}$, and $—NO_2$, wherein $R^5$ and $R^6$ are optionally joined to form a ring system which is a member selected from substituted or unsubstituted cycloalkyl, substituted or unsubstituted heterocycloalkyl, substituted or unsubstituted aryl and substituted or unsubstituted heteroaryl. $R^{17}$ and $R^{18}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{17}$ and $R^{18}$, together with the atoms to which they are attached, are optionally joined to form a 5- to 7-membered ring.

In some embodiments, $A^1$, $A^2$, $A^3$ and $A^4$ are independently selected from

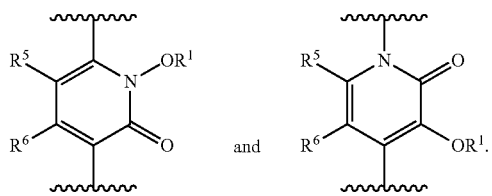

In some embodiments, $A^1$, $A^2$, $A^3$ and $A^4$ are each independently

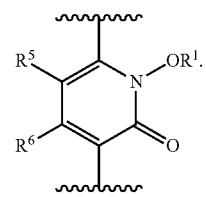

In some embodiment, $A^1$, $A^2$, $A^3$ and $A^4$ are each independently

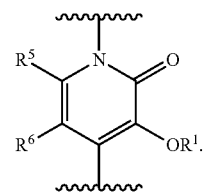

That is, in some embodiments, the orientation of the chelating moieties are mixed with respect to a linking moiety. For example, a compound can have a structure selected from:

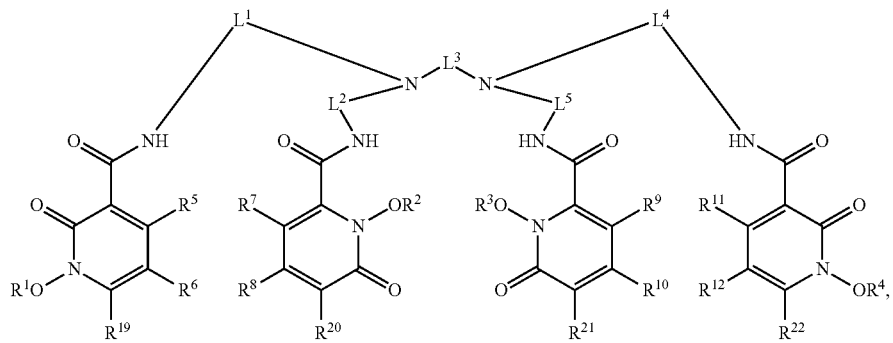

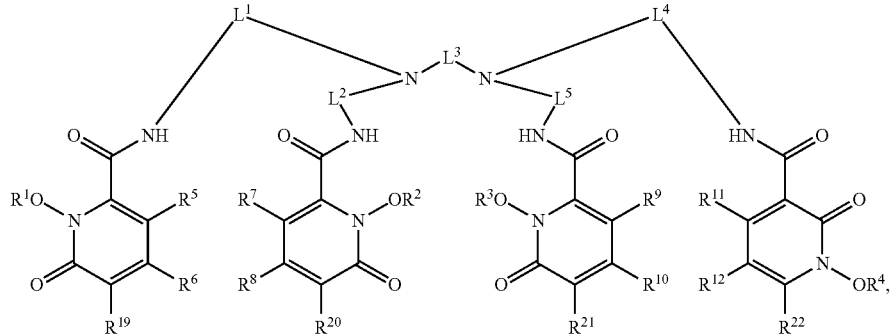

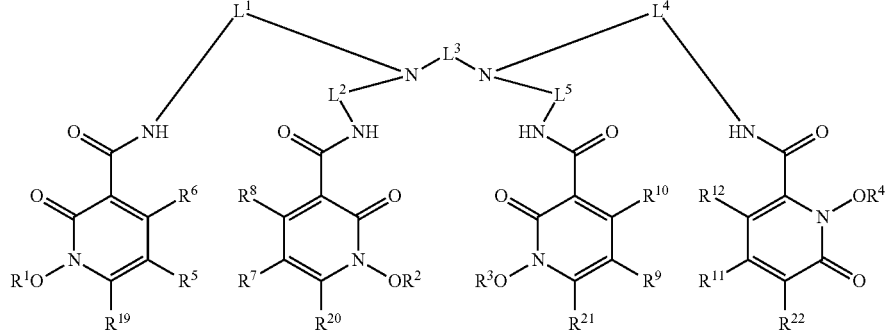

wherein $R^5$, $R^6$, $R^7$, $R^8$, $R^9$, $R^{10}$, $R^{11}$ and $R^{12}$ are members independently selected from H, substituted or unsubstituted alkyl, substituted or unsubstituted heteroalkyl, halogen, CN, $CF_3$, acyl, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, and $-NO_2$, wherein each of pairs $R^5$ and $R^6$, $R^7$ and $R^8$, $R^9$ and $R^{10}$, and $R^{11}$ and $R^{12}$ is optionally joined to form a ring system which is a member selected from substituted or unsubstituted cycloalkyl, substituted or unsubstituted heterocycloalkyl, substituted or unsubstituted aryl and substituted or unsubstituted heteroaryl; and $R^{17}$ and $R^{18}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and $R^{17}$ and $R^{18}$, together with the atoms to which they are attached, are optionally joined to form a 5- to 7-membered ring.

Other examples of mixed orientation structures include compounds having the structures:

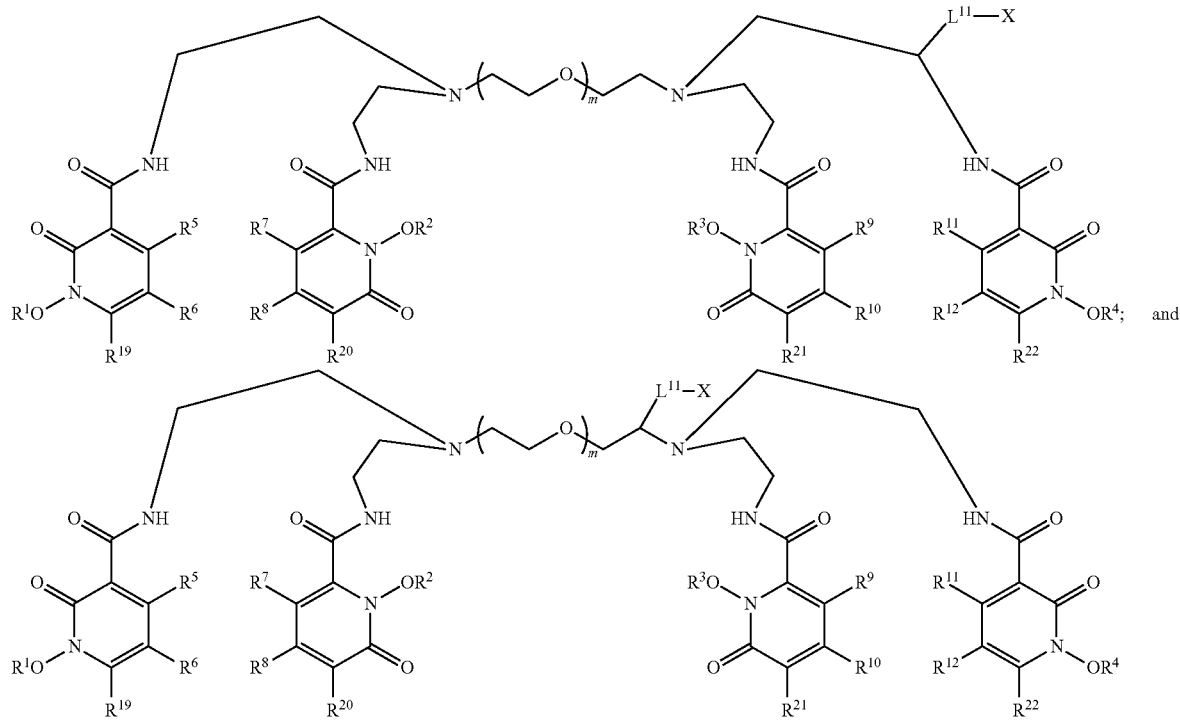

wherein m is an integer selected from 0, 1, 2, 3, 4, 5, 6, 7, 8 and 9, where definitions of the R groups are provided above and elsewhere in the specification.

In some embodiments, $A^1$, $A^2$, $A^3$ and $A^4$ have the same relative orientation; and (a) $A^1$, $A^2$, $A^3$ and $A^4$ are each independently

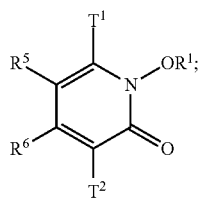

or (b) $A^1$, $A^2$, $A^3$ and $A^4$ are each independently

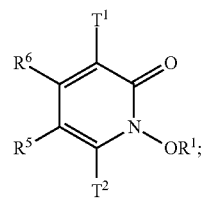

or (c) $A^1$, $A^2$, $A^3$ and $A^4$ are each independently

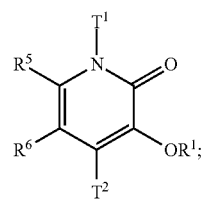

or (d) $A^1$, $A^2$, $A^3$ and $A^4$ are each independently

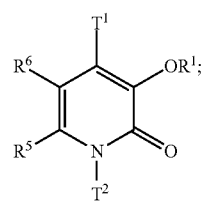

wherein $T^1$ is a bond to a linker having the structure:

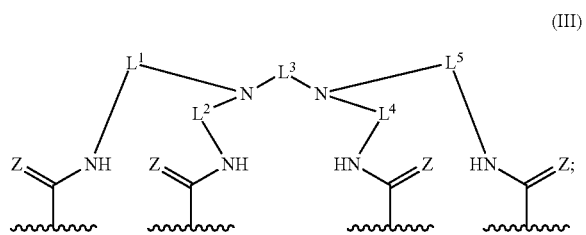

(III)

and $T^2$ is a bond to a group respectively selected from $R^{19}$, $R^{20}$, $R^{21}$ and $R^{22}$. The chelating moieties in subparagraphs (a), (b), (c) and (d) might be considered to have up, down, up and down orientations, respectively, with respect to the linker in Formula III. Accordingly, in various embodiments, a chelator can have chelating moieties in any of the following relative orientations: (1) up, up, up, up; (2) down, up, up, up; (3) up, down, up, up; (4) up, up, down, up; (5) up, up, up, down; (6) down, down, up, up; (7) down, up, down, up; (8) down, up, up, down; (9) up, down, down, up; (10) up, down, up, down; (11) up, up, down, down; (12) down, down, down, up; (13) down, down, up, down; (14) down, up, down, down; (15) up, down, down, down; and (16) down, down, down, down. In any of these combinations, the chelating moiety can be all 1,2-HOPO, all 3,2-HOPO or any combination of 1,2- and 3,2-HOPO.

In exemplary embodiments, Z is O.

In some embodiments, $R^5$ is unsubstituted alkyl. In exemplary embodiments, $R^5$ is methyl. In some embodiments, $R^5$, $R^6$ or both are H. In some embodiments, $R^5$ or $R^6$ is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

In some embodiments, $R^1$ is H or a negative charge. In some embodiments, $R^1$ is independently selected from H, a single negative charge, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In some embodiments, $R^1$ is independently selected from H, a single negative charge, substituted or unsubstituted alkyl and substituted or unsubstituted heteroalkyl. In some embodiments, $R^1$ is independently selected from H, a single negative charge, unsubstituted alkyl and unsubstituted heteroalkyl.

In some embodiments, at least one of $L^1$, $L^2$, $L^3$, $L^4$ and $L^5$ comprises a cleavable group or an activatable group.

In some embodiments, $L^3$ is substituted or unsubstituted heteroalkyl. In exemplary embodiments, $L^3$ is —(CH$_2$CH$_2$O)$_p$(CH$_2$)$_2$—, wherein p is selected from 0, 1, 2, 3, 4, 5, 6, 7, 8 and 9. In exemplary embodiments, p is selected from 3, 4 and 5. In some embodiments, any H is optionally replaced by -$L^{11}$-X. In some embodiments, $L^3$ is substituted or unsubstituted alkyl. In some embodiments, $L^3$ is substituted or unsubstituted ethyl.

In some embodiments, m is an integer selected from 1, 2, 3, 4, 5, 6, 7, 8 and 9.

In some embodiments, $L^1$, $L^2$, $L^4$ and $L^5$ are independently selected substituted or unsubstituted $C_1$ to $C_6$ alkyl. In some embodiments, $L^1$, $L^2$, $L^4$ and $L^5$ are independently selected substituted or unsubstituted ethyl. In exemplary embodiments, $L^1$, $L^2$, $L^4$ and $L^5$ are ethyl. In some embodiments, $R^{31}$ is substituted or unsubstituted $C_1$ to $C_6$ alkyl. In some embodiments, $R^{31}$ is substituted or unsubstituted ethyl. In exemplary embodiments, $R^{31}$ is ethyl.

In exemplary embodiments, one or more groups selected from $L^1$, $L^2$, $L^3$, $L^4$ and $L^5$ is ethyl substituted by -$L^{11}$-X and each of the unselected groups is unsubstituted ethyl. In exemplary embodiments, $L^3$ is substituted by -$L^{11}$-X.

In some embodiments, $L^{11}$ is selected from substituted or unsubstituted alkyl and substituted or unsubstituted heteroalkyl. In some embodiments, $L^{11}$ is unsubstituted alkyl. In some embodiments, $L^{11}$ is substituted heteroalkyl. In some embodiments, $L^{11}$ is unsubstituted heteroalkyl.

In some embodiments, X is selected from —NH$_2$ and —CO(O)H. In some embodiments, X comprises a linkage to a species selected from a fluorophore, a carrier moiety and a solid support.

In some embodiments, -$L^{11}$-X is selected from

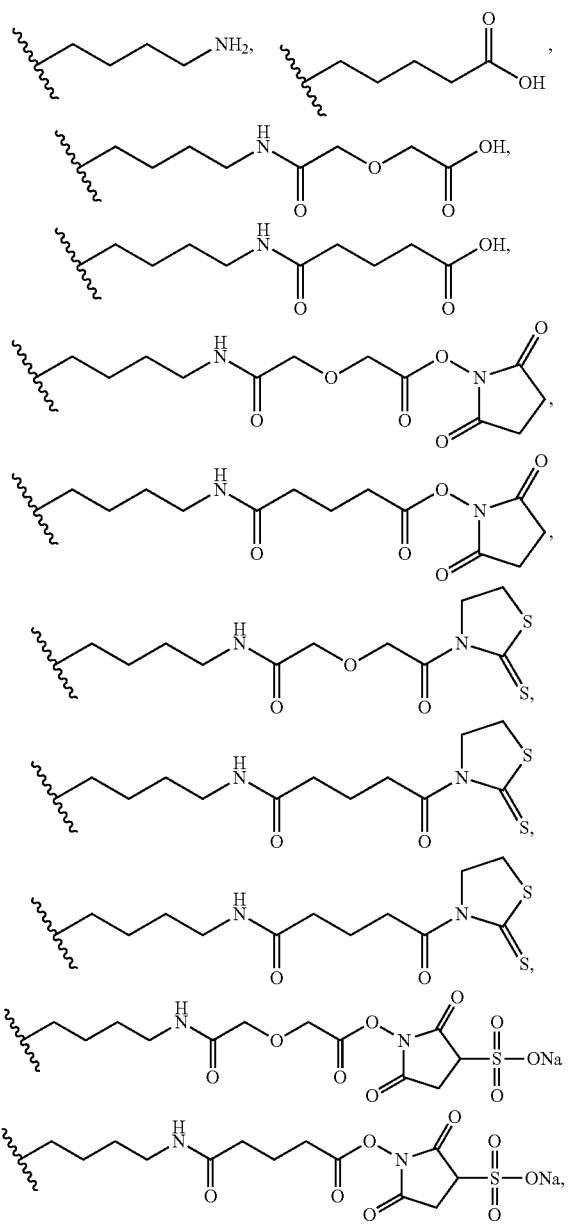

-continued

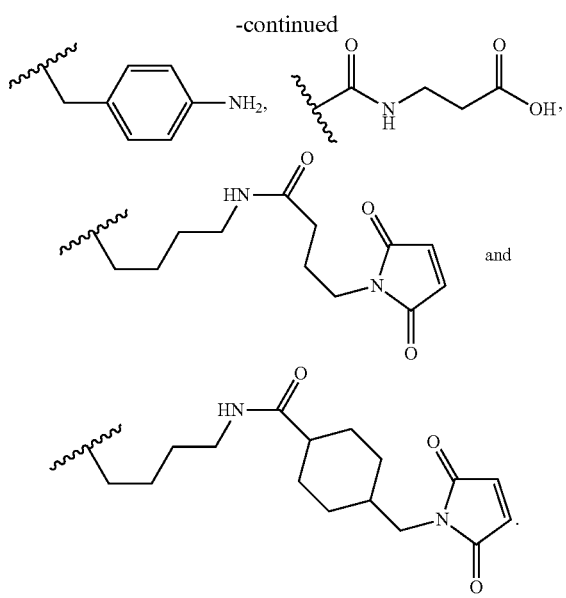

In some embodiments, $R^{19}$, $R^{20}$, $R^{21}$ and $R^{22}$ are independently selected from H, substituted or unsubstituted alkyl and substituted or unsubstituted heteroalkyl. In some embodiments, $R^{19}$, $R^{20}$, $R^{21}$ and $R^{22}$ are independently selected from H, substituted or unsubstituted arylalkyl, substituted or unsubstituted heteroarylalkyl, substituted or unsubstituted arylheteroalkyl and substituted or unsubstituted heteroarylheteroalkyl. In exemplary embodiments, $R^{19}$, $R^{20}$, $R^{21}$ and $R^{22}$ are H.

In one aspect, the invention provides a compound having a structure according to Formula II:

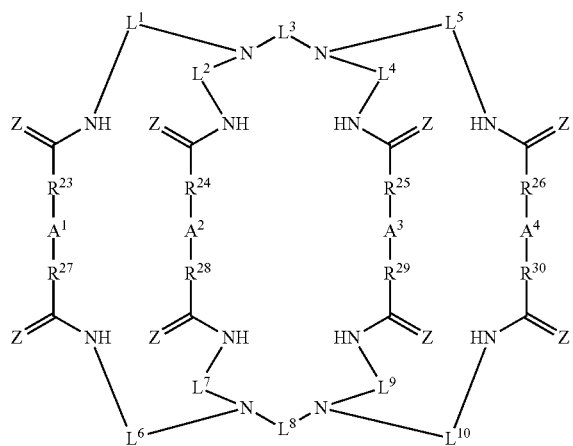

(II)

Each Z is independently selected from O and S. $L^3$ comprises —$(CH_2CH_2O)_mR^{31}$— and $L^8$ comprises —$(CH_2CH_2O)_nR^{32}$— wherein m and n are integers independently selected from 0, 1, 2, 3, 4, 5, 6, 7, 8 and 9. $A^1$, $A^2$, $A^3$, $A^4$, $L^1$, $L^2$, $L^4$, $L^5$, $L^6$, $L^7$, $L^9$, $L^{10}$, $R^{31}$ and $R^{32}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

$R^{23}$, $R^{24}$, $R^{25}$, $R^{26}$, $R^{27}$, $R^{28}$, $R^{29}$ and $R^{30}$ are independently selected from a bond, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

At least one of $A^1$, $A^2$, $A^3$ and $A^4$ is selected from

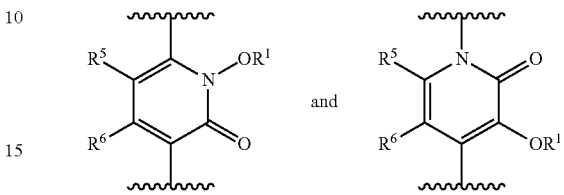

and wherein each $R^1$ is independently selected from H, an enzymatically labile group, a hydrolytically labile group, a metabolically labile group, a photolytic group and a single negative charge. Each $R^5$ and $R^6$ is independently selected from H, substituted or unsubstituted alkyl, substituted or unsubstituted heteroalkyl, halogen, CN, $CF_3$, acyl, —$SO_2NR^{17}R^{18}$, —$NR^{17}R^{18}$, —$OR^{17}$, —$S(O)_2R^{17}$, —$COOR^{17}$, —$S(O)_2OR^{17}$, —$OC(O)R^{17}$, —$C(O)NR^{17}R^{18}$, —$NR^{17}C(O)R^{18}$, $NR^{17}SO_2R^{18}$, and —$NO_2$, $R^5$ and $R^6$ are optionally joined to form a ring system which is a member selected from substituted or unsubstituted cycloalkyl, substituted or unsubstituted heterocycloalkyl, substituted or unsubstituted aryl and substituted or unsubstituted heteroaryl. $R^{17}$ and $R^{18}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $R^{17}$ and $R^{18}$, together with the atoms to which they are attached, are optionally joined to form a 5- to 7-membered ring.

In some embodiments, $A^1$, $A^2$, $A^3$ and $A^4$ are independently selected from

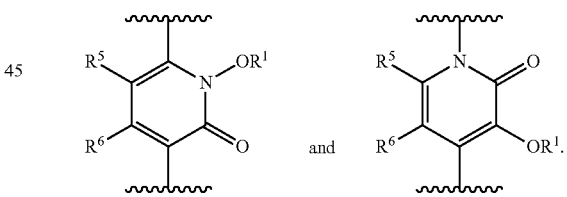

and

The compounds herein can comprise the same type of chelating moiety, in the same or different orientation in relation to a linking group. In some embodiments, $A^1$, $A^2$, $A^3$ and $A^4$ are each independently

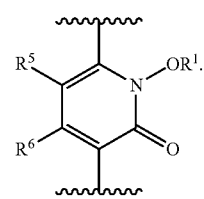

In some embodiments, $A^1$, $A^2$, $A^3$ and $A^4$ are each independently

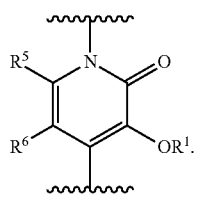

In some embodiments, $A^1$, $A^2$, $A^3$ and $A^4$ have the same relative orientation; and (a) $A^1$, $A^2$, $A^3$ and $A^4$ are each independently

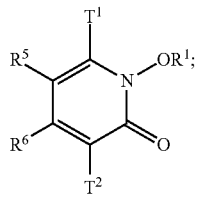

or (b) $A^1$, $A^2$, $A^3$ and $A^4$ are each independently

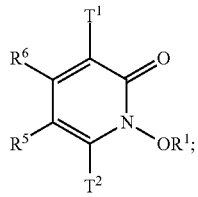

or (c) $A^1$, $A^2$, $A^3$ and $A^4$ are each independently

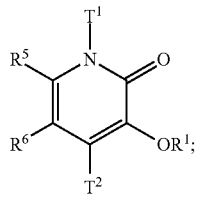

or (d) $A^1$, $A^2$, $A^3$ and $A^4$ are each independently

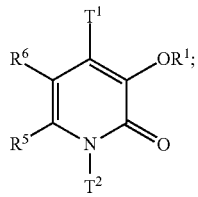

wherein $T^1$ is a bond to a linker having the structure:

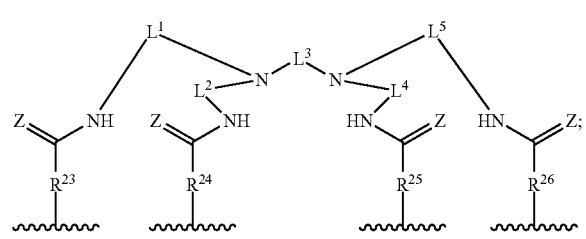

and $T^2$ is a bond to a linker having the structure:

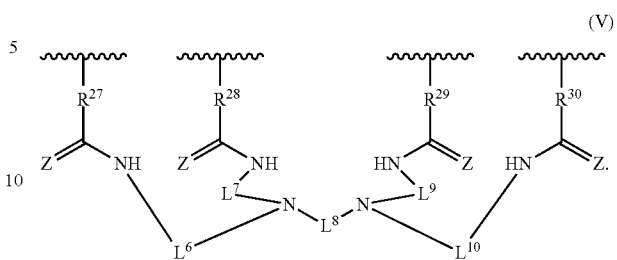

The chelating moieties in subparagraphs (a), (b), (c) and (d) might be considered to have up, down, up and down orientations, respectively, with respect to the linkers in Formulas VI and V. Accordingly, in various embodiments, a chelator can have chelating moieties in any of the following relative orientations: (1) up, up, up, up; (2) down, up, up, up; (3) up, down, up, up; (4) up, up, down, up; (5) up, up, up, down; (6) down, down, up, up; (7) down, up, down, up; (8) down, up, up, down; (9) up, down, down, up; (10) up, down, up, down; (11) up, up, down, down; (12) down, down, down, up; (13) down, down, up, down; (14) down, up, down, down; (15) up, down, down, down; and (16) down, down, down, down. In any of these combinations, the chelating moiety can be all 1,2-HOPO, all 3,2-HOPO or any combination of 1,2- and 3,2-HOPO.

In exemplary embodiments, Z is O.

In some embodiments, $R^5$ is unsubstituted alkyl. In some embodiments, $R^5$ is methyl. In some embodiments, $R^5$, $R^6$ or both are H. In some embodiments, $R^5$ or $R^6$ is selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl.

In some embodiments, $R^1$ is H or a negative charge. In some embodiments, $R^1$ is independently selected from H, a single negative charge, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. In some embodiments, $R^1$ is independently selected from H, a single negative charge, substituted or unsubstituted alkyl and substituted or unsubstituted heteroalkyl. In some embodiments, $R^1$ is independently selected from H, a single negative charge, unsubstituted alkyl and unsubstituted heteroalkyl.

In some embodiments, $R^{23}$, $R^{24}$, $R^{25}$, $R^{26}$, $R^{27}$, $R^{28}$, $R^{29}$ and $R^{30}$ are independently selected from a bond, substituted or unsubstituted alkyl, substituted or unsubstituted heteroalkyl. In some embodiments, $R^{23}$, $R^{24}$, $R^{25}$ and $R^{26}$ are a bond. In some embodiments, $R^{23}$, $R^{24}$, $R^{25}$, $R^{26}$, $R^{27}$, $R^{28}$, $R^{29}$ and $R^{30}$ are a bond. In some embodiments, $R^{27}$, $R^{28}$, $R^{29}$ and $R^{30}$ are substituted alkyl. In some embodiments, $R^{27}$, $R^{28}$, $R^{29}$ and $R^{30}$ are unsubstituted alkyl. In some embodiments, $R^{27}$, $R^{28}$, $R^{29}$ and $R^{30}$ are $C_1$-$C_6$ alkyl. In some embodiments, $R^{27}$, $R^{28}$, $R^{29}$ and $R^{30}$ are methyl.

In some embodiments, m, n or both are an integer independently selected from 1, 2, 3, 4, 5, 6, 7, 8 and 9. In some embodiments, one of m and n is zero and the other is greater than 0. The integers m and n can be the same or different.

In some embodiments, at least one of $L^1, L^2, L^3, L^4, L^5, L^6, L^7, L^8, L^9$ and $L^{10}$ comprises a cleavable group or an activatable group.

In some embodiments, $L^3, L^8$ or both are independently substituted or unsubstituted heteroalkyl. In some embodiments, $L^3, L^8$ or both are independently substituted by $-L^{11}-X$. In some embodiments, $L^3, L^8$ or both is substituted or unsubstituted alkyl. In some embodiments, $L^3, L^8$ or both is substituted or unsubstituted ethyl.

In some embodiments, $L^1, L^2, L^4, L^5, L^6, L^7, L^9$, and $L^{10}$ are independently selected from substituted or unsubstituted $C_1$ to $C_6$ alkyl. In some embodiments, $L^1, L^2, L^4, L^5, L^6, L^7, L^9$, and $L^{10}$ are independently selected from substituted or unsubstituted ethyl. In some embodiments, $L^1, L^2, L^4, L^5, L^6, L^7, L^9$ and $L^{10}$ are ethyl. In some embodiments, $R^{31}, R^{32}$ or both are independently selected from substituted or unsubstituted $C_1$ to $C_6$ alkyl. In some embodiments, $R^{31}, R^{32}$ or both are independently selected from substituted or unsubstituted ethyl. In some embodiments, $R^{31}, R^{32}$ or both are ethyl.

In exemplary embodiments, at least one of $L^1, L^2, L^3, L^4, L^5, L^6, L^7, L^8, L^9$ and $L^{10}$ is substituted by $-L^{11}-X$, wherein $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and X is a functional moiety.

In exemplary embodiments, one or more groups selected from $L^1, L^2, L^3, L^4, L^5, L^6, L^7, L^8, L^9$ and $L^{10}$ is ethyl substituted by $-L^{11}-X$ and each of the unselected groups is unsubstituted ethyl.

In some embodiments, $L^{11}$ is selected from substituted or unsubstituted alkyl and substituted or unsubstituted heteroalkyl. In some embodiments, $L^{11}$ is unsubstituted alkyl. In some embodiments, $L^{11}$ is substituted heteroalkyl. In some embodiments, $L^{11}$ is unsubstituted heteroalkyl.

In some embodiments, X is selected from $-NH_2$ and $-CO(O)H$.

In some embodiments, $-L^{11}-X$ is selected from

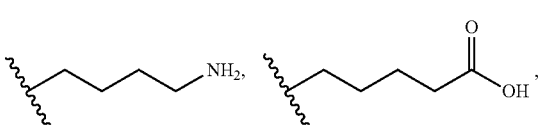

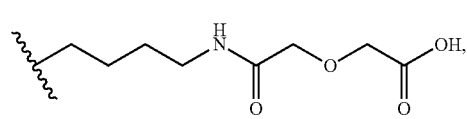

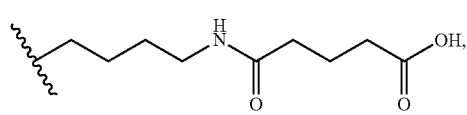

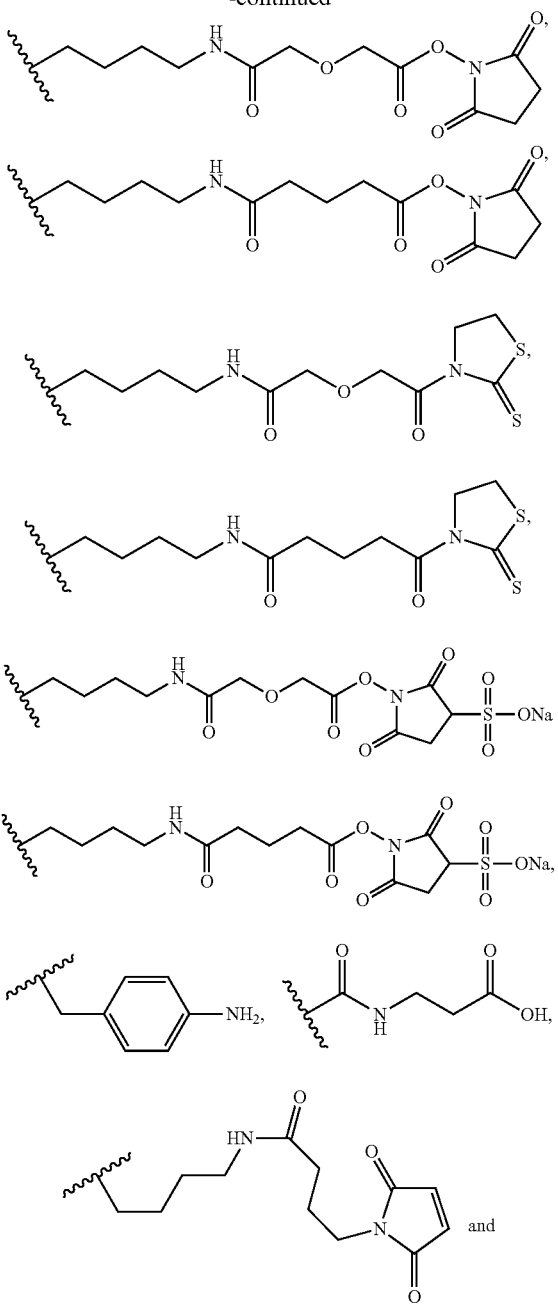

In some embodiments, X comprises a linkage to a species selected from a fluorophore, a carrier moiety and a solid support.

In exemplary embodiments, a compound has a structure selected from:

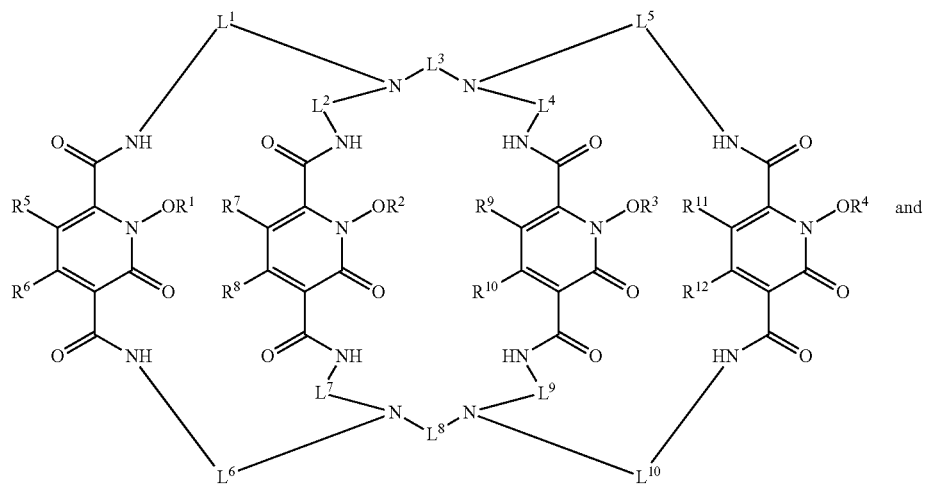

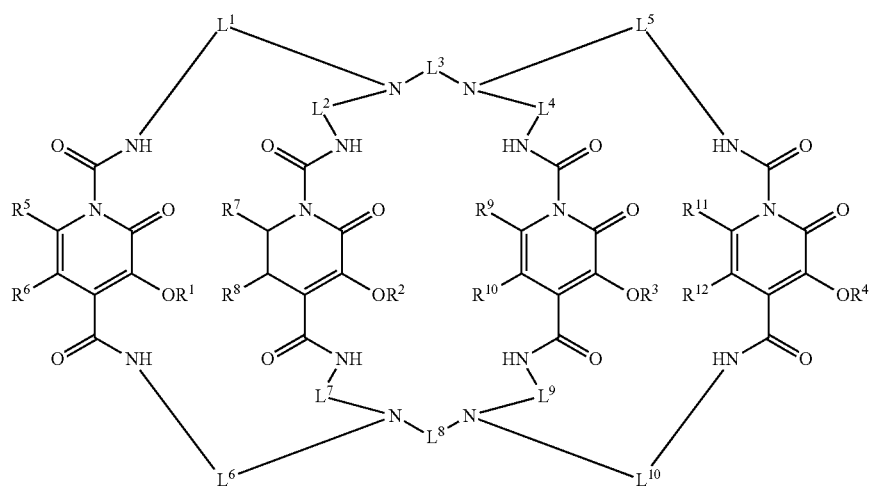

wherein $R^1$, $R^2$, $R^3$ and $R^4$ are members independently selected from H, an enzymatically labile group, a hydrolytically labile group, a metabolically labile group, a photolytic group and a single negative charge. $R^7$, $R^8$, $R^9$, $R^{10}$, $R^{11}$ and $R^{12}$ are members independently selected from H, substituted or unsubstituted alkyl, substituted or unsubstituted heteroalkyl, halogen, CN, $CF_3$, acyl, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, and $-NO_2$, wherein each of pairs $R^7$ and $R^8$, $R^9$ and $R^{10}$, and $R^{11}$ and $R^{12}$ is optionally joined to form a ring system which is a member selected from substituted or unsubstituted cycloalkyl, substituted or unsubstituted heterocycloalkyl, substituted or unsubstituted aryl and substituted or unsubstituted heteroaryl; and $R^{17}$ and $R^{18}$ are members independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and $R^{17}$ and $R^{18}$, together with the atoms to which they are attached, are optionally joined to form a 5- to 7-membered ring.

In exemplary embodiments, $L^1$, $L^2$, $L^4$, $L^5$, $L^6$, $L^7$, $L^9$ and $L^{10}$ are independently selected from substituted or unsubstituted $C_1$ to $C_6$ alkyl. In exemplary embodiments, $L^1$, $L^2$, $L^4$, $L^5$, $L^6$, $L^7$, $L^9$ and $L^{10}$ are independently selected from substituted or unsubstituted ethyl. In exemplary embodiments, $L^1$, $L^2$, $L^4$, $L^5$, $L^6$, $L^7$, $L^9$ and $L^{10}$ are ethyl. In exemplary embodiments, $R^{31}$ and $R^{32}$ are independently selected from substituted or unsubstituted $C_1$ to $C_6$ alkyl. In exemplary embodiments, $R^{31}$ and $R^{32}$ are independently selected from substituted or unsubstituted ethyl. In exemplary embodiments, $R^{31}$ and $R^{32}$ are ethyl.

In exemplary embodiments, a compound has a structure that is selected from:

31 32
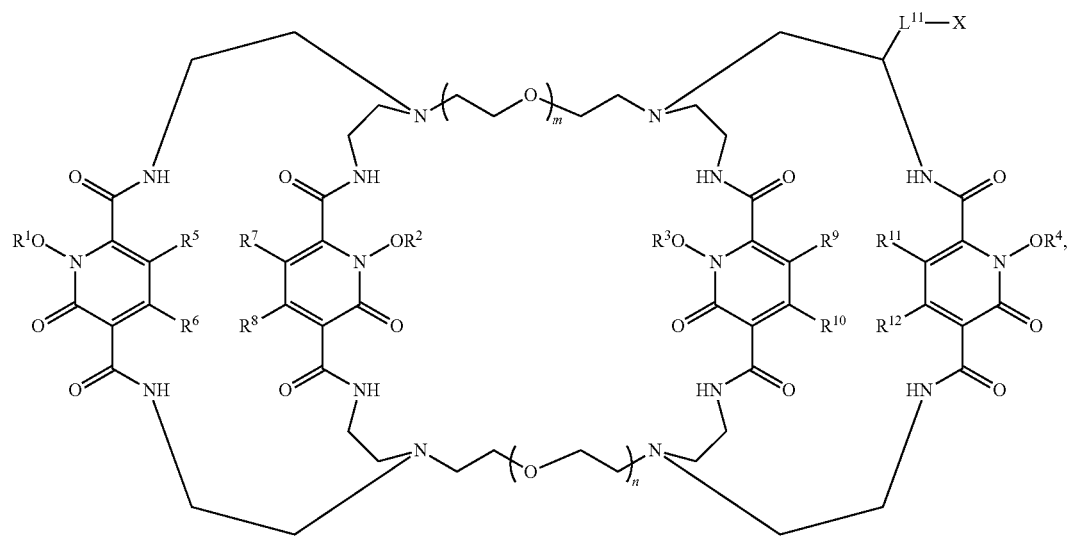
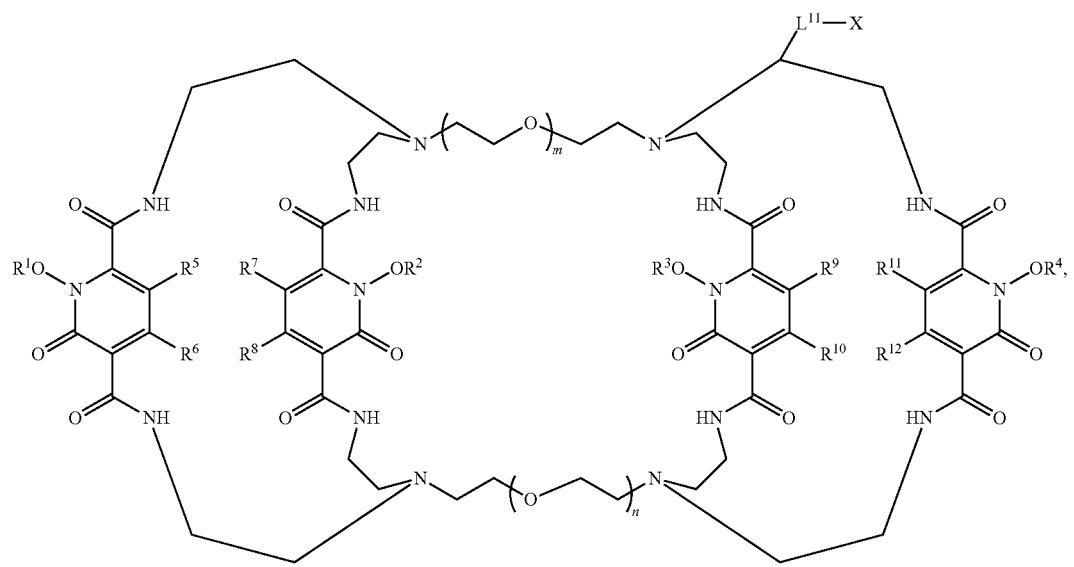
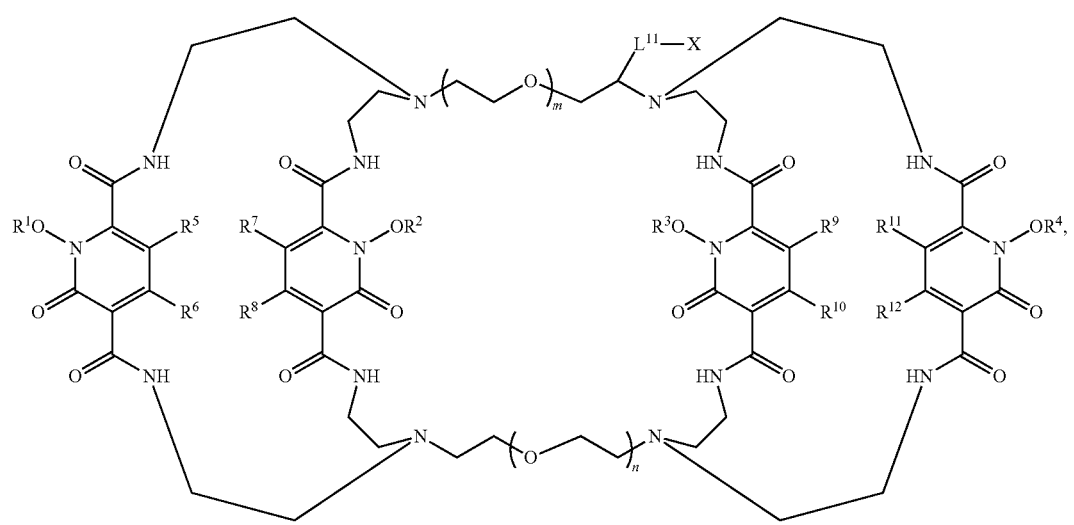

-continued
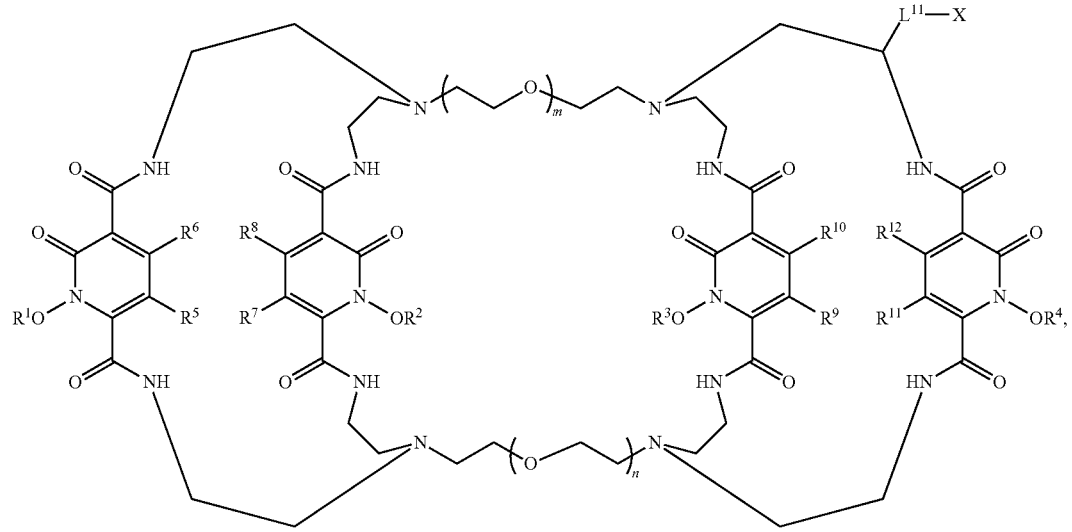
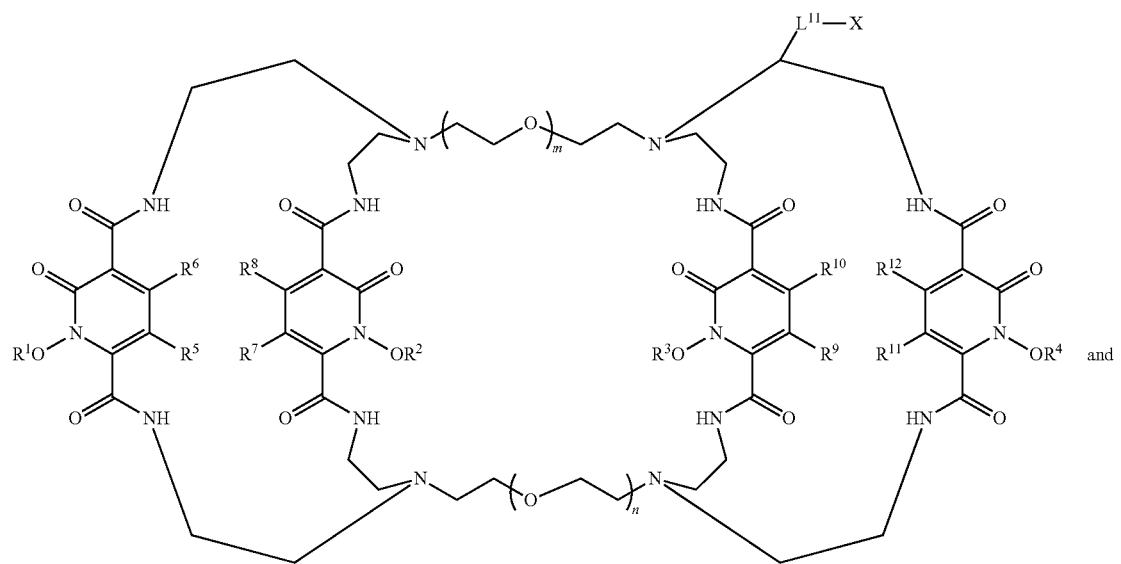 and
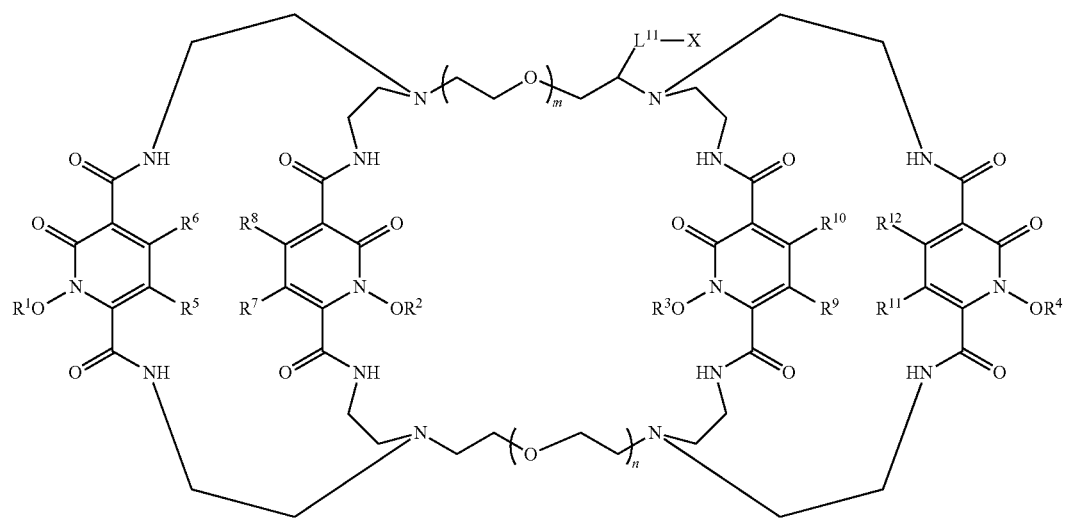

wherein m and n are integers independently selected from 0, 1, 2, 3, 4, 5, 6, 7, 8 and 9 (e.g., 3, 4 and 5). In some embodiments, at least one of m and n is not 0. $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and X is a functional moiety. The definitions of the various R groups are provided through the specification. It can be appreciated that 1,2-HOPO can be replaced by

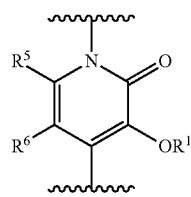

in any orientation but in particular where all have the same orientation with respect to their attachment points.

In exemplary embodiments, $R^1$, $R^2$, $R^3$, $R^4$, $R^5$, $R^6$, $R^7$, $R^8$, $R^9$ and $R^{10}$ are H or a single negative charge.

In exemplary embodiments -$L^{11}$-X is selected from

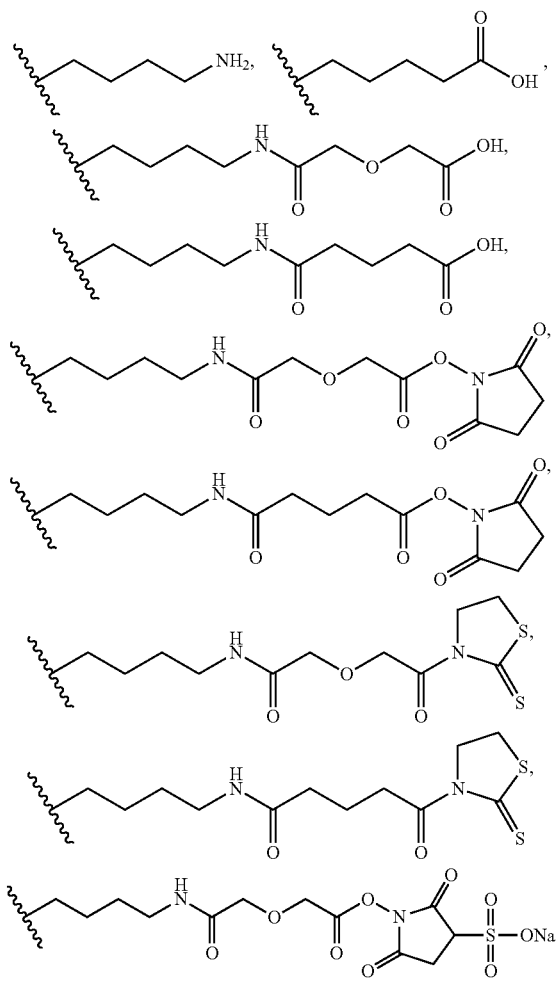

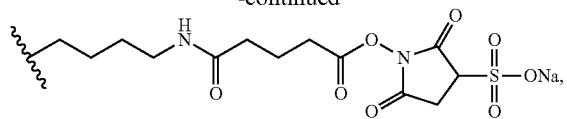

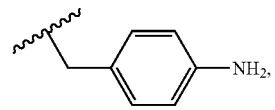

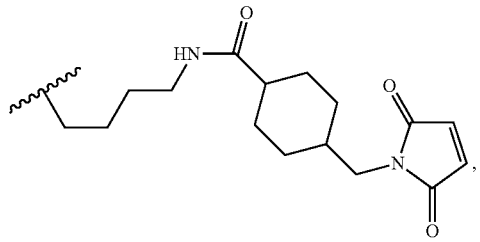 [SMILES: *CCCCNC(=O)C1CCC(CN2C(=O)C=CC2=O)CC1]

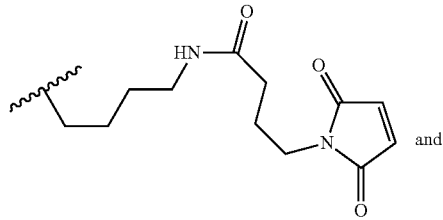

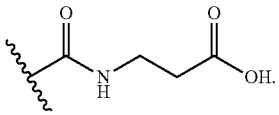

In some embodiments, the integer m is selected from 0-8. In some embodiments, the integer m is selected from 0-7. In some embodiments, the integer m is selected from 0-6. In some embodiments, the integer m is selected from 0-5. In some embodiments, the integer m is selected from 0, 1, 2, 3, 4, 5, 6, 7, 8 and 9. In some embodiments, the integer n is selected from 0-8. In some embodiments, the integer n is selected from 0-7. In some embodiments, the integer n is selected from 0-6. In some embodiments, the integer n is selected from 0-5. In some embodiments, the integer n is selected from 0, 1, 2, 3, 4, 5, 6, 7, 8 and 9.

Functional Moiety/Acceptor-linker

In some embodiments, a compound of the invention comprises at least one functional moiety. In some embodiments, a reactive functional group on the functional moiety is converted to a linkage fragment by reaction with a complementary reactive group on a carrier moiety.

Functional moieties and acceptor linkers have a structure appropriate to allow their covalent attachment to a carrier moiety (or solid support) or a fluorophore (e.g., an organic fluorophore), respectively. Prior to conjugation with a fluorophore or carrier moiety (or solid support), the acceptor-linker and the functional moiety include a reactive functional group.

In a further embodiment, the acceptor-linker and/or the functional moiety is bound to a fluorophore or carrier moiety (or solid support), respectively. Binding of the fluorophore or carrier moiety is effected through reaction of complementary functional groups on the fluorophore, or carrier moiety, and the acceptor-linker or functional moiety, respectively, thereby forming a linkage fragment which joins the two components. Exemplary linkage fragments (sometimes referred to as a linkage) include: S, SC(O)NH, SC(O)(NH)$_2$, HNC(O)S, SC(O)O, O, NH, NHC(O), (NH)$_2$C(O) (O)CNH and NHC(O)O, and OC(O)NH, CH$_2$S, CH$_2$O, CH$_2$CH$_2$O, CH$_2$CH$_2$S, (CH$_2$)$_p$O, (CH$_2$)$_p$S or (CH$_2$)$_p$Y'-PEG wherein, Y' is S, NH, NHC(O), C(O)NH, NHC(O)O, OC(O)NH, or O and p is an integer from 1 to 50. A linkage can also refer to a bond.

The acceptor-linker and functional moiety can be of any useful structure including, but not limited to, acyl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, peptide (e.g., a peptide including a protease site), nucleic acid (e.g., hybridization probes, PCR primers), saccharide (e.g., dextran, starch, cyclodextrin). In one preferred embodiment, the linker $L^{11}$ of the functional moiety is long enough to avoid side reactions during synthesis (e.g. intra-molecular reactions, such as intra-molecular peptide bond formation), to allow coupling of the compound or complex of the invention to a targeting moiety and to allow the targeting moiety to fulfill its intended function. Useful linkers include those with about 2 to about 50 linear atoms, preferably about 4 to about 20 linear atoms.

In an exemplary embodiment, the acceptor-linker is a nucleic acid and the invention provides a probe based on the nucleic acid. In an example according to this embodiment, an oligonucleotide probe is labeled with a luminescent chelate of the invention as the donor, and an organic fluorophore as the acceptor (reporter) moiety. The nucleic acid probe in a LRET pair can be a simple linear probe, i.e., neither a quencher nor a hairpin structure is necessary.

In one exemplary embodiment, the compounds of the invention are derivatized with a functional moiety. The functional moiety can, for example, be attached to one of the linker units or to one of the building blocks. When two or more functional moieties are used, each can be attached to any of the available linking sites.

The acceptor-linker and/or the functional moiety is preferably attached, so that the resulting functionalized ligand will be able to undergo formation of stable metal ion complexes. In an exemplary embodiment, the macrocyclic ligand is derivatized with a functional moiety.

Other examples of possible structures, with L and R groups defined throughout the specification, include the following:

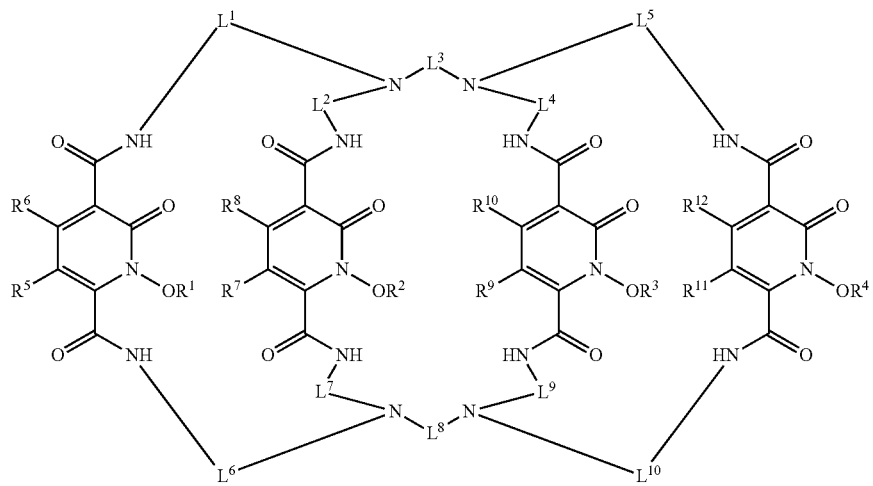

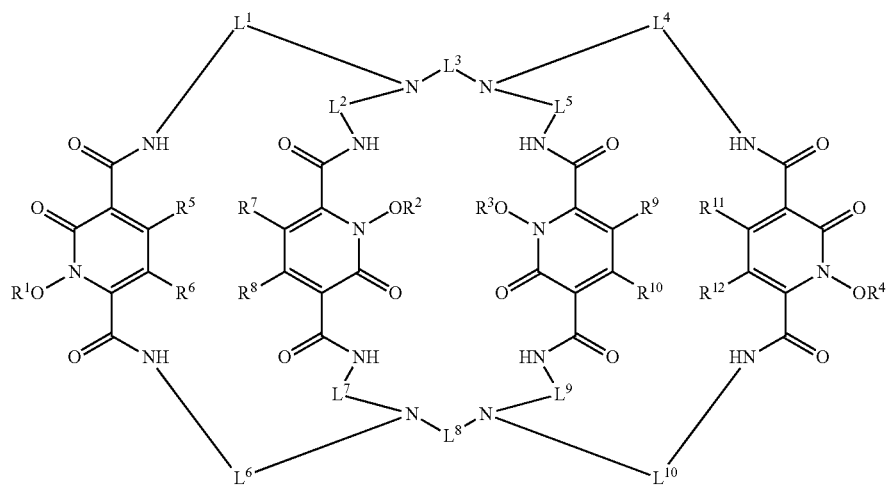

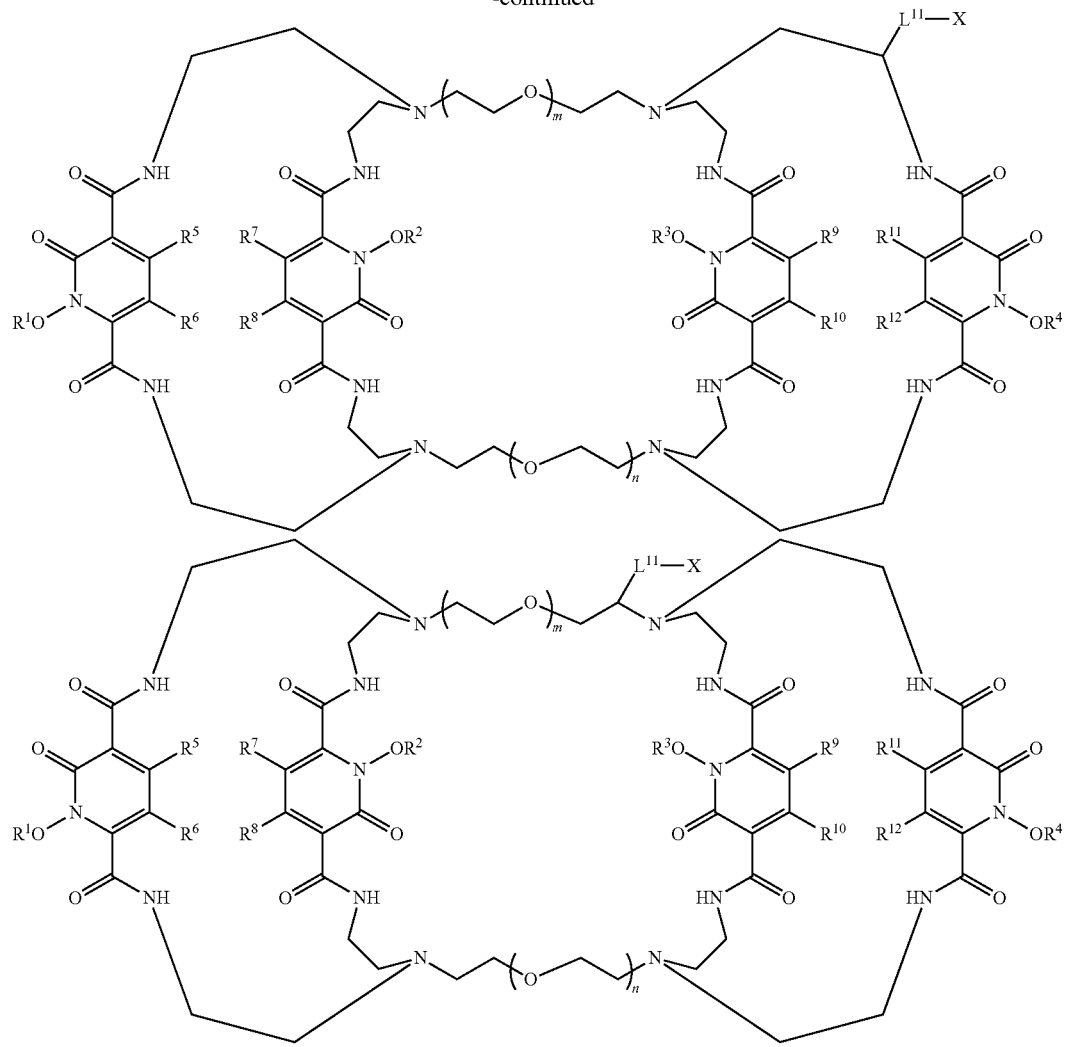

In an exemplary embodiment, a functional moiety (or acceptor-linker) has the structure:

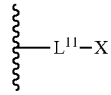

wherein $L^{11}$ is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. $L^{11}$ can be referred to as a linker moiety. X is a reactive functional group, which can be reacted with a solid support or a molecule, such as a carrier moiety or a fluorophore, thus conjugating this species to the linker through a linkage fragment. Exemplary $L^{11}$ and/or X moieties comprise —C(O)NH—, —C(O)O—, —NH—, —S—, —O—, and the like.

In some embodiments, a functional moiety may be referred to as a "pendant arm", "linking arm" or "linker arm".

Exemplary compounds of the invention include a compound according to Formula I or II, wherein the compound comprises -$L^{11}$-X having a structure selected from

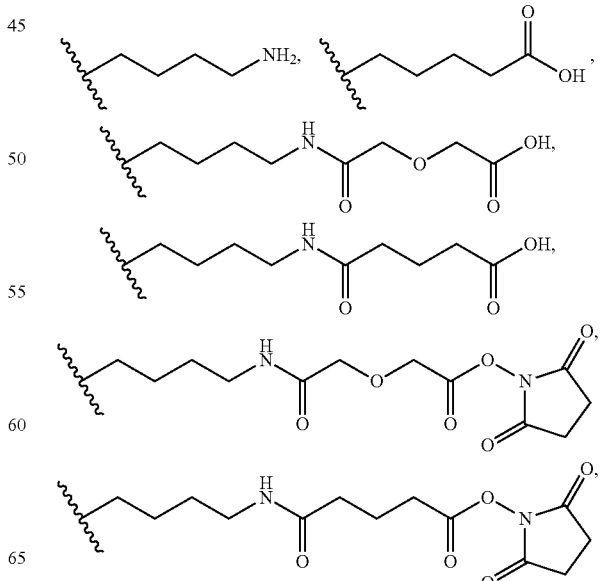

-continued

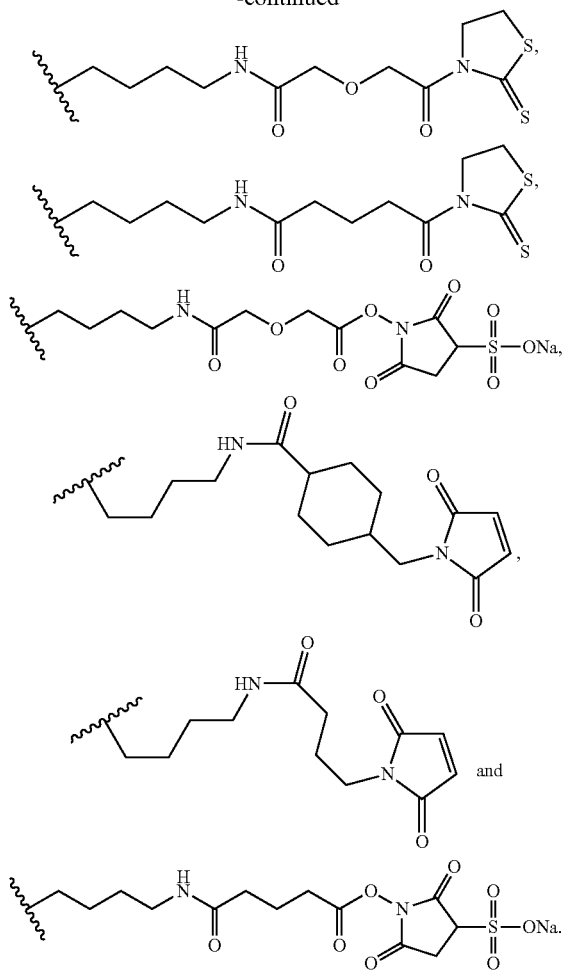

In some embodiments, -L$^{11}$-X is selected from

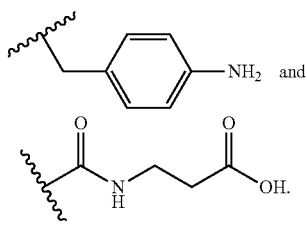

As will be apparent to those of skill in the art, the amines and carboxylic acids of the precursor compounds are readily covalently bound through a linkage fragment to one or more carrier moiety, solid support, or fluorophore.

In one embodiment, a functional moiety (e.g. -L$^{11}$-X) includes an aliphatic carbon chain or a poly-ethyleneglycol (PEG) chain. Thus, the functional moiety can be a structure selected from:

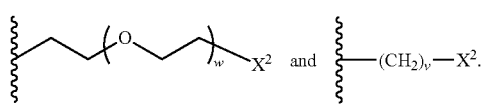

The integer v is selected from 1 to 20, and in some embodiments, from 1 to 10, 1 to 8, 1 to 6, or from 1, 2, 3 and 4. The integer w is selected from 1 to 1,000, and in some embodiments from 1 to 100, 1 to 10, or 1 to 6.

Exemplary X and X$^2$ groups can be selected from OH, alkoxy, any of the following structures:

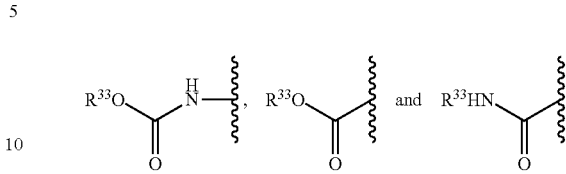

wherein R$^{33}$ is selected from H, substituted or unsubstituted alkyl, substituted or unsubstituted heteroalkyl, substituted or unsubstituted cycloalkyl, substituted or unsubstituted heterocycloalkyl substituted or unsubstituted aryl and substituted or unsubstituted heteroaryl. In some embodiments, R$^{33}$ is a member selected from H, substituted or unsubstituted alkyl, substituted or unsubstituted heteroalkyl. In some embodiments, R$^{33}$ is a member selected from H, unsubstituted alkyl and unsubstituted heteroalkyl. In some embodiments, R$^{33}$ is H. Other exemplary X and X$^2$ groups include —COOH, —NH$_2$, —NCS, —SCN,

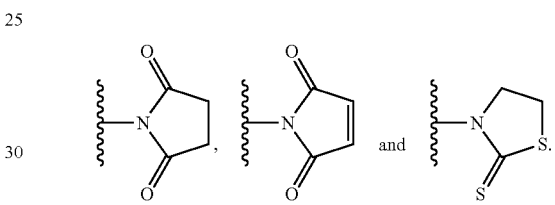

In another exemplary embodiment, a functional moiety (e.g. -L$^{11}$-X) has the structure:

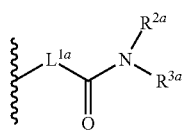

wherein L$^{1a}$ is selected from substituted or unsubstituted alkyl and substituted or unsubstituted heteroalkyl. R$^{2a}$ and R$^{3a}$ are independently selected from H, substituted or unsubstituted alkyl and substituted or unsubstituted heteroalkyl. R$^{2a}$ and R$^{3a}$, together with the nitrogen to which they are attached, are optionally joined to form a ring which is a member selected from substituted or unsubstituted 5-7 membered cycloalkyl and substituted or unsubstituted 5-7 membered heterocycloalkyl. In another exemplary embodiment, L$^{1a}$ does not comprise a carboxylic acid ester.

In another exemplary embodiment, a functional moiety has the structure:

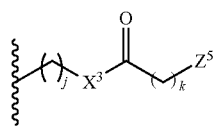

wherein Z$^5$ is selected from H, OR$^{34}$, SR$^{34}$, NHR$^{34}$, OCOR$^{35}$, OC(O)NHR$^{35}$, NHC(O)OR$^{34}$, OS(O)$_2$OR$^{34}$, and C(O)R$^{35}$. R$^{34}$ is selected from H, substituted or unsubstituted alkyl, and substituted or unsubstituted heteroalkyl. R$^{35}$ is a member selected from H, $OR^{36}$, $NR^{36}NH_2$, SH, $C(O)R^{36}$, $NR^{36}H$, substituted or unsubstituted alkyl and substituted or unsubstituted heteroalkyl. $R^{36}$ is selected from H, substituted or unsubstituted alkyl and substituted or unsubstituted alkyl. $X^3$ is a member selected from O, S and $NR^{37}$, wherein $R^{37}$ is a member selected from H, substituted or unsubstituted alkyl and substituted or unsubstituted heteroalkyl. The integers j and k are independently selected from 1, 2, 3, 4, 5, 6, 7, 8, 9, 10, 11, 12, 13, 14, 15, 16, 17, 18, 19 and 20.

Compounds according to any of the embodiments discussed herein include those in which at least one $L^x$ or $R^x$ moiety is functionalized with a acceptor-linker, optionally bound to a fluorophore, e.g., through a linkage fragment. In another embodiment, at least one of $L^x$ or $R^x$ moiety is functionalized with a functional moiety (optionally bound to a carrier moiety or solid support, e.g., through a linkage fragment). In yet another exemplary embodiment, one of these $L^x$ or $R^x$ groups is functionalized with a acceptor-linker (optionally bound to a fluorophore) and the same or a different $L^x$ or $R^x$ moiety is functionalized with a functional moiety (optionally bound to a carrier moiety or solid support).

Thus, the present invention provides compounds according to Formula I or II in which at least one $L^x$ moiety is substituted with a group selected from:

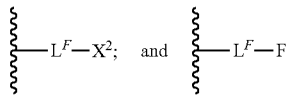

in which $L^F$ is a acceptor-linker as described herein, and $X^2$ is a reactive functional group. F is a fluorophore bound to $L^F$ through a linkage fragment formed as described herein.

In another embodiment, the invention provides compounds according to Formula I or II in which at least one $L^x$ moiety is substituted with a group selected from:

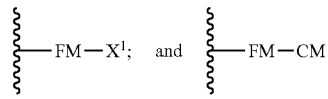

in which FM is a functional moiety as described herein, having as a component a reactive functional group, $X^1$. CM is a carrier moiety (or solid support) bound to FM through a linkage fragment formed as described herein.

In still a further embodiment, the invention provides a compound according to Formula I or II in which at least one $L^x$ moiety is substituted with a group selected from:

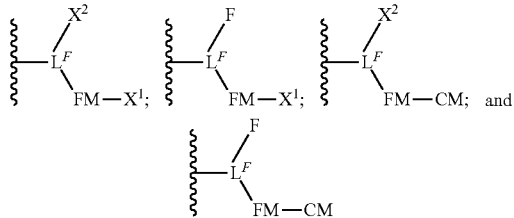

in which the moieties are as described above. As will be appreciated by those of skill in the art, rather than a fluorophore, the acceptor-linker can be conjugated to one or more quencher or other luminescence modifying moiety.

A functional moiety, such as $-L^{11}$-X can be attached to a macrocyclic chelator, for example, at an L group, according to methods known in the art. See, for example, US Patent Application Publication 2010/0015725. Thus, one way to include a functional moiety in a macrocyclic chealtor is to derivatize a capping structure or linking moiety and then to attach chelating moieties thereto.

Reactive Functional Groups

In one embodiment, the functional moiety includes a reactive functional group, which can be used to covalently attach the ligand to another species, e.g. a carrier moiety or solid support. Alternatively, the reactive functional group can be used to link the ligand to a nano-particle of any kind. Reactive groups and classes of reactions useful in practicing the present invention are generally those that are well known in the art of bioconjugate chemistry. Currently favored classes of reactions available with reactive functional groups of the invention are those which proceed under relatively mild conditions. These include, but are not limited to nucleophilic substitutions (e.g., reactions of amines and alcohols with acyl halides and activated esters), electrophilic substitutions (e.g., enamine reactions) and additions to carbon-carbon and carbon-heteroatom multiple bonds (e.g., Michael reactions and Diels-Alder reactions). These and other useful reactions are discussed, for example, in: March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

a) Amines and Amino-Reactive Groups

In one embodiment, the reactive functional group is a member selected from amines, such as a primary or secondary amine, hydrazines, hydrazides, and sulfonylhydrazides. Amines can, for example, be acylated, alkylated or oxidized. Useful non-limiting examples of amino-reactive groups include N-hydroxysuccinimide (NHS) esters, sulfur-NHS esters, imidoesters, isocyanates, isothiocyanates, acylhalides, arylazides, p-nitrophenyl esters, aldehydes, sulfonyl chlorides and carboxyl groups.

NHS esters and sulfur-NHS esters react preferentially with the primary (including aromatic) amino groups of the reaction partner. The imidazole groups of histidines are known to compete with primary amines for reaction, but the reaction products are unstable and readily hydrolyzed. The reaction involves the nucleophilic attack of an amine on the acid carboxyl of an NHS ester to form an amide, releasing the N-hydroxysuccinimide.

Imidoesters are the most specific acylating reagents for reaction with the amine groups of e.g., a protein. At a pH between 7 and 10, imidoesters react only with primary amines. Primary amines attack imidates nucleophilically to produce an intermediate that breaks down to amidine at high pH or to a new imidate at low pH. The new imidate can react with another primary amine, thus crosslinking two amino groups, a case of a putatively monofunctional imidate reacting bifunctionally. The principal product of reaction with primary amines is an amidine that is a stronger base than the original amine. The positive charge of the original amino group is therefore retained. As a result, imidoesters do not affect the overall charge of the conjugate.

Isocyanates (and isothiocyanates) react with the primary amines of the conjugate components to form stable bonds. Their reactions with sulfhydryl, imidazole, and tyrosyl groups give relatively unstable products.

Acylazides are also used as amino-specific reagents in which nucleophilic amines of the reaction partner attack acidic carboxyl groups under slightly alkaline conditions, e.g. pH 8.5.

Arylhalides such as 1,5-difluoro-2,4-dinitrobenzene react preferentially with the amino groups and tyrosine phenolic groups of the conjugate components, but also with its sulfhydryl and imidazole groups.

p-Nitrophenyl esters of carboxylic acids are also useful amino-reactive groups. Although the reagent specificity is not very high, α- and ε-amino groups appear to react most rapidly.

Aldehydes react with primary amines of the conjugate components (e.g., ε-amino group of lysine residues). Although unstable, Schiff bases are formed upon reaction of the protein amino groups with the aldehyde. Schiff bases, however, are stable, when conjugated to another double bond. The resonant interaction of both double bonds prevents hydrolysis of the Schiff linkage. Furthermore, amines at high local concentrations can attack the ethylenic double bond to form a stable Michael addition product. Alternatively, a stable bond may be formed by reductive amination.

Aromatic sulfonyl chlorides react with a variety of sites of the conjugate components, but reaction with the amino groups is the most important, resulting in a stable sulfonamide linkage.

Free carboxyl groups react with carbodiimides, soluble in both water and organic solvents, forming pseudoureas that can then couple to available amines yielding an amide linkage. Yamada et al., Biochemistry 1981, 20: 4836-4842, e.g., teach how to modify a protein with carbodiimides.

b) Sulfhydryl and Sulfhydryl-Reactive Groups

In another embodiment, the reactive functional group is a member selected from a sulfhydryl group (which can be converted to disulfides) and sulfhydryl-reactive groups. Useful non-limiting examples of sulfhydryl-reactive groups include maleimides, alkyl halides, acyl halides (including bromoacetamide or chloroacetamide), pyridyl disulfides, and thiophthalimides.

Maleimides react preferentially with the sulfhydryl group of the conjugate components to form stable thioether bonds. They also react at a much slower rate with primary amino groups and the imidazole groups of histidines. However, at pH 7 the maleimide group can be considered a sulfhydryl-specific group, since at this pH the reaction rate of simple thiols is 1000-fold greater than that of the corresponding amine.

Alkyl halides react with sulfhydryl groups, sulfides, imidazoles, and amino groups. At neutral to slightly alkaline pH, however, alkyl halides react primarily with sulfhydryl groups to form stable thioether bonds. At higher pH, reaction with amino groups is favored.

Pyridyl disulfides react with free sulfhydryl groups via disulfide exchange to give mixed disulfides. As a result, pyridyl disulfides are relatively specific sulfhydryl-reactive groups.

Thiophthalimides react with free sulfhydryl groups to also form disulfides.

c) Other Reactive Functional Groups

Other exemplary reactive functional groups include:
(a) carboxyl groups and various derivatives thereof including, but not limited to, N-hydroxybenztriazole esters, acid halides, acyl imidazoles, thioesters, p-nitrophenyl esters, alkyl, alkenyl, alkynyl, including succinic and maleic active esters and aromatic esters;
(b) hydroxyl groups, which can be converted to esters, ethers, aldehydes, etc.;
(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;
(d) dienophile groups, which are capable of participating in Diels-Alder reactions such as, for example, maleimido groups;
(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;
(f) alkenes, which can undergo, for example, cycloadditions, acylation, Michael addition, etc;
(g) epoxides, which can react with, for example, amines and hydroxyl groups;
(h) phosphoramidites and other standard functional groups useful in nucleic acid synthesis and
(i) any other functional group useful to form a covalent bond between the functionalized ligand and a molecular entity or a surface.

d) Functional Groups with Non-specific Reactivities

In addition to the use of site-specific reactive moieties, the present invention contemplates the use of non-specific reactive groups to link the ligand to a targeting moiety. Non-specific groups include activatable, such as photoactivatable groups, for example. An "activatable" group refers to any group that can be converted into a reactive species upon contact with an activator, including, for example, a chemical agent or electromagnetic radiation.

Photoactivatable groups are ideally inert in the dark and are converted to reactive species in the presence of light. In one embodiment, photoactivatable groups are selected from precursors of nitrenes generated upon heating or photolysis of azides. Electron-deficient nitrenes are extremely reactive and can react with a variety of chemical bonds including N—H, O—H, C—H, and C=C. Although three types of azides (aryl, alkyl, and acyl derivatives) may be employed, arylazides are presently preferrred. The reactivity of arylazides upon photolysis is better with N—H and O—H than C—H bonds. Electron-deficient arylnitrenes rapidly ring-expand to form dehydroazepines, which tend to react with nucleophiles, rather than form C—H insertion products. The reactivity of arylazides can be increased by the presence of electron-withdrawing substituents such as nitro or hydroxyl groups in the ring. Such substituents push the absorption maximum of arylazides to longer wavelength. Unsubstituted arylazides have an absorption maximum in the range of 260-280 nm, while hydroxy and nitroarylazides absorb significant light beyond 305 nm. Therefore, hydroxy and nitroarylazides are most preferable since they allow to employ less harmful photolysis conditions for the affinity component than unsubstituted arylazides.

In another preferred embodiment, photoactivatable groups are selected from fluorinated arylazides. The photolysis products of fluorinated arylazides are arylnitrenes, all of which undergo the characteristic reactions of this group, including C—H bond insertion, with high efficiency (Keana et al., *J. Org. Chem.* 55: 3640-3647, 1990).

In another embodiment, photoactivatable groups are selected from benzophenone residues. Benzophenone reagents generally give higher crosslinking yields than arylazide reagents.

In another embodiment, photoactivatable groups are selected from diazo compounds, which form an electron-deficient carbene upon photolysis. These carbenes undergo a variety of reactions including insertion into C—H bonds, addition to double bonds (including aromatic systems), hydrogen attraction and coordination to nucleophilic centers to give carbon ions.

In still another embodiment, photoactivatable groups are selected from diazopyruvates. For example, the p-nitrophenyl ester of p-nitrophenyl diazopyruvate reacts with aliphatic amines to give diazopyruvic acid amides that undergo ultraviolet photolysis to form aldehydes. The photolyzed diazopyruvate-modified affinity component will react like formaldehyde or glutaraldehyde forming intraprotein crosslinks.

It is well within the abilities of a person skilled in the art to select a reactive functional group, according to the reaction partner. As an example, an activated ester, such as an NHS ester will be useful to label a protein via lysine residues. Sulfhydryl reactive groups, such as maleimides can be used to label proteins via amino acid residues carrying an SH-group (e.g., cystein). Antibodies may be labeled by first oxidizing their carbohydrate moieties (e.g., with periodate) and reacting resulting aldehyde groups with a hydrazine containing ligand.

The reactive functional groups can be chosen such that they do not participate in, or interfere with, the reactions necessary to assemble the reactive ligand. Alternatively, a reactive functional group can be protected from participating in the reaction by means of a protecting group. Those of skill in the art understand how to protect a particular functional group so that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

With respect to each of the functional groups set forth above, when the functional group is on a linker, it is generally preferred that the functional group is located at a terminus of the linker. Thus, it is generally preferred that the functional group on the functional moiety and the acceptor-linker are found at a terminus of the functional moiety and the acceptor-linker, respectively.

In one embodiment, the present invention provides a composition comprising a chelate according to Formula I or II, combined with a fluorophore. The chelate and the fluorophore are preferably both linked to a carrier moiety: each can be linked to the same carrier moiety or to a different carrier moiety. It is generally preferred that the chelate be complexed with a metal ion selected such that the chelate forms an energy transfer pair with the fluorophore. In general, the metal complex will serve as the donor fluorophore, and will have a longer excited state lifetime than the acceptor fluorophore. In an exemplary embodiment, the donor fluorophore is a lanthanide chelate. In another exemplary embodiment, the acceptor fluorophore is an organic fluorophore, e.g., a polyaromatic hydrocarbon (e.g., a heterocyclic compound).

Transfer of excited state energy from the donor fluorophore to the acceptor fluorophore, provides an acceptor fluorophore with a longer excited state lifetime than and identical fluorophore that is not excited by the donor. The acceptor fluorophore generally luminesces at a wavelength longer than that of the energy incoming from the donor.

In another embodiment, the compositions of the invention include multiple donor fluorophores. In a further embodiment, the compositions of the invention include multiple acceptor fluorophores. The compositions can include both multiple donor and multiple acceptor fluorophores (or quenchers or other luminescence modifying moieties).

In an exemplary embodiment, a compound according to Formula I or II is covalently attached through the functional moiety to a carrier moiety.

In an exemplary embodiment, the compound according to Formula I or II attached to a carrier molecule or solid support is combined with a carrier moiety or solid support bound to a fluorescent species. It is generally preferred that at least one of the carrier moieties or solid supports is an assay component. An example of this embodiment is a first nucleic acid conjugated to a luminescent metal complex according to Formula I or II, which is combined in an assay with a fluorophore that is conjugated to a second nucleic acid, which is complementary to the first nucleic acid (e.g., the two hybridize under stringent conditions). Preferably, when the two nucleic acids hybridize the luminescent metal complex according to Formula I or II and the fluorophore are in operative proximity and are positioned to allow energy exchange between them (preferably from the luminescent metal complex to the fluorophore).

The luminescent complexes according to Formula I or II, in conjunction (e.g., operative contact allowing exchange of energy) with energy transfer to a fluorophore, provides a luminescent system that is tunable with respect to emission wavelength. The emission wavelength is tunable because, when energy transfer is chosen to be large, emission color is principally determined by the emission wavelength of the fluorophore, which can be selected for its output color.

The complexes in conjunction with the fluorophore are also tunable with respect to emission lifetime because the lifetime is determined by the efficiency of energy transfer from the complex of Formula I or II to the fluorophore. The fluorophore typically has a short lifetime. Because it is continuously excited by the luminescent complex of Formula I, its emission intensity decays with a lifetime related to the lifetime of the luminescent complex. The lifetime can be tuned by altering the distance between the luminescent complex and the fluorophore. The Foerster equation is of use to predict the lifetime of the energy transfer pair.

Targeting Moieties

Exemplary targeting moieties include carrier molecules as discussed herein, including small-molecule ligands, lipids, linear and cyclic peptides, polypeptides (e.g., EPO, insulin etc.), enzymes, antibodies and receptors. Other targeting moieties include antibody fragments (e.g., those generated to recognize small-molecules and receptor ligands), antigens, nucleic acids (e.g. RNA and cDNA), carbohydrate moieties (e.g., polysaccharides), and pharmacologically active molecules, such as toxins, pharmaceutical drugs and drugs of abuse (e.g. steroids). Additional targeting moieties are selected from solid supports and polymeric surfaces (e.g., polymeric beads and plastic sample reservoirs, such as plastic well-plates), sheets, fibers and membranes. Targeting moieties also include particles (e.g., nano-particles) and drug-delivery vehicles.

In one embodiment, the targeting moiety includes at least one unit of a macrocyclic compound. In an exemplary embodiment, the macrocyclic compound of the targeting moiety has a structure according to Formula I or II. In another exemplary embodiment, the compound of the invention has a dendrimeric structure and encompasses several ligands having a structure according to Formula I or II. In a further exemplary embodiment, according to this aspect, a complex based on such dendrimer includes at least two metal ions.

In one exemplary embodiment, the targeting moiety is substituted with a luminescence modifying group that allows luminescence energy transfer between a complex of the invention and the luminescence modifying group when the complex is excited.

In another exemplary embodiment, the linker moiety $L^{11}$ or the targeting moiety includes an ether or polyether, such as polyethylene glycol (PEG) and derivatives thereof. In one example, the polyether has a molecular weight between about 50 to about 10,000 daltons.

In further embodiments, the compounds and luminescent complexes of the invention can be used in any assay format aimed at detecting a lipid in a sample (e.g., in the blood of a patient). An exemplary complex according to this embodiment, includes a targeting moiety, which is a protein containing a lipid recognition motif. Exemplary lipid binding proteins include those that bind to phosphatidylinositol, phosphatidylinositol phosphates or other biological lipids.

In another example, the targeting moiety is an antibody that recognizes and binds to an analyte. In an exemplary assay system an analyte may be detected in a sample by first incubating the sample with a complex of the invention, wherein the complex is covalently bound to an antibody that includes a binding site for the analyte. To the mixture can then be added an excess of a probe molecule that binds to the same binding site as the analyte and includes a luminescence modifying group (e.g. an acceptor). The presence and concentration of analyte in the sample is indicated by the luminescence of the assay mixture. For instance, if the concentration of analyte in the sample is high, many of the antibody binding sites will be occupied with the analyte and less binding sites will be available for the probe molecule. In an exemplary embodiment, the analyte is a lipid molecule.

Complexes

The invention provides complexes formed between at least one metal ion and a compound according to Formula I or II. Exemplary complexes are luminescent, and the metal ion can be chosen according to meeting this criterion. In one exemplary embodiment, the metal is a member selected from the lanthanide group and the complex is preferably luminescent. Exemplary lanthanides include neodynium (Nd), samarium (Sm), europium (Eu), gadolinium (Gd), terbium (Tb), dysprosium (Dy) and ytterbium (Yb), of which europium and terbium are presently preferred.

The complexes of the invention may find use in applications other than those in which luminescent properties are probed. For example, it is well known that chelates of certain lanthanide ions, such as $Gd^{3+}$, are useful as contrasting agents in magnetic resonance imaging (MRI).

Fluorophore (Donor and Acceptor Moieties)

The luminescent compounds of the invention can be used with a wide range of energy donor and acceptor molecules to construct luminescence energy transfer pairs, e.g., fluorescence energy transfer (FET) probes. Fluorophores useful in conjunction with the complexes of the invention are known to those of skill in the art. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.,* 40: 83-114 (1971); Stryer, L. *Ann. Rev. Biochem.,* 47: 819-846 (1978); Wang et al., *Tetrahedron Letters* 31: 6493-6496 (1990); Wang et al., *Anal. Chem.* 67: 1197-1203 (1995).

There is practical guidance available in the literature for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970). The literature also includes references providing exhaustive lists of fluorescent and chromogenic molecules and their relevant optical properties, for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a small molecular bioactive material, nucleic acid, peptide or other polymer.

In a FRET pair, it is generally preferred that an absorbance band of the acceptor substantially overlap a fluorescence emission band of the donor. When the donor (fluorophore) is a component of a probe that utilizes fluorescence resonance energy transfer (FRET), the donor fluorescent moiety and the quencher (acceptor) of the invention are preferably selected so that the donor and acceptor moieties exhibit fluorescence resonance energy transfer when the donor moiety is excited. One factor to be considered in choosing the fluorophore-quencher pair is the efficiency of fluorescence resonance energy transfer between them. Preferably, the efficiency of FRET between the donor and acceptor moieties is at least 10%, more preferably at least 50% and even more preferably at least 80%. The efficiency of FRET can easily be empirically tested using the methods both described herein and known in the art.

The efficiency of FRET between the donor-acceptor pair can also be adjusted by changing ability of the donor and acceptor to dimerize or closely associate. If the donor and acceptor moieties are known or determined to closely associate, an increase or decrease in association can be promoted by adjusting the length of a linker moiety, or of the probe itself, between the two fluorescent entities. The ability of donor-acceptor pair to associate can be increased or decreased by tuning the hydrophobic or ionic interactions, or the steric repulsions in the probe construct. Thus, intramolecular interactions responsible for the association of the donor-acceptor pair can be enhanced or attenuated. Thus, for example, the association between the donor-acceptor pair can be increased by, for example, utilizing a donor bearing an overall negative charge and an acceptor with an overall positive charge.

In addition to fluorophores that are attached directly to a probe, the fluorophores can also be attached by indirect means. In this embodiment, a ligand molecule (e.g., biotin) is preferably covalently bound to the probe species. The ligand then binds to another molecules (e.g., streptavidin) molecule, which is either inherently detectable or covalently bound to a signal system, such as a fluorescent compound of the invention, or an enzyme that produces a fluorescent compound by conversion of a non-fluorescent compound. Useful enzymes of interest as labels include, for example, hydrolases, particularly phosphatases, esterases and glycosidases, or oxidotases, particularly peroxidases. Fluorescent compounds include fluorescein and its derivatives, rhodamine and its derivatives, dansyl, umbelliferone, etc., as discussed above. For a review of various labeling or signal producing systems that can be used, see, U.S. Pat. No. 4,391,904.

A non-limiting list of exemplary donor or acceptor moieties that can be used in conjunction with the luminescent complexes of the invention, is provided in Table 1.

TABLE 1

Suitable Moieties Useful
as Acceptors in FRET Pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
    coumarin
        7-amino-4-methylcoumarin (AMC, Coumarin 120)
        7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446

Suitable Moieties Useful
as Donors or Acceptors in FRET Pairs

Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene
    pyrene butyrate
    succinimidyl 1-pyrene butyrate
quantum dots
Reactive Red 4 (Cibacron ™ Brilliant Red 3B-A)
rhodamine and derivatives:
    6-carboxy-X-rhodamine (ROX)
    6-carboxyrhodamine (R6G)

TABLE 1-continued lissamine rhodamine B sulfonyl chloride rhodamine (Rhod)
    rhodamine B
    rhodamine 123
rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
lanthanide chelate derivatives The structure of an exemplary functionalized fluorophore of use in the compounds of the invention are set forth in FIG. 1. Similar derivatization strategies for each of the fluorophores set forth in Tables 1-3 are available and applicable to the invention.

Exemplary commercially available acceptors are listed in Table 2 including protein based acceptors and quenchers.

TABLE 2

| Acceptor Name | Excitation (nm) | Emission (nm) |
|---|---|---|
| Exemplary fluorophores | | |
| Fluorescein (FITC, FAM) | 494 | 518 |
| Eosin | 524 | |
| TET | 525 | 540 |
| HEX; JOE; VIC; CAL Fluor Orange 560 | 535 | 555 |
| ROX (5/6-carboxy Rhodamine); LC Red 610; Cal Fluor Red 610 | 575 | 605 |
| Rhodamine 101 | 496 | 520 |
| Rhodamine Red | 570 | |
| Texas Red; LC Red 610; CAL Fluor Red 610 | 590 | 610 |
| Cy2 | 489 | 506 |
| Cy3; NED; Quasar 570; Oyster 556 | 550 | 570 |
| Cy5; LC Red 670; Quasar 670; Oyster 645 | 649 | 670 |
| Malachite Green | 630 | |
| Tetramethyl Rhodamine (TAMRA, TMR, TRITC) | 555 | 580 |
| Acridine orange | 500 | 530 |
| Bodipy 530/550 | 534 | 554 |
| BODIPY TR-X | 588 | 616 |
| LC Red 640; Cal Fluor Red 635 | 625 | 640 |
| Nile Red | 485 | 525 |
| Oregon Green 488 | 493 | 520 |
| YOYO-1 | 491 | 509 |
| YOYO-2 | 612 | 631 |
| Ca-Green | 506 | 534 |
| Ca-Orange | 555 | 576 |
| Ca-Crimson | 588 | 610 |
| Mg-Green | 506 | 532 |
| Na-Green | 507 | 532 |
| Oxonol V | 610 | 639 |
| PROTEIN FLUOROPHORES | | |
| EGFP | 489 | 508 |
| dsRED | 558 | 583 |
| B-Phycoerythrin | 546, 565 | 575 |
| R-Phycoerythrin | 480, 546, 565 | 578 |
| allophycocyanin | 650 | 660 |
| FRET QUENCHERS | | |
| Quencher Name | $\epsilon$ (cm$^{-1}$M$^{-1}$) | Absorption Max (nm) |
| QSY 7 | 90,000 | 570 |
| QSY-9 | 88,000 | 562 |
| QSY-35 | 23,000 | 475 |
| BHQ-1 | | 535 |
| BHQ-2 | | 580 |
| DDQ-I | | 430 |

TABLE 2-continued

| | |
|---|---|
| Dabcyl | 475 |
| Eclipse | 530 |
| Iowa Black FQ | 532 |
| DDQ-II | 630 |
| Iowa Black RQ | 645 |

In one embodiment, the fluorophore is a member of the Alexa Fluor family, such as those set forth in Table 3.

TABLE 3

Alexa Fluor ® as Exemplary Acceptor Fluorophores for 4-Tb Donor.

| | Color[1] | Ex (nm) | Em (nm) | MW (g/mol) | $\epsilon$ (cm$^{-1}$M$^{-1}$) |
|---|---|---|---|---|---|
| Alexa Fluor 350 | blue | 346 | 442 | 410 | 19,000 |
| Alexa Fluor 405 | violet | 401 | 421 | 1028 | 34,000 |
| Alexa Fluor 430 | green | 434 | 541 | 702 | 16,000 |
| Alexa Fluor 488 | green | 495 | 519 | 643 | 71,000 |
| Alexa Fluor 500 | green | 502 | 525 | 700 | 71,000 |
| Alexa Fluor 514 | green | 517 | 542 | 714 | 80,000 |
| Alexa Fluor 532 | green | 532 | 554 | 721 | 81,000 |
| Alexa Fluor 546 | yellow-green | 556 | 573 | 1079 | 104,000 |
| Alexa Fluor 555 | green | 555 | 565 | ~1250 | 150,000 |
| Alexa Fluor 568 | orange | 578 | 603 | 792 | 91,300 |
| Alexa Fluor 594 | orange-red | 590 | 617 | 820 | 90,000 |
| Alexa Fluor 610 | red | 612 | 628 | 1172 | 138,000 |
| Alexa Fluor 633 | not vis | 632 | 647 | ~1200 | 100,000 |
| Alexa Fluor 647 | not vis | 650 | 665 | ~1300 | 239,000 |
| Alexa Fluor 660 | not vis | 663 | 690 | ~1100 | 132,000 |
| Alexa Fluor 680 | not vis | 679 | 702 | ~1150 | 184,000 |
| Alexa Fluor 700 | not vis | 702 | 723 | ~1400 | 192,000 |
| Alexa Fluor 750 | not vis | 749 | 775 | ~1300 | 240,000 |

[1]Approximate color of the emission spectrum.
$\epsilon$ = extinction coefficient Presently preferred Alexa Fluor fluorophores include 568, 594, 610, 633 and 647.

In another exemplary embodiment, the compounds of the invention emit light at an emission wavelength of the fluorophore attached to the metal chelate through the acceptor-linker. Exemplary compounds of the invention are characterized by emitting at a wavelength characteristic of the fluorophore, and the emission having a significantly enhanced lifetime.

In one embodiment, the resonance energy transfer is fluorescence resonance energy transfer (FRET), in which a first and a second probe is labeled with a donor and an acceptor moiety. When the two probes are hybridized with each other, or are each hybridized to a common target nucleic acid sequence such that the donor and acceptor are within operative proximity, energy emitted by the donor moiety is absorbed by the acceptor moiety. In a preferred embodiment, the acceptor moiety is a fluorophore that releases the energy absorbed from the donor at a different wavelength; the emissions of the acceptor may then be measured to assess the progress of the hybridization reaction. The acceptor emission may also be characterized by a different lifetime than the emission of either the donor or acceptor in the absence of the donor.

In a further exemplary embodiment, the invention provides a nucleic acid probe that includes a chelate of the invention. Preferred nucleic acid probes of the invention utilize the principle of resonance energy transfer between a donor moiety and an acceptor moiety. The donor and acceptor moiety are on the same nucleic acid or are each on a different nucleic acid. A luminescent complex of the invention is generally preferred as a donor. US/2008/0213780, incorporated by reference, discloses nucleic acid probes, methods of their use and other methods that may be applicable to the compounds and methods of the present invention.

Means of detecting fluorescent labels are well known to those of skill in the art. Thus, for example, fluorescent labels can be detected by exciting the fluorophore with the appropriate wavelength of light and detecting the resulting fluorescence. The fluorescence can be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product.

Methods

The compounds and complexes of the invention are useful as probes in a variety of biological assay systems and diagnostic applications. An overview of assay systems, such as competitive assay formats, immunological assays, microarrays, membrane binding assays and enzyme activity assays, is given e.g., in U.S. Pat. No. 6,864,103 to Raymond et al., which is incorporated herein in its entirety for all purposes. It is within the ability of one of skill in the art to select and prepare a probe that includes a complex of the invention, and which is suitable for each assay system. In an exemplary embodiment, the luminescent probe molecule is used to detect the presence or absence of an analyte in a sample.

In one embodiment, the complex according to Formula I or II is utilized in a procedure wherein emission from the complex excites at least one fluorophore in an assay. In another exemplary embodiment, emission from the complex excites at least two fluorophores in an assay, such that each fluorophore emits light of a characteristic wavelength and lifetime. In this example, each of the at least two fluorophores is distinguishable from the other on the basis of emission wavelength and/or lifetime. See, for example, Chen et al., J. Am. Chem. Soc., 122: 657-660 (2000). In one embodiment, the complex of the invention distinguishably excites at least 2, 3, 4, 5, 6, 7, 8, 9 or at least 10 fluorophores essentially simultaneously.

The disclosed lanthanide complexes have particular utility in assays that are intended to detect or quantify binding or other modification of an assay component. These assays may incorporate one or more steps, including (a) contacting at least one member of a plurality of molecules with a binding partner capable of binding one of the molecules, (b) detecting a response indicative of the extent of binding between the at least one member of the plurality and the binding partner, and (c) correlating the response with the extent of binding or modification, or with a the activity of an enzyme that affects the modification. In some embodiments, the assays may include repeating the steps of contacting, detecting, and/or correlating for the same sample and/or a plurality of different samples. The assays may also involve providing a sample holder having a plurality of sample sites containing or supporting a corresponding plurality of samples, and sequentially and/or simultaneously repeating the steps of contacting, detecting, and/or correlating for the plurality of samples. The remainder of this section describes in more detail the steps of (a) contacting, (b) detecting, and (c) correlating.

The step of contacting assay components such as binding partners (e.g., nucleic acids, peptides, enzymes, enzyme modulators, substrates, products) with one another and/or with other species generally comprises any method for bringing any specified combination of these components into functional and/or reactive contact. A preferred method is by mixing and/or forming the materials in solution, although other methods, such as attaching one or more components (e.g., a complex according to Formula I or II, a species comprising a complex according to Formula I or II or other assay component) to a bead or surface, also may be used, as long as the components retain at least some function, specificity, and/or binding affinity following such attachment. The assay may be carried out in a device for manipulating fluids. Useful assay apparati having fluidics capability (e.g., microfluidics) suitable for contacting or otherwise preparing assay components are generally known in the art.

One or more of the assay components may comprise a sample, which typically takes the form of a solution containing one or more analyte that are biological and/or synthetic in origin. The sample may be a biological sample that is prepared from a blood sample, a urine sample, a swipe, or a smear, among others. Alternatively, the sample may be an environmental sample that is prepared from an air sample, a water sample, or a soil sample, among others. The sample typically is aqueous but may contain compatible organic solvents, buffering agents, inorganic salts, and/or other components known in the art for assay solutions.

The assay components and/or sample may be supported for contact and/or detection and/or analysis by any substrate or material capable of providing such support. Suitable substrates may include microplates, PCR plates, biochips, and hybridization chambers, among others, where features such as microplate wells and microarray (i.e., biochip) sites may comprise assay sites. Microplates may include 96, 384, 1536, or other numbers of wells. These microplates also may include wells having small ($\approx$50 μL) volumes, elevated bottoms, and/or frusto-conical shapes capable of matching a sensed volume. Suitable PCR plates may include the same (or a similar) footprint, well spacing, and well shape as the preferred microplates, while possessing stiffness adequate for automated handling and thermal stability adequate for PCR. Suitable microarrays include nucleic acid and polypeptide microarrays, which are generally known in the art.

The step of detecting a response indicative of the extent of binding or modification generally comprises any method for effectuating such detection, including detecting and/or quantifying a change in, or an occurrence of, a suitable parameter and/or signal. The method may include luminescence and/or nonluminescence methods, and heterogeneous and/or homogeneous methods, among others.

Luminescence and nonluminescence methods may be distinguished by whether they involve detection of light emitted by a component of the sample. Luminescence assays involve detecting light emitted by a luminescent compound (or luminophore) and using properties of that light to understand properties of the compound and its environment. A typical luminescence assay may involve (1) exposing a sample to a condition capable of inducing luminescence from the sample, and (2) measuring a detectable luminescence response indicative of the extent of binding between the member of interest and a corresponding binding partner. Suitable luminescence assays include, among others, (1) luminescence intensity, which involves detection of the intensity of luminescence, (2) luminescence polarization, which involves detection of the polarization of light emitted in response to excitation by polarized light, (3) luminescence energy transfer, and (4) luminescence lifetime. A single assay mixture may be analyzed by one or more of these techniques. In a preferred embodiment, energy exchange between a luminescent complex of the invention and a fluorophore is utilized to detect the analyte (and optionally its degree of modification or binding to a binding partner) is utilized to determine both the emission wavelength and excitation lifetime of one or more fluorophores.

The detectable luminescence response generally comprises a change in, or an occurrence of, a luminescence signal that is detectable by direct visual observation and/or by suitable instrumentation. Typically, the detectable response is a change in a property of the luminescence, such as a change in the intensity, polarization, energy transfer, lifetime, and/or excitation or emission wavelength distribution of the luminescence. For example, energy transfer may be measured as a decrease in donor luminescence, an increase (often from zero) in acceptor luminescence, and/or a decrease in donor luminescence lifetime, among others. The detectable response may be simply detected, or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence assays, the detectable response may be generated directly using a donor or acceptor associated with an assay component actually involved in binding, or indirectly using a donor or acceptor associated with another (e.g., reporter or indicator) component. Suitable methods and donors and acceptors for luminescently labeling assay components are described in the following materials, which are incorporated herein by reference: Richard P. Haugland, Handbook of Fluorescent Probes and Research Chemicals (6th ed. 1996).

Heterogeneous and homogeneous methods may be distinguished by whether they involve sample separation before detection. Heterogeneous methods generally require bulk separation of bound and unbound species. This separation may be accomplished, for example, by washing away any unbound species following capture of the bound species on a solid phase, such as a bead or microplate surface labeled with a trivalent metal or other suitable binding partner. Such metals may include gallium (Ga), (including Ga(III)), iron (Fe), aluminum (Al), and/or zinc (Zn), among others. Suitable metals and other binding partners are described in more detail in US/2004/0249586, which is incorporated herein by reference. The extent of binding then can be determined directly by measuring the amount of captured bound species and/or indirectly by measuring the amount of uncaptured unbound species (if the total amount is known). Homogeneous methods, in contrast, generally do not require bulk separation but instead require a detectable response such as a luminescence response that is affected in some way by binding or unbinding of bound and unbound species without separating the bound and unbound species. Alternatively, or in addition, enzyme activity may result in increased or decreased energy transfer between a donor and acceptor of an energy transfer pair, based on whether the acceptor quenches or not, and based on whether enzyme activity in the assay results in increased or decreased proximity of the donor and acceptor. Homogeneous assays typically are simpler to perform but more complicated to develop than heterogeneous assays.

The step of correlating generally comprises any method for correlating the extent of binding with the extent of modification of the assay component being analyzed, and/or with the presence and/or activity of an enzyme that affects the modification. The nature of this step depends in part on whether the detectable response is simply detected or whether it is quantified. If the response is simply detected, it typically will be used to evaluate the presence of a component such as a substrate, product, and/or enzyme, or the presence of an activity such as an enzyme or modulator activity. In contrast, if the response is quantified, it typically will be used to evaluate the presence and/or quantity of a component such as a substrate, product, and/or enzyme, or the presence and/or activity of a component such as an enzyme or modulator.

The correlation generally may be performed by comparing the presence and/or magnitude of the response to another response (e.g., derived from a similar measurement of the same sample at a different time and/or another sample at any time) and/or a calibration standard (e.g., derived from a calibration curve, a calculation of an expected response, and/or a luminescent reference material). Thus, for example, in a energy transfer assay for cyclic nucleotide concentration, the cyclic nucleotide concentration in an unknown sample may be determined by matching the energy transfer efficiency measured for the unknown with the cyclic nucleotide concentration corresponding to that efficiency in a calibration curve generated under similar conditions by measuring energy transfer efficiency as a function of cyclic nucleotide concentration.

Thus, in one aspect, the invention provides a mixture of a complex of the invention and an analyte.

In another aspect, the invention provides a method of detecting the presence or absence of an analyte in a sample. The method comprises (a) contacting the sample and a composition including a complex of the invention; (b) exciting the complex; and (c) detecting luminescence from the complex. The presence or absence of the analyte can be indicated by the absence or presence of luminescence from the complex.

In a further aspect, the invention provides a method of detecting the presence or absence of an analyte in a sample. The method comprises (a) contacting the sample and a composition comprising a complex of the invention, and a luminescence modifying group, wherein energy can be transferred between the complex and the luminescence modifying group when the complex is excited, and wherein the complex and the luminescence modifying group can be part of the same molecule or be part of different molecules; and (b) exciting said complex; and (c) determining the luminescent property of the sample, wherein the presence or absence of the analyte is indicated by the luminescent property of the sample.

In one embodiment, the analyte, if present in said sample, competes with a probe molecule that includes a complex of the invention, for binding to a binding site located on a recognition molecule. In another embodiment, the analyte displaces the probe molecule from the binding site located on a recognition molecule, by binding to the binding site. In a further embodiment, the probe molecule is a complex of the invention.

Peptides doubly tagged with fluorescent dyes (*Biophys. Chem.* 67 (1997), 167-176) have previously been used as fluorogenic substrates for proteinases. In these assays dye-to-dye contact diminishes the fluorescence of the participating dyes by quenching. On enzymatic cleavage of the peptide link, the dye-tagged products dissociate, breaking dye to dye contact, thus relieving quenching of the fluorescence. To observe the increase in fluorescence indicative of enzyme activity usually requires breaking of a covalent bond in the linker. Fluorescent quenching has been used (*Analytical Biochemistry* 165 (1987) 96-101) to measure the distance between a quencher and a fluorophore when attached to a peptide linker. Ai-Ping Wei et al (WO/1995/003429) uses antibody-antigen reaction to break dye-to-dye contact in order that molecules in the dimer state (fluorescence quenched) become monomeric (fluorescence unquenched) to relieve quenching. This was used to form assays measuring specific antibodies to a recognized peptidic epitope that linked the two dyes. In common with many other homogeneous dequenching assays, while this method can measure antibodies specific to the epitope (used to bind the dyes) in a noncompetitive manner, its adaptation to measuring other analytes, possible only in competitive mode, suffers from disadvantage in that the fluorescence signal becomes indirectly proportional to analyte concentration.

Hence, in one aspect, the invention provides a kit including a recognition molecule and a compound or a complex of the invention. Exemplary recognition molecules include biomolecules, such as whole cells, cell-membrane preparations, antibodies, antibody fragments, proteins (e.g., cell-surface receptors, such as G-protein coupled receptors), protein domains, peptides, nucleic acids, and the like.

In exemplary embodiments, a method of detecting an analyte comprises performing a sandwich immunoassay. The basic format for the sandwich immunoassay is well known in the art. Generally, a capture ligand, which is selective for binding to a particular analyte, is attached to a support (e.g., a bead). The capture ligand is then contacted with a sample, which could contain an analyte of interest. After selective binding of the analyte to the capture ligand, a detection ligand binds with the analyte, forming an analyte complex. The detection ligand will typically comprise a label.

In exemplary embodiments, the capture ligand and detection ligand are each an antibody. In exemplary embodiments, the support is a bead that comprises one or more luminescent complexes according to the invention. Where more than one luminescent complex is part of the bead, the ratios of the different complexes may vary. In exemplary embodiments, the support is a bead comprising a first luminescent complex comprising Eu and a second luminescent complex comprising Tb. In exemplary embodiments, the detection ligand comprises a label such as a fluorophore. In exemplary embodiments, one or more luminescent complexes of a bead is excited, and energy is transferred to the label of a detection ligand. Energy emission from the label can then be detected to give an indication of analyte binding.

In one aspect, the invention provides a composition comprising (a) a first bead comprising (i) a first capture ligand, (ii) a first luminescent complex and (iii) a second luminescent complex; and (b) a second bead comprising (i) a second capture ligand, (ii) a third luminescent complex and (iii) a fourth luminescent complex. In these embodiments, the first capture ligand will be different from the second capture ligand. Also, the ratio of the first and the second luminescent complex will be different from the ratio of the third and the fourth luminescent complex. In some embodiments, the first and the third luminescent complex are the same. In some embodiments, the second and the fourth luminescent complex are the same. In some embodiments, the second and/or fourth luminescent complex is absent.

In exemplary embodiments, time resolved flow cytometry can be used to detect the binding of an analyte.

In one aspect, the invention provides a method of detecting the presence or absence of an analyte in a sample. The method comprises (a) combining the sample and a composition including a luminescent complex of the invention; (b) exciting the complex; and (c) detecting luminescence (e.g., fluorescence) from the complex. In one example, the presence or absence of the analyte is indicated by the presence or absence of luminescence from the complex. In an exemplary embodiment, the excited complex transfers energy to a fluorophore other than the complex and luminescence from the excited fluorophore is detected and indicates the presence or absence of an analyte in the sample. The analyte can be quantitated by quantitating the luminescence from the complex or the fluorophore. The fluorophore can also serve as a quencher or other luminescence modifying group, alternatively, the acceptor-linker can be conjugated to a non-fluorescent quencher or other luminescence modifying moiety that forms an energy transfer pair with a luminescent complex of the invention.

In one aspect, the invention provides a method of detecting the presence or absence of an analyte in a sample. The method includes (a) combining the sample and a composition including a luminescent complex of the invention, and a luminescence modifying group, wherein energy can be transferred between the complex and the luminescence modifying group when the complex is excited, and wherein the complex and the luminescence modifying group can be part of the same molecule or part of different molecules; and (b) exciting the complex; and (c) determining a luminescent property of the sample, wherein the presence or absence of the analyte is indicated by the luminescent property of the sample. In one example, the presence or absence of the analyte in the sample is indicated by a change in the luminescent property of the sample (e.g., change in lifetime, change in emission wavelength, change in amount of luminescence). The amount of analyte in the sample can be quantitated by quantitating the luminescent property or the change in the luminescent property.

Analytes

The compounds, complexes and methods of the invention can be used to detect any analyte or class of analytes in any sample. A sample may contain e.g., a biological fluid (e.g., blood of a patient) or tissue. Other samples can e.g., include solutions of synthetic molecules or extracts from a plant or microorganism (e.g., for drug screening efforts). Exemplary analytes are pharmaceutical drugs, drugs of abuse, synthetic small molecules, biological marker compounds, hormones, infectious agents, toxins, antibodies, proteins, lipids, organic and inorganic ions, carbohydrates and the like. (see, e.g., U.S. Pat. No. 6,864,103 to Raymond et al. for additional examples of analytes).

Synthesis

The compounds and complexes of the invention are synthesized by an appropriate combination of generally well-known synthetic methods. Techniques useful in synthesizing the compounds of the invention are both readily apparent and accessible to those of skill in the relevant art. The discussion below is offered to illustrate certain of the diverse methods available for use in assembling the compounds of the invention, it is not intended to limit the scope of reactions or reaction sequences that are useful in preparing the compounds of the present invention.

One multistep synthetic route is shown in Scheme 1.

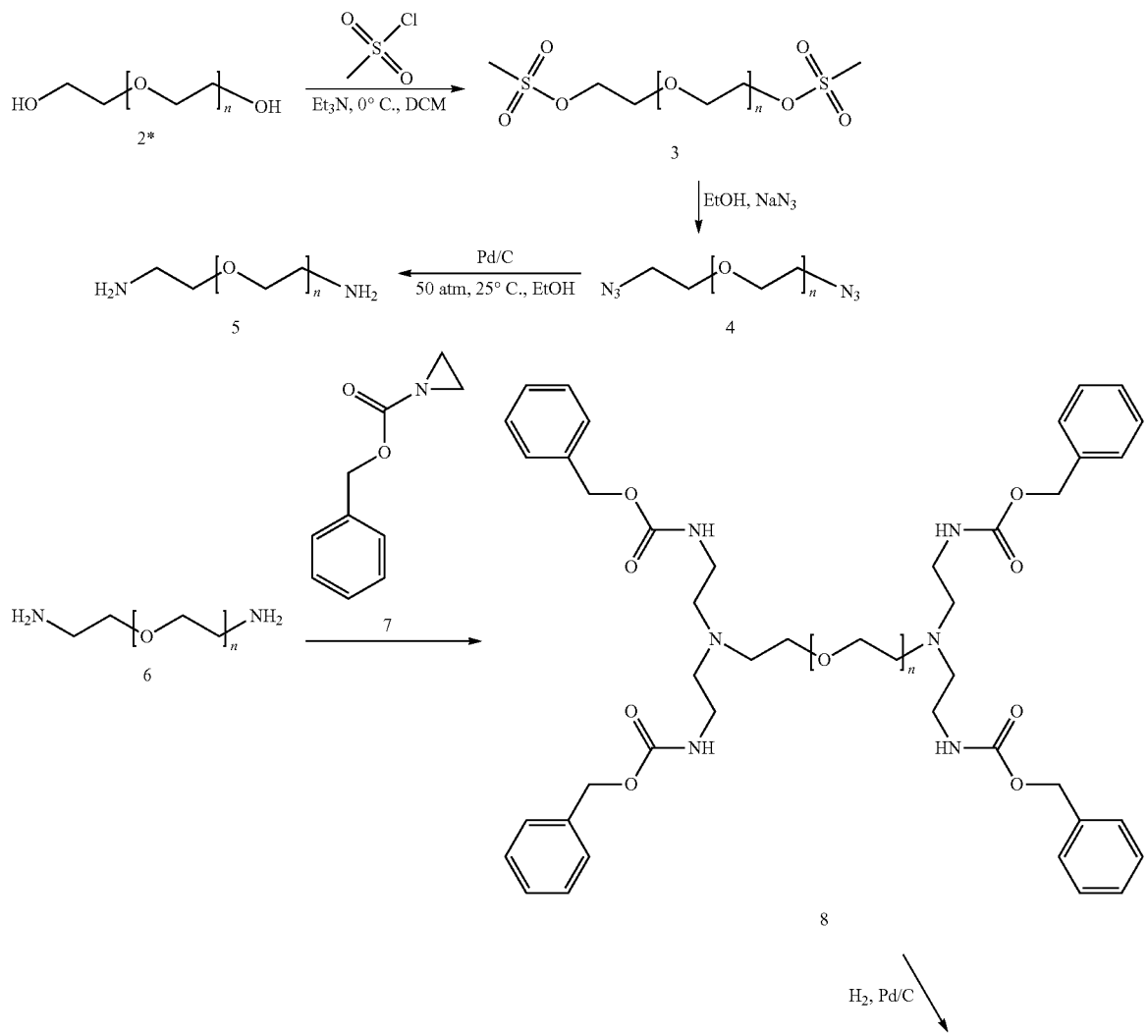

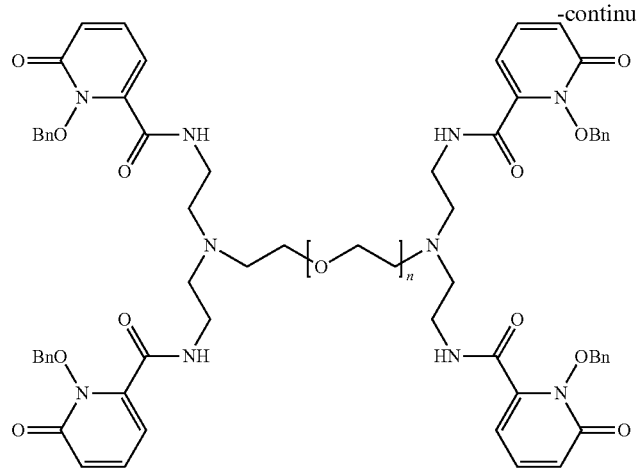

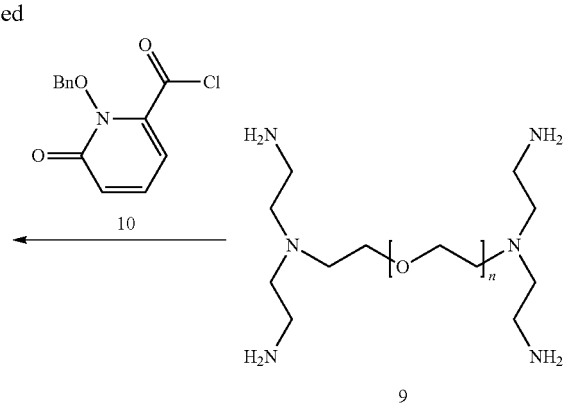

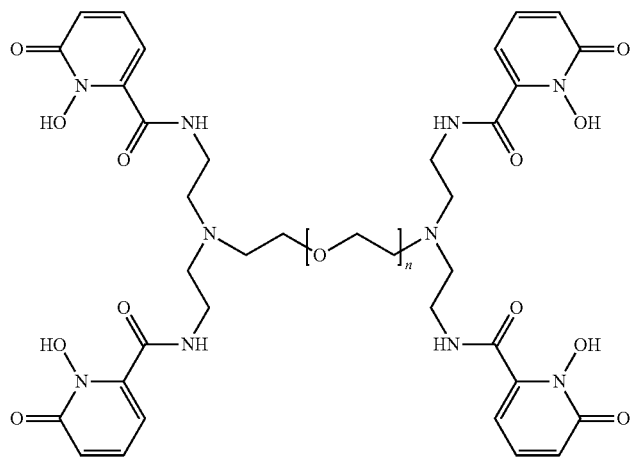

n = 1: H5-1 (1a)
2: H8-2 (1b)
3: H11-3 (1c)
4: H14-4 (1d)
5: H17-5 (1e)
6: H20-6 (1f)
7: H23-7 (1g)

The reagent pentaethyleneglycol 2 is combined with mesylate chloride to afford 3. The mesylate derivative is transformed into the diazide 4 by reaction with sodium azide in ethanol. The diamine 5 is prepared by hydrogenation on Pd/C catalyst.

For the PEG containing ligand, the protected tetrakis amine derivatives are made by reacting the appropriate bis amine molecules (5d, 5e, 5f, 5g) with carbobenzoyl aziridine (7). Subsequently, the protected tetrakis amine (8) is deprotected by hydrogenation, giving 9 in good yield. Reaction of either backbone with the activated 1,2-HOPO precursor [6, 51] yields the benzyl-protected ligands (11), which will be deprotected under acidic conditions with AcOH/HCl to yield 1d-1g. The compounds H14-4 (1d) through H23-7 (1g) can be characterized below including UV/Visible absorption and emission profiles, fluorescent quantum yield, and extinction coefficient.

The methodology for stabilizing Tb chelate Lumi-4-Tb (12, linking arm not shown) could be used to stabilize a backbone optimized 1,2-HOPO Eu chelate (13)

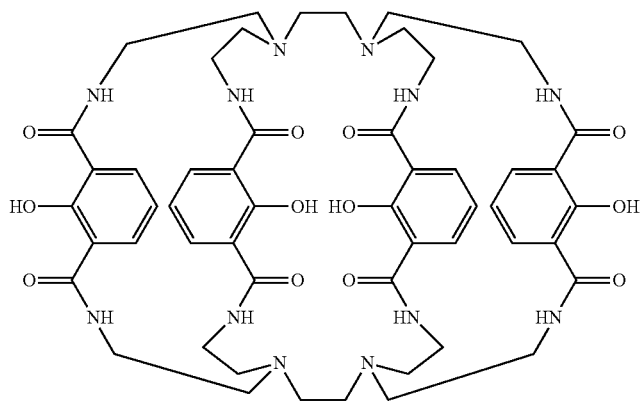
12
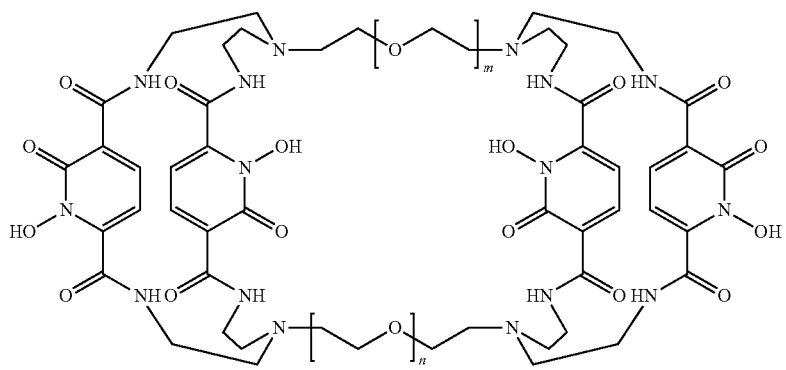
13
Scheme 2 shows one strategy for synthesizing macrocyclic structures.

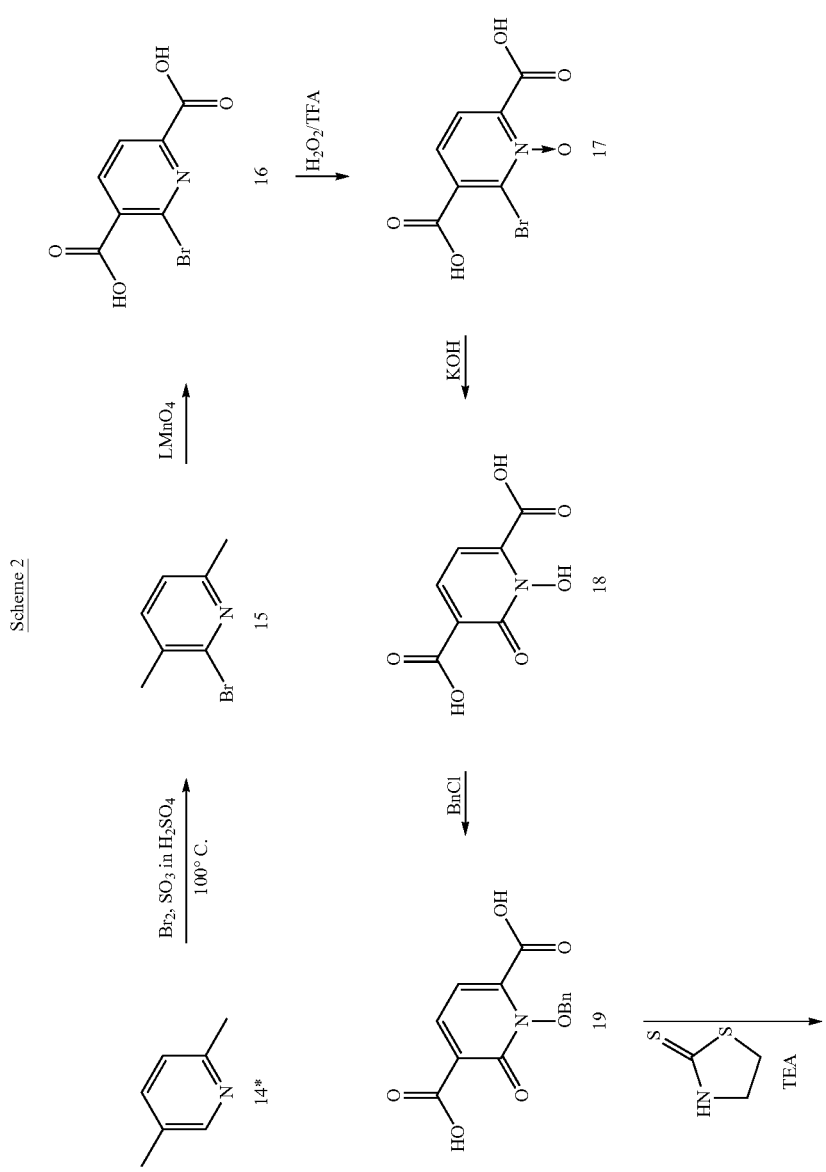

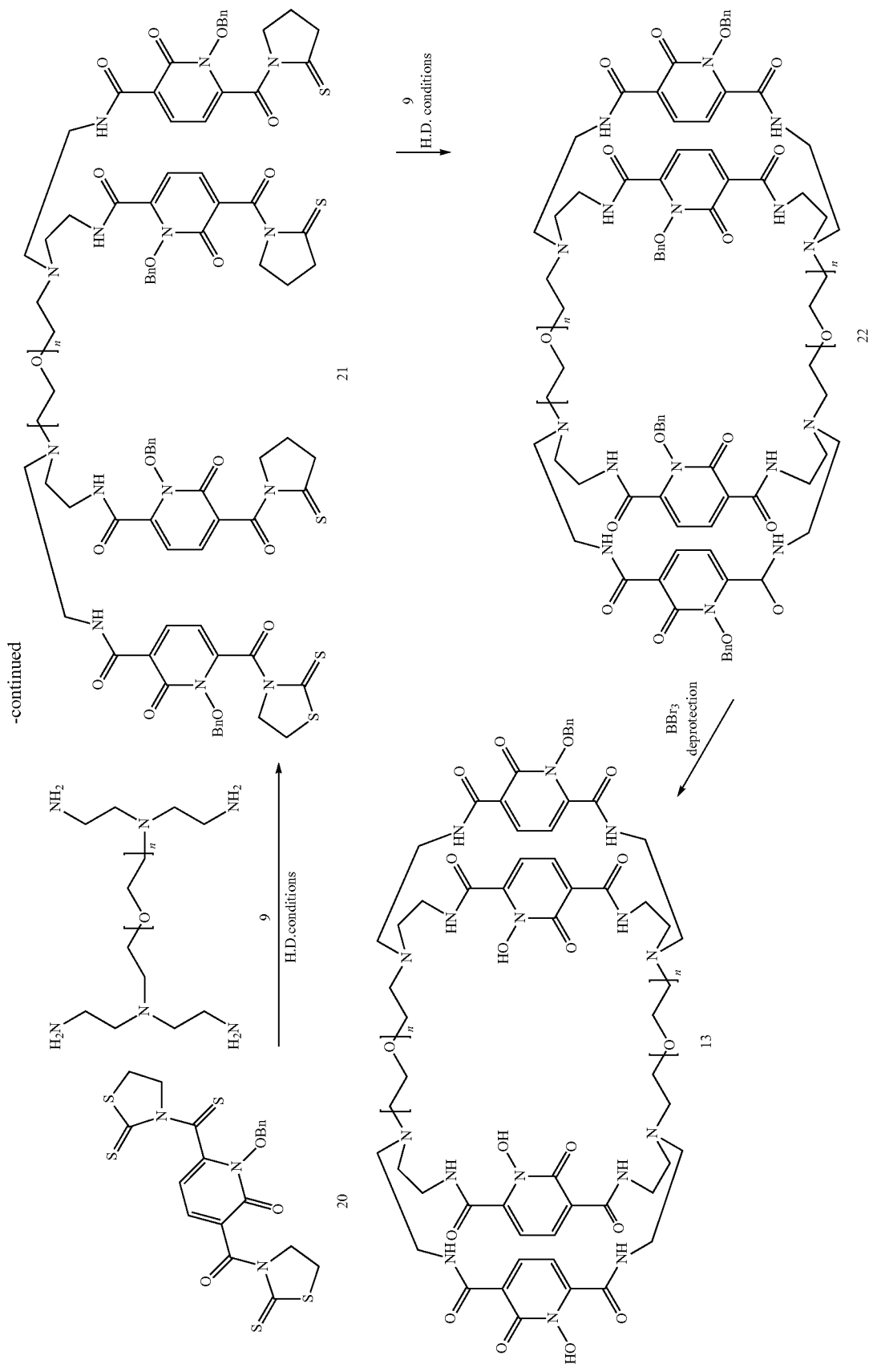

2,5-dimethylpyridine (14) is brominated at the 5 position (15) and oxidized with permanganate to form 2,4-dicarboxy-5-bromopyridine (16). Oxidation to the pyridine N-oxide (17) with peroxide/TFA and subsequent oxidation with KOH will yield 18. Protection with benzyl chloride yields 19 which is activated with 2-thioxo-1,3-thiazolidine yielding 20. High dilution conditions are required to avoid polymerization, whereby the desired backbone (9) that was described earlier (Scheme 1) is delivered slowly over many hours to a prepared solution of 20, yielding compound 21. Following purification, this process is repeated in a similar fashion resulting in 22, followed by BBr$_3$ deprotection yielding the desired product 13(d-g).

Capping structures may in some cases be asymmetric. The synthetic approaches for these asymmetric compounds are simple substitutions in the scheme shown in Scheme 2. In this scheme, there are two steps in which high dilution conditions are required and compound 9 is added to form either the top backbone (first instance) or the bottom capping structure. By utilizing compound 9d in the first step, but compound 9e in the second, an asymmetric cryptate is prepared with a 14 atom 'top' and a 17 atom cap (see Scheme 1 for backbone nomenclature). Compounds 23 and 24 (below) are examples of asymmetric cryptates according to the invention, wherein m and n are independently any integer. Exemplary values of m and n are selected from 0-9, and in exemplary embodiments, at least one of m and n are not 0.

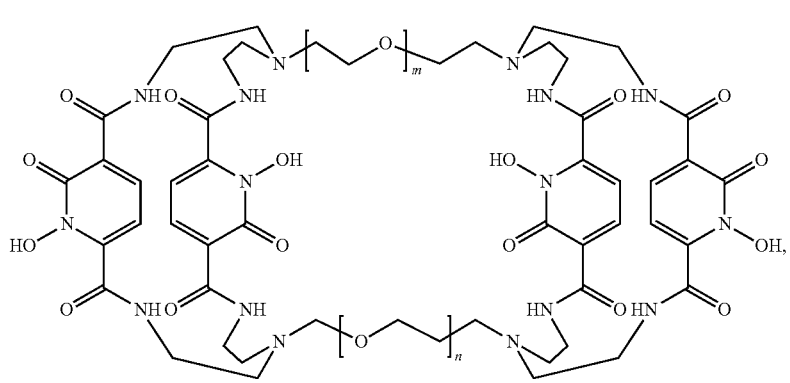

23

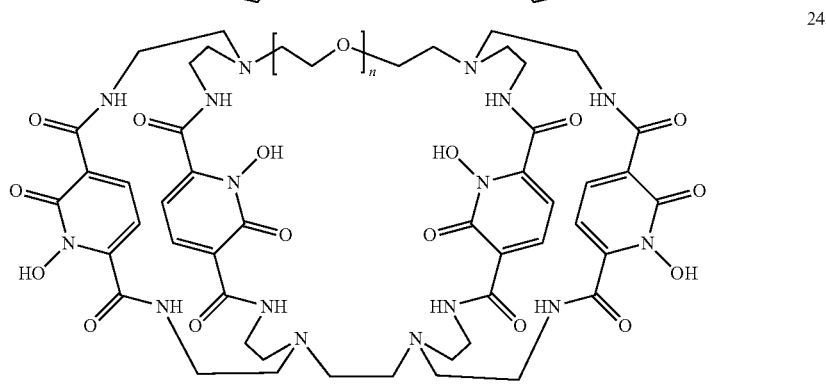

24

The chelates described herein may contain various reactive groups for covalent attachment with, for example, a carrier, a biomolecule, a solid support or for further targeting modification. 1,2-HOPO stabilized cryptates with a pendant arm is proposed in a three-step synthesis whereby compounds 27 and 32 are prepared independently, then brought together in a final synthetic effort (Scheme 3). Briefly, orthogonally protected lysine available commercially, is reduced from the carboxy form to the alcohol (26) then partially oxidized to the aldehyde (27) as shown in Scheme 3.

Scheme 3

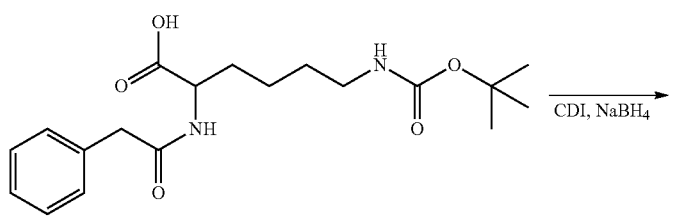

25

-continued
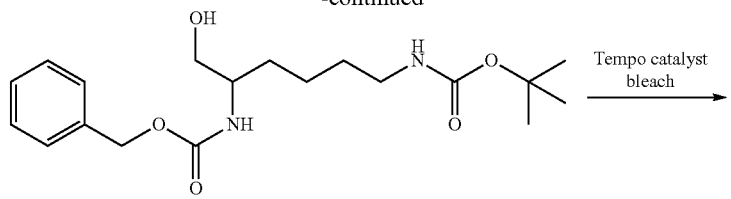
26
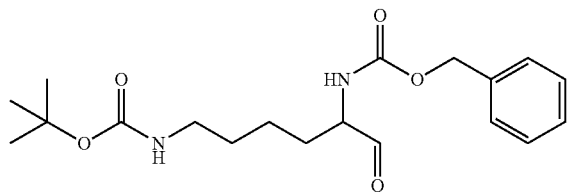
27
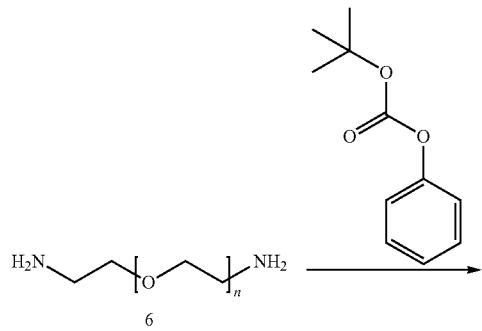
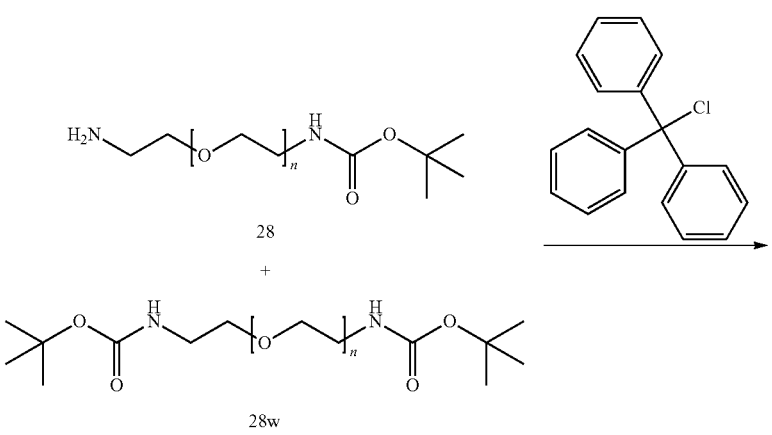
28
+
28w

-continued
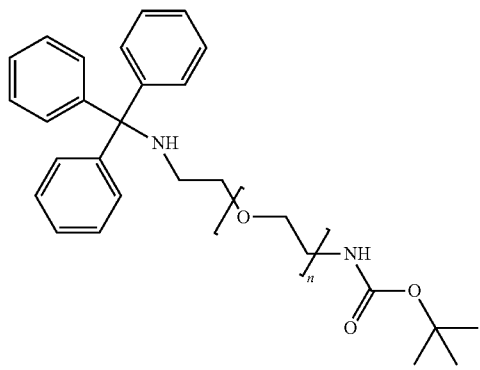
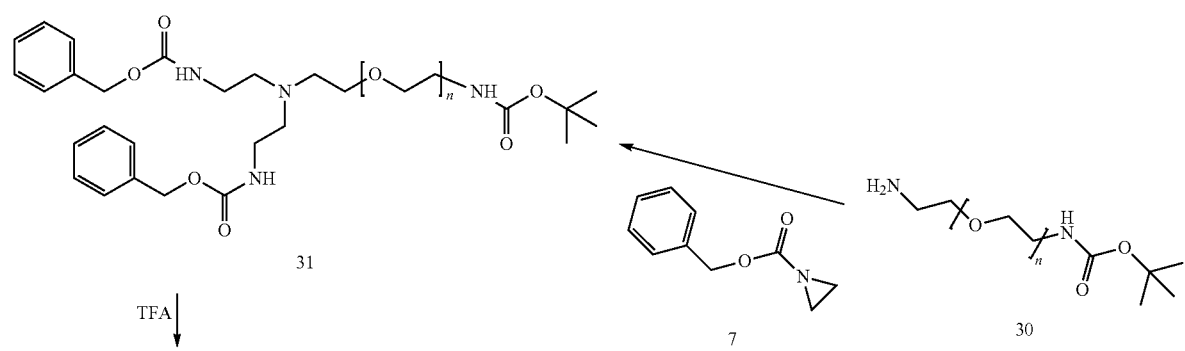
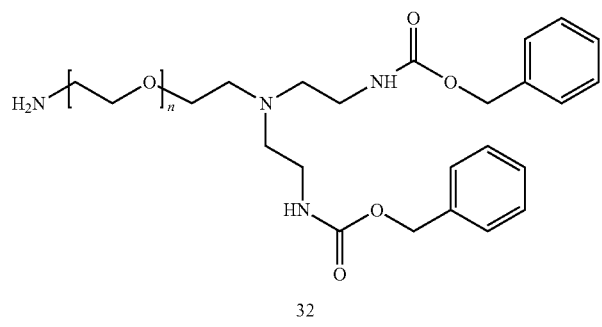

-continued
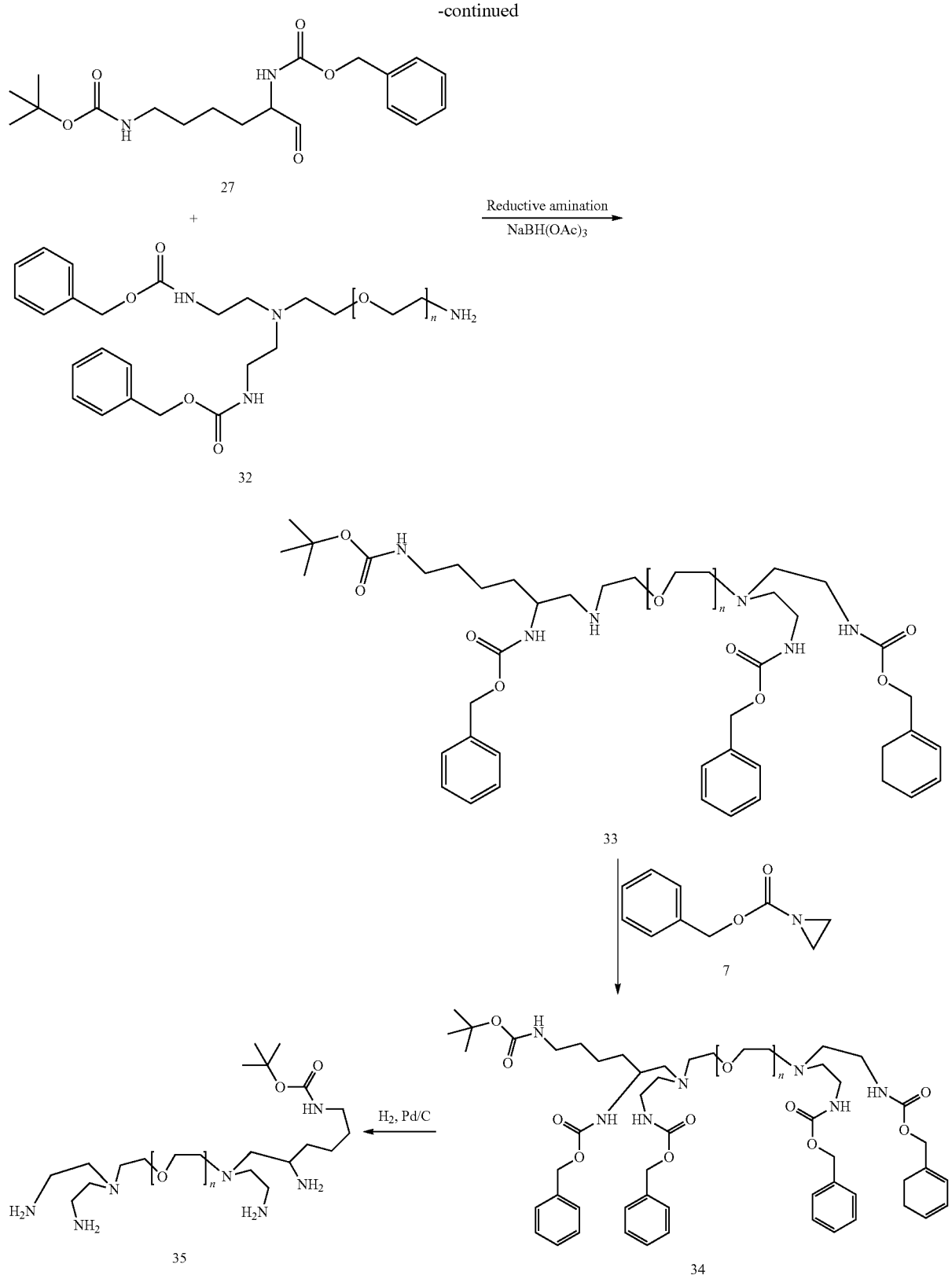
Preparation of compound 32 is more elaborate, starting with the diamine PEG described earlier (6) which is selectively protected with limiting amounts of t-butyl phenyl carbonate resulting in a mixture of 28 and 28w. In order to effectively separate the desired material (28) from the side-product (28w), the mono-protected amine can be derivatized with trityl chloride (29) and purified on silca gel. Following hydrogenation to yield 30, alkylation with 1-benzylaziridine yields 31 and 32 (following TFA deprotection).

Compounds 32 and 27 are combined under reductive amination conditions resulting in compound 33. Subsequent alkylation with 7 and hydrogenation will yield 34 and 35 respectively. Compound 35 represents a capping/backbone agent that can be substituted into the synthesis described (in place of one instance of compound 9) to yield a pendant-arm functionalized cryptate.

A primary amine functionalized linking arm is one exemplary starting point for the building of a variety of reactive groups suitable for biomolecule conjugation. The amine terminated linker (36) is derivatized into a carboxylate terminated linker (37) utilizing glutaric anhydride activated with N-hydroxysuccinimide (NHS). In compounds 36 and 37, the indices n in each compound is independently selected from 0-9, and in exemplary embodiments, at least one n is not 0.

The luminescent compounds of the invention can be coupled to representative proteins such as IgG, BSA, HSA and streptavidin and thoroughly evaluated spectroscopic and stability performance, as outlined below. Carboxylate terminated linkers are easily activated using EDC (1-Ethyl-3-[3-dimethylaminopropyl]carbodiimide) and converted to the NHS(N-hydroxysuccinimide) ester in-situ prior to coupling with primary amines present on proteins. This ester can also be stored desiccated at reduced temperature for extended periods of time. Protein coupling requires the solubilization of the NHS ester in an anhydrous solvent such as DMF and subsequent addition to a protein solution with amine-free buffer (such as carbonate) at approximately pH=9.0. Gel filtration is then performed to remove excess small molecule and exchange the protein into a more neutral pH buffer. This type of coupling is standard practice [52].

Labeling a protein with a synthetic organic reporter molecule changes the surface of that protein by replacing surface accessible primary amines (for NHS or isothiocyanate label-

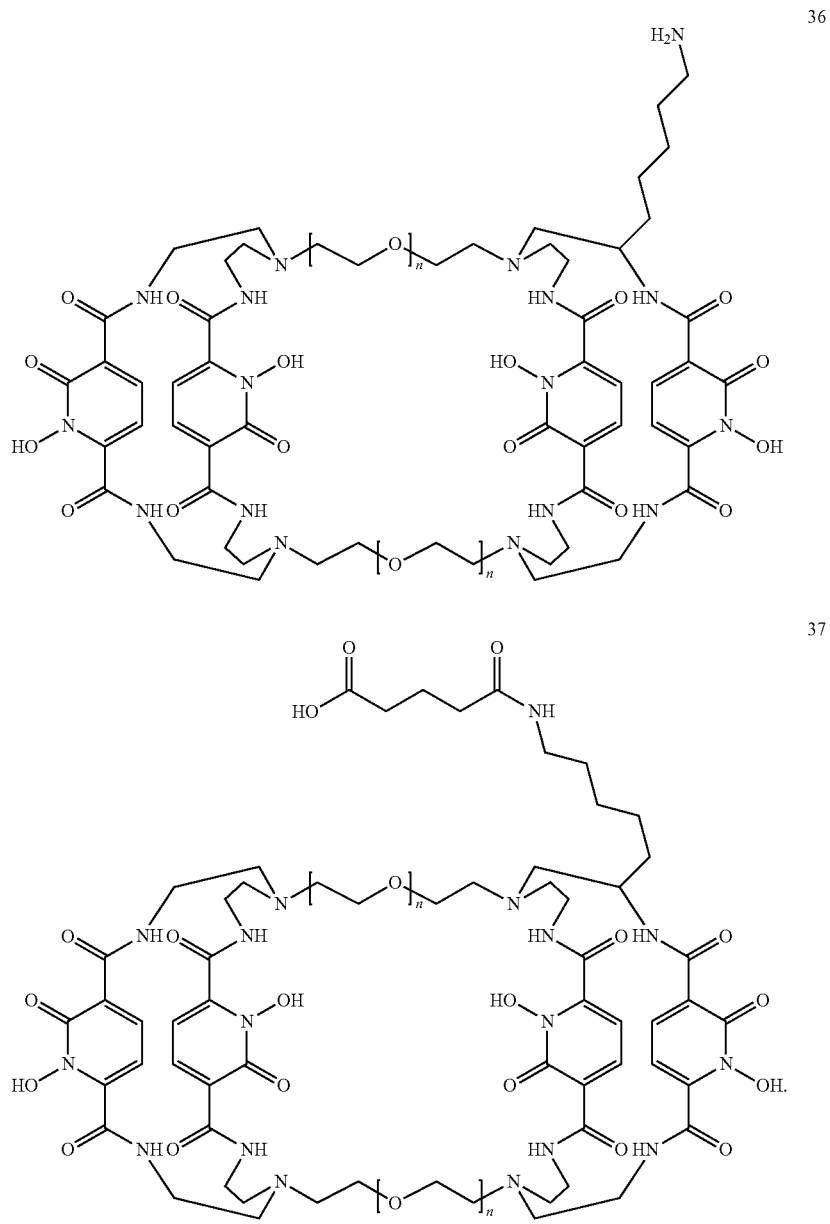

ing) with a positive charge, with a bulky organic compound that varies in hydrophobicity, charge, and structure. Exemplary molecules herein may be based on a PEG backbone that exhibits high aqueous solubility. One potential and considerable advantage for coupling to proteins in that it allows higher labeling levels (and therefore brightness) with less disruption of protein solubility.

Extinction Coefficient. A series of solutions of varied concentrations will be prepared from the solids based on mass and purity. The absorbance of each of these solutions at both 340 nm and at the appropriate acceptor wavelength will be measured and plotted according to Beer's Law ($A=\epsilon cL$ where A is absorbance, $\epsilon$ is the extinction coefficient in $M^{-1}$ $cm^{-1}$, c is concentration, and L is path length in cm) with the fitted linear regression slope equal to $\epsilon$ on a plot of A as a function of C.

Quantum Yield. Quantum yield will be measured using established methods [53, 54]. Fluorescence quantum yield Q are measured in diluted solution with an optical density lower than 0.1 using the following equation $Q_x/Q_r = [A_r(\lambda_r)/A_x(X_x)][n_x^2/n_r^2][D_x/D_r]$ were A is the absorbance at the excitation wavelength ($\lambda$), n the refractive index and D the integrated luminescence intensity. Subscripts "r" and "x" stand for reference and sample, respectively. References will be a quinine bisulfate in 1N sulfuric acid in aqueous solution ($Q_r=0.546$)[1] and $Ru(bpy)_3$ 2Cl complexes in water solution ($Q_r=0.028$)[2] for all complexes. A plot of integrated emission intensity (i.e. $D_r$) versus absorbance (i.e. $A_r(\lambda_r)$) yields a linear plot with a slope which can be equated to the reference quantum yield $Q_r$. By analogy, for the unknown sample, a plot of integrated emission intensity (i.e. $D_x$) versus absorbance (i.e. $A_x(\lambda_x)$) yields a linear plot and $Q_x$ can then be evaluated. A minimum of at least two independent measurements will be averaged to derive a reliable value.

Lifetime Determination. Fluorescent decay signals can be acquired using an IBH DataStation Hub photon counting module and data analysis performed using the commercially available DAS 6 decay analysis software package from HORIBA Jobin Yvon IBH. Goodness of fit will be assessed by minimizing the reduced chi squared function, $\chi^2$, and a visual inspection of the weighted residuals. Each trace will use at least 10,000 points and the reported lifetime values result from at least three independent measurements.

Stability Titrations. The general procedure used to determine the pEu values of ligands was adapted from an already described study using Gd [36, 55] and are similar to that already reported for other complexes [47]. Different volumes of a standardized DTPA stock solution were added to solutions of constant ligand, metal, and electrolyte concentrations. Concentrations of complexed ligand in each solution were determined by subtracting the remaining luminescence intensity after addition of DTPA to the initial luminescence intensity at identical pH and those concentrations were used as references for the analysis. Stability of compounds towards mM concentrations of EDTA and divalent cations will be assessed by incubation of the proposed molecules at nM concentration at room temperature in aqueous solutions of test ions. Time Resolved Fluorescent signal will be assessed at the outset of experiment and monitored over a minimum of 24 hours to determine signal change.

EXAMPLES

Example 1

1,2-HOPODA

2-Chloro-pyridine-3,6-dicarboxylic acid (3-2)

To a mixture of compound 2-chloro-6-methyl-nicotinic acid (25 gram, 0.146 mol) and water (1.5 L) in a 3 liter flask equipped with a mechanic stirrer and a heating mantle, potassium hydroxide (28 g, 0.5 mol) was added, the mixture turned to be a clear solution. Potassium permanganate (70 g, 0.44 mol) was added in ten batches during 36 hrs, the temperature of the reaction mixture was kept in the range of 85-95° C. during the reaction process.

The oxidation was monitored by the HPLC and proton NMR (in $D_2O$—NaOD). The reaction mixture was then filtered to remove the large amount of $MnO_2$ and the filtrate was acidified with conc. HCl. Pure product was obtained as snow-white crystals and was collected by filtration yield 25 grams of the product (85%).

$^1$H NMR (500 MHz, DMSO-$d_6$, 25° C.) δ: 8.117 (d, 1H, J=7.5 Hz), ArH), 8.344 (d, 1H, J=7.5 Hz, ArH), 13.847 (s, br, 2H, COOH).

$^{13}$C NMR (500 MHz, DMSO-$d_6$, 25° C.) δ: 124.1, 131.4, 141.4, 147.7, 150.0, 164.6, 165.8. (−)-High resolution ESI MS: m/Z: 199.9750 [M⁻], calculated 199.9751.

2-Chloro-pyridine-N-oxide-3,6-dicarboxylic acid (3-3)

2-Chloro-pyridine-3,6-dicarboxylic acid (25 g, 0.124-mol) was dissolved in 300 mL of $CF_3CO_2H$ and 46 mL of 30% $H_2O_2$ was added to this stirring solution. The solution was heated to 80° C., and the reaction process was monitored by HPLC. After the reaction finished, the reaction mixture was concentrated to ca. 50 mL by rotary evaporation and then added to 500 mL of ice water. The product immediately precipitated as a finely divided, white crystalline solid. It was isolated by filtration, washed with ice water, and dried in vacuum. This yielded 25 g (93%) of product.

$^1$HNMR (300 MHz, DMSO-$d_6$): δ 8.064(d, J=7.4 Hz1H), 8.209(d, J=7.4 Hz1H).

$^{13}$C NMR (300 MHz, DMSO-$d_6$, 25° C.) δ: 125.9, 130.6, 133.8, 139.9, 140.5, 160.3, 163.6.

X-Ray single crystal analysis confirms the product has the correct structure as expected.

1-Hydroxy-3,6-dicarboxy-2(1H)pyridinone (3-4)

A 21.7-g (0.10 mol) 2-chloro-pyridine-N-oxide-3,6-dicarboxylic acid (3-3) was dissolved in 350 mL of a 10% aqueous KOH solution, and the resulting solution was maintained at 80° C. overnight, the hydrolysis reaction was monitored by HPLC. The reaction mixture was then cooled in an ice bath and treated with concentrated HCl until the pH of solution reached 2. The brown-yellow suspended solid was isolated by filtration, washed with dilute HCl followed by three 15 mL portions of cold water, and then dried in vacuo yielding 17.5 g (8%).

$^1$H NMR (300 MHz, DMSO-$d_6$, 25° C.) δ: 7.193 (d, 1H, J=7.5 Hz), ArH), 8.059 (d, 1H, J=7.5 Hz, ArH), 15.346 (s, br, 2H, COOH).

$^{13}$C NMR (300 MHz, $D_2O$—NaOD, 25° C.) δ: 102.6, 123.3, 133.3, 148.1, 160.8, 170.3, 175.2.

X-Ray single crystal analysis confirms the product has the correct structure as expected.

1-Benzyloxy-3,6-dicarboxy-2(1H)-pyridinone dibenzyl ester (3-5)

1-Hydroxy-3,6-dicarboxy-2(1H)-pyridinone (3-4) (3 g, 0.015 mol) and anhydrous potassium carbonate (13.5 g, 0.09 mol) were mixed with benzyl chloride (9.5 g, 0.075 mol) in DMF (250 mL). The mixture was heated for 20 h, then filtered, and the filtrate evaporated to dryness. The residue was partitioned in mixture of 4 M of potassium carbonate aqueous solution (50 mL) and DCM (50 mL). The aqueous phase was extract with DCM (2×25 mL) and the combined organic phase was applied on a gradient flash silica column (0-3% methanol in DCM). The appropriate fractions were combined and evaporated to dryness as pale yellow oil.

¹H NMR(300 MHz, CDCl₃): δ 5.213(s, 2H), 5.285(s, 2H), 5.299(s, 2H), 6.341(d, 1H, J=7.5 Hz, ArH), 7.15-7.38(m, 15H, Benzyl ArH), 7.976(d, 1H, J=7.5 Hz, ArH).

¹³C NMR(75 MHz, DMSO-d₆): δ 71.9, 72.3, 75.0, 116.6, 127.3, 127.4, 128.7, 130.9, 131.4, 140.9, 148.2, 156.2, 165.0.

In following the general synthesis scheme shown in FIG. 3, Compound 3-5 can be used to synthesize Compound 3-13, a macrocyclic 1,2-HOPO structure substituted with a carboxyl-terminated linking arm. By appropriate selection of activated and protected moieties, such as in Compound 3-6, the orientation of a chelating moiety can be controlled with respect to a linking group. This principle applies to the various schemes depicted herein. Additional guidance for deprotecting, activating and attaching these and other chelators disclosed herein to a linking group can be found, for example in U.S. Pat. Nos. 5,624,901; 6,406,297; 6,515,113 and 6,846,915; and US Patent Application Publications 2008/0213780; 2008/0213917 and 2010/0015725.

Example 2

6-Me-3,2-HOPO

3-Hydroxy-6-methyl-2(1H)-pyridinone-4-carboxylic Acid (6-1)

This compound was synthesized by adapting a previously reported procedure (ref Feist, D. *Chem. Ber.* 1902, 35, 1540.). Sodium diethyloxylacetate (42.1 g, 200 mmol) was dissolved in THF (500 mL) and then placed into a 1-L three-neck round bottom flask. Chloroacetone (16 mL, 200 mmol) was added to the mixture. After 10 min, NH3 gas was bubbled through the reaction mixture. Finally, AlCl3 (2.67 g, 20 mmol) was slowly added. The reaction mixture was stirred under ambient conditions for 5 days. The resulting orange solid was filtered off and suspended in 1 M HCl (500 mL) so that the pH<3. The resulting suspension was stirred for 30 min and the precipitate filtered off, washed with distilled water, and recrystallized from hot EtOH (approximately 1 L) to yield colorless crystals (yield: 15.7 g, 40%). Mp: 227-229° C.

1H NMR (d6-DMSO, 300 MHz): δ 1.24 (t, 3H, CH3), 2.07 (s, 3H, CH3), 4.22 (q, 2H, CH2), 6.07 (s, 1H, CH).

Anal. Calcd (found) for C9H11O4N: C, 54.82 (55.06); H, 5.62 (5.53); N, 7.11 (7.07).

EI-MS (+): m/z 198 [MH⁺]·

3-Benzyloxy-6-methyl-2(1H)-pyridinone-4-carboxylic Acid (6-2)

K₂CO₃ (9.06 g, 65 mmol) and compound 6-1 (11.8 g, 60 mmol) were suspended in H₂O (650 mL), and the flask was immersed in an ultrasonic bath for 30 min in order to aid dissolution. This solution was added to a solution of benzyl bromide (7.8 mL, 65 mmol) in CH₂Cl₂ (500 mL) in a 2-liter three-neck round bottom flask. Cetylpyridinium chloride (9.09 g, 30 mmol) was added as a phase transfer catalyst for this reaction. The solution was stirred with an overhead stirrer, at 40° C. for 1 day until the reaction was complete. The two layers were separated, and the aqueous layer was extracted twice with CH₂Cl₂ (100 mL). The organic layers were combined, and the solvents were removed. Purification of this crude product was performed by column chromatography.

1H NMR (CDCl₃, 300 MHz), δ 1.29 (t, 3H, CH₃), 2.35 (s, 3H, CH₃), 4.30 (q, 2H, CH₂), 5.26 (d, 2H, CH₂), 6.22 (s, 1H, CH), 7.35 (m, 5H, ArH).

3-Benzyloxy-6-methyl-2(1H)-pyridinone-1-tert-butoxycarbonylmethyl-4-carboxylic acid ethyl ester (6-3)

To a 100 mL round-bottom flask was added 3.5 g (12.2 mmol) Bn-6-Me-3,2-HOPO (6-2). To this was added 5.3 g potassium fluoride on alumina (40 wt. %, 36.5 mmol). These reageants were purged under nitrogen for 15 minutes, after which 45 mL dimethoxyentane was added. To this solution was added 8.83 g (36.5 mmol) tert-butyl iodoacetate, and the reaction was left to stir for 2 days. After 2 days, an additional 15 mmol tert-butyl iodoacetate was added. After an additional 1.5 days, the reaction mixture was filtered, the alumina was washed thoroughly with THF, the solvent was evaporated, and the resulting light-brown oil purified by a gradient flash silica column, (0-5% MeOH in DCM). Yield 77%.

¹H NMR (300 MHz, DMSO-d₆, 25° C.): δ: 1.27(t, 3H), 1.48(s, 9H), 2.27(s, 3H), 4.27(q, 2H), 4.72(s, 2H), 5.23(s, 2H), 6.18(s, 1H), 7.3(m, 3H), 7.48(m, 2H). ESI+-MS: 402.19 (401.18)

¹³C NMR (500 MHz, DMSO-d₆, 25° C.): δ: 13.7, 22.1, 29.0, 49.2, 60.0, 72.6, 72.9, 103.7, 127.3, 127.4, 128.7, 130.1, 133.0, 140.9, 145.2, 161.4, 165.0, 1167.3.

In following the general synthesis scheme shown in FIG. 4, Compound 6-3 can be used to synthesize Compound 6-11, a macrocyclic 6-Me-3,2-HOPO structure substituted with a carboxyl-terminated linking arm.

Example 3

3,2-HOPO

3-Hydroxy-2(1H)-pyridinone-4-carboxylic acid ethyl ester (1-1)

To a stirred solution of 3-hydroxy-2-oxo-1,2,3,4-tetrahydro-pyridine-4-carboxylic acid ethyl ester (10 g, 54 mmol) in xylenes was added 5 g of 10% palladium on carbon. The solution was refluxed under nitrogen overnight, filtered and evaporated to yield an off-white solid. Recrystallization from methanol yielded the desired product.

¹H NMR (300 MHz, CDCl₃, 25° C.): δ: 1.25(t, 3H), 4.24(q, 2H), 6.25(d, 1H), 6.84(d, 1H), 10.12(bs, 1H), 11.85 (bs, 1H).

X-Ray single crystal analysis confirms the product has the correct structure as expected.

In following the general synthesis scheme shown in FIG. 5, Compound 1-1 can be used to synthesize Compound 1-11, a macrocyclic 3,2-HOPO structure substituted with a carboxyl-terminated linking arm.

Example 4

Eu Chelates with Aliphatic Linkages

A series of ligands were prepared with the same core sensitizing unit structure, with only the central chain length modified.

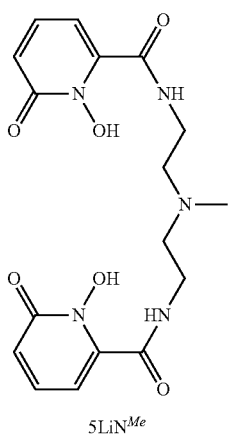

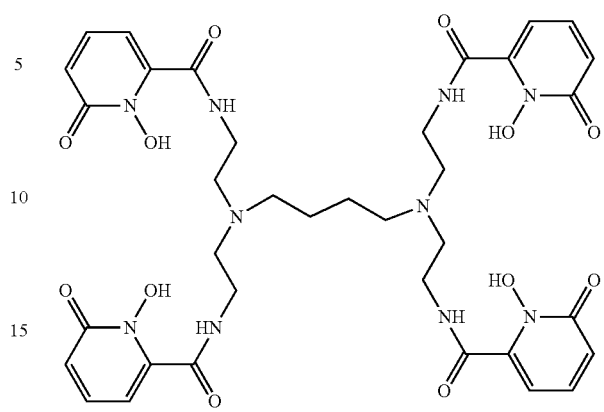

Prototype 1,2-HOPO Based Eu Chelating Agents. 5LIN$^{Me}$ represents a tetradentate prototype used to evaluate the characteristics of an amine linkage from the 5LIO (ether linkage) presented earlier. The H2-H4 series with aliphatic linking backbones were first generation macrocyclic chelates for Eu$^{3+}$.

These ligands were prepared primarily to develop an octadentate or 'eight-teeth' chelate that could form the basis for effective tethering to proteins and other macromolecules, while maintaining or improving stability and spectroscopic properties. Surprisingly, it was determined that conversion to these types of acyclic chelates was accompanied by significant reduction in the quantum yield, although pEu was largely unaffected. It was determined that these more rigid structures (compared to two independent tetradentate sensitizing units) did not allow sufficient geometric freedom to fully realize the fluorescence intensity potential of the Eu-1,2-HOPOs.

As a result of their highly luminescent properties with Eu(III) and excellent thermodynamic stability, 1,2-HOPO-based chelators seem promising for applications in highly sensitive biological assays. Having demonstrated that the 1,2-HOPO sensitizing units have the potential to deliver at least 22% quantum yield with exceptional stability, the inability of first generation octadentate chelates (H2-H4) to maintain the high quantum yield was surprising.

Photophysical and Stability Data of Various 1,2-HOPO Sensitized Eu Complexes[a]

|  | λ (nm) | ε (M$^{-1}$ cm$^{-1}$) | φ$_{Eu}$ | τ (H$_2$O, μs) | τ (D$_2$O, μs) | q | pEu[b] |
|---|---|---|---|---|---|---|---|
| Eu(5LiO) | 333 | 19,250 | 0.22 | 727 | 1012 | — | 18.6 |
| Eu(5LiN$^{Me}$) | 332 | 18,750 | 0.17 | 728 | 1000 | 0.1 | 17.3 |
| Eu(H2) | 341 | 18,200 | 0.036 | 480 | 1222 | 1.1 | 21.2 |
| Eu(H3) | 339 | 17,700 | 0.037 | 552; 253 | 811; 369 | 0.3; 1.0 | 17.5 |
| Eu(H4) | 337 | 17,900 | 0.031 | 649; 236 | 803; 338 | 0; 1.1 | 18.4 |

[a]see reference [47];
[b]by competitive batch titration using DTPA (pEu = 19.04) in 0.1M TRIS pH = 7.4 and 0.1M KCl.

Eu Chelates with Ether Linkages

Recent work has indicated that novel octadentate Eu chelates with bridging ether linkages overcome the quantum yield reduction exhibited by the octadentate aliphatic bridged chelates. A series of chelates have been prepared and characterized (1a-c).

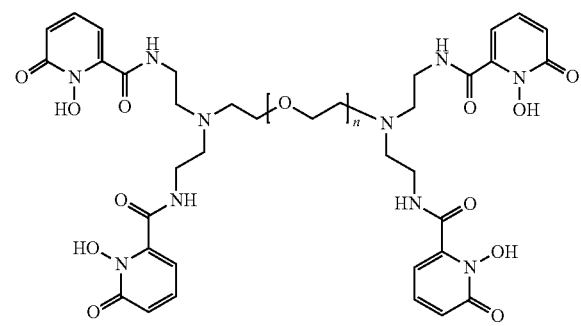

n = 1: H5-1 (1a)
2: H8-2 (1b)
3: H11-3 (1c)
4: H14-4 (1d)
5: H17-5 (1e)
6: H20-6 (1f)
7: H23-7 (1g)

Within this series, the central bridge connecting two tetradentate 1,2-HOPO units varies from a short ethyleneoxide chain (H5-1, 1a) to a longer, more flexible, triethyleneoxide (H11-3, 1c). The extension of the central chain improves the exclusion of an inner-sphere water molecule which is known to quench lanthanide luminescence and yields increased values of quantum yield in aqueous medium with an optimum of 17% for the H11-3 europium complex. The extension of the bridge also allows the H11-3 to reach photophysical properties close to the 5LIN$^{Me}$ model complex discussed above. Furthermore, the thermodynamic stability has been studied and shows that for the best sensitizers (H8-2 and H11-3), the complexes exhibit promising qualities that support their use in biological assays and complex medium.

The novel PEG backbone chelators exhibit the same absorption and emission spectra that is typical of the 1,2-HOPO sensitizing units with a very intense J=2 transition ($^7F_2 \leftarrow {}^5D_0$). A broad absorption band centered around 337 nm and a single, narrow emission at 620 nm. Closer inspection indicates a bifurcated emission peak at 620 nm owing to changes in the intensity of the J=1 transition ($^7F_1 \leftarrow {}^5D_0$) of the different backbone structures. Additionally, there is a very modest shift to higher energies in the absorption maxima of the different structures (see FIG. 6). There is also a trend towards a slight reduction in the overall extinction coefficient as longer backbone structures are used, although this is outweighed by significant increases in quantum yield, resulting in an overall increase in chelate luminescent intensity.

Interestingly, increasing the chain length (as well as the number of ether bridges) results in a concomitant increase in the aqueous quantum yield. This trend was not observed for the H2-H4 series, although the longest backbone in the aliphatic series was 4 atoms while the shortest in the PEG series was 5 atoms.

Estimates of q for Eu(H8-2) and Eu(H11-3) reveal no water molecule in the inner sphere, which correlates with the higher luminescence quantum yield. The luminescence quantum yield differences between Eu(H8-2) and Eu(H11-3) are not accompanied by any relevant changes in their luminescence lifetimes. This suggests that, while the triplet excited state energies undoubtedly play an important role in the sensitization process differences, they are not the only critical factor, with the efficiency of the energy transfer to the Eu(III) cation revealing itself to also be a crucial factor. The same conclusion is supported by photophysical data for Eu(H8-2) and Eu(H11-3) in DMSO (not presented).

Photophysical Data of the Investigated Eu Complexes

| | λ | ε | $\varphi_{Tot}$ | τ/µs | $\tau^D$/µs | q | pEu[b] |
|---|---|---|---|---|---|---|---|
| Eu(5LiO)[a] | 333 | 19,250 | 0.22 | 727 | 1012 | | 18.6 |
| Eu(5LiN$^{Me}$)[a] | 332 | 18,750 | 0.17 | 728 | 1000 | 0.1 | 17.3 |
| Eu(H5-1) | 337 | 15,900 | 0.067 | 651; 304 | 825; 438 | 0; 0.8 | 19.2 |
| Eu(H8-2) | 336 | 15,350 | 0.112 | 697 | 913 | 0 | 20.4 |
| Eu(H11-3) | 334 | 15,070 | 0.165 | 668 | 888 | 0.1 | 20.4 |

[a]see reference [47]
[b]by competitive batch titration using DTPA (pEu = 19.04) in 0.1M TRIS pH = 7.4 and 0.1M KCl.

The presence or absence of an inner-sphere coordinated water molecule is of critical importance for overall quantum yield, and those structures containing coordinated water either as the dominant or one of the species in solution all exhibit low quantum yields (H2, H3, H4, H5-1). Those species that exhibit only species without a quenching coordinated water, exhibit comparatively high quantum yields (H8-2 and H11-3). These trends indicate that the chelate backbone is not long enough to allow the total exclusion of the water molecule from the inner sphere, and that longer backbones may still offer significant increases in luminescence efficiency.

One practical concern related to the use of 1,2-HOPO ligands as Eu chelators for biological applications is complex stability. The 1,2-HOPO moiety is rather acidic (pKa of 5.8). It could be postulated that due to the low basicity, 1,2-HOPO ligands may produce unstable Eu(III) complexes. Spectrophotometric titration studies were thus performed to determine the pEu value for all 1,2-HOPO derivatives with Eu. The use of octadentate ligands illustrates the gain in stability when compared to the model complex Eu(5LIN$^{Me}$)$_2$. The increased pEu values for Eu(H5-2), Eu(H8-2) and Eu(H11-3) as compared to DTPA shows the high stability provided by the four 1,2-HOPO units (DTPA is FDA approved and provides a minimum stability for clinical application). Comparatively, the pEu values for Eu(H3) and Eu(H4) are decreased as compared to DTPA. Noteworthy is the 2.9 log unit decrease in stability for Eu(H3) relative to Eu(H8-2) and Eu(H11-3). As can be seen, a shorter backbone correlates to a smaller pEu value, suggesting that the complexation symmetry is different for Eu(H3), Eu(H4) and Eu(H5-1) compared to Eu(H8-2) and Eu(H11-3) and that the resulting symmetry of the complexation provide different stabilities for the formed complexes.

Figure 6A:
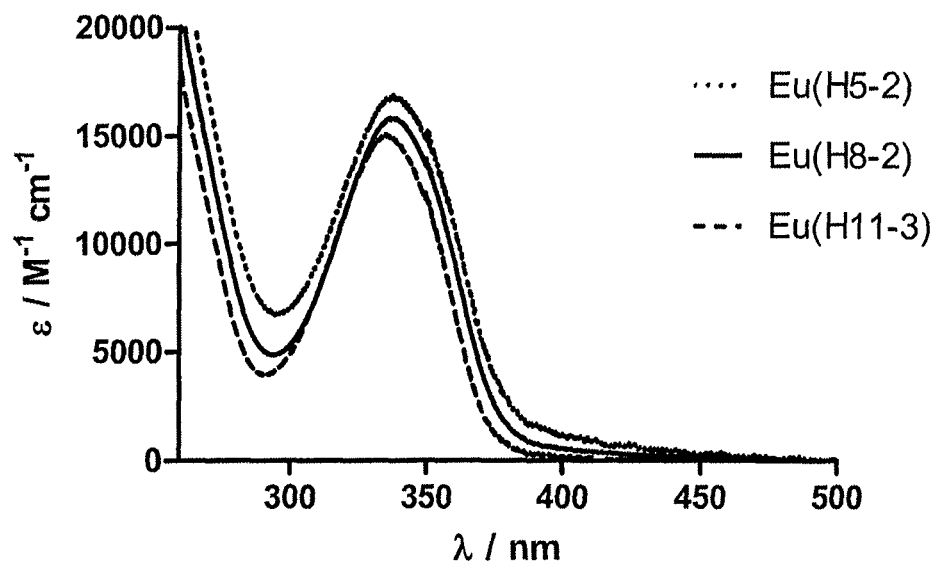
FIG. 6 shows absorption (top) and luminescence (bottom) spectra of Eu(H5-2) (–), Eu(H8-2) (red line) and Eu(H11-3) (blue line) in 0.1M TRIS buffer at pH=7.4 ($\lambda_{ex}$=340 nm).
Figure 6B:
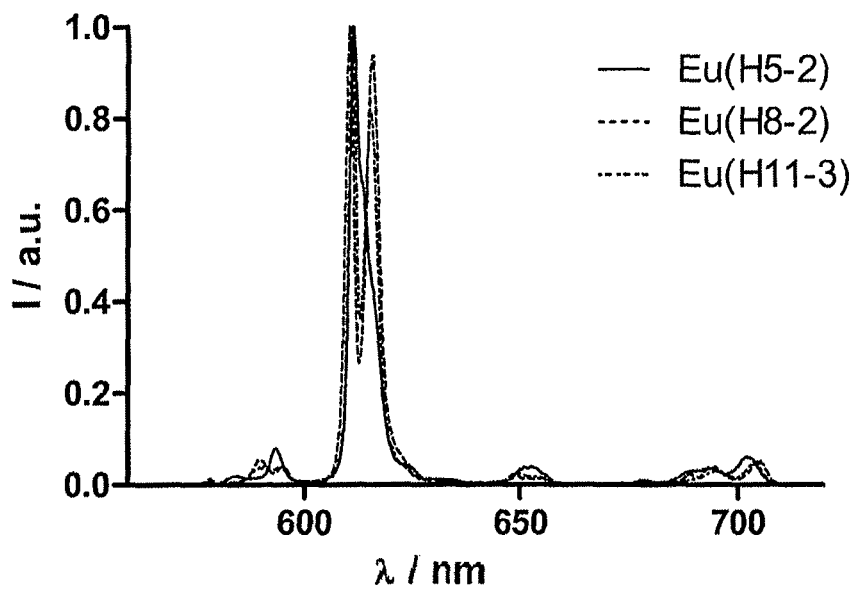
Figure 7:
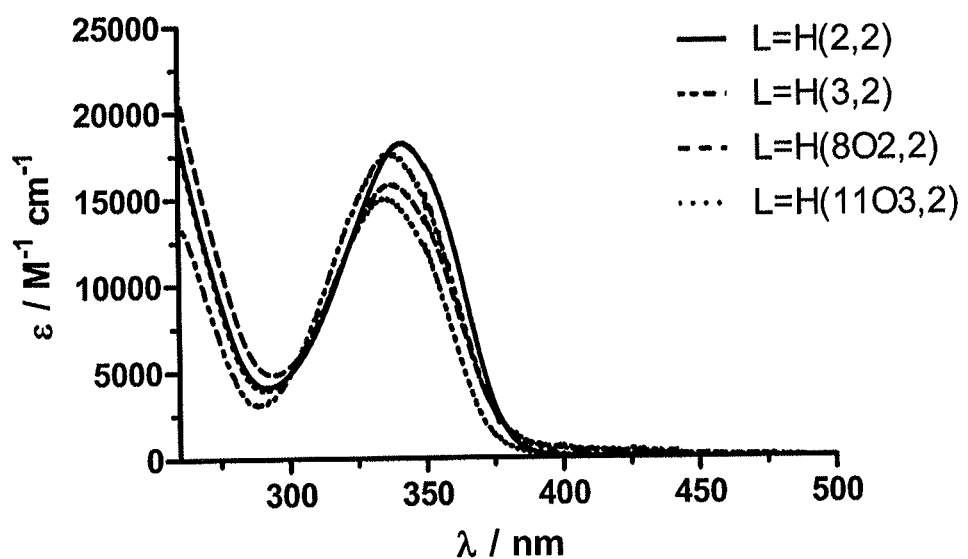
FIG. 7 shows UV/visible absorption spectra of $[Eu(H(2,2)-1,2-HOPO)]^0$ (–), $[Eu(H(3,2)-1,2-HOPO)]^0$ (–), $[Eu(H(8O2,2)-1,2-HOPO)]^0$ (–) and $[Eu(H(11O3,2)-1,2-HOPO)]^0$ (–) in 0.1M TRIS buffer (pH=7.4).

Additional stability testing of Eu(H11-3) in concentrated solutions of divalent cations and EDTA has resulted in significant signal loss over 24 hrs, due to the exchange of the Eu$^{3+}$ ion out of the H11-3 chelating unit (FIG. 6). Although these conditions represent concentrations that are in excess of those typically encountered in routine commercial use, they are a benchmark used in the high-throughput screening industry to evaluate these types of molecules. For comparison, stability testing of the commercialized Lumi-4-Tb compound is shown (FIG. 3, top) and represents the stability benchmark for these types of molecules.

UV Visible Absorption Spectroscopy

The UV/visible absorption data for each of the Eu(III) complexes in TRIS buffer solution (pH=7.4) are summarized in Table 4. Each of the spectra have absorption maxima around 335-340 nm (FIG. 2). Those bands are composed of two electronic transitions; at higher energy, a purely π-π* transition and, at slightly lower energy (around 'ca. 320 nm), a π-π* transition with some n-π* character, as evidenced previously from TD-DFT calculations. Absorption maxima are slightly shifted toward higher energy upon increasing the bridge length suggesting a small interaction between the terminal 5LIN$^{Me}$-1,2-HOPO units. This interaction gives maxima blue-shifting from 341 nm for [Eu(H(2,2)-1,2-HOPO)]$^0$ to 334 nm for [Eu(H(17O5,2)-1,2-HOPO)]$^0$ (as low as 332 nm for [Eu(5LIN$^{Me}$-1,2HOPO)$_2$]$^0$). At the same time, the molar absorption coefficients decrease considerably as the length of the central bridge is increased, by as much as 15% for [Eu(H(17O5,2)-1,2-HOPO)]$^0$ compared to other 1,2-HOPO complexes previously reported.

TABLE 4

UV/visible absorption data of the studied Eu(III) complexes in TRIS buffer (pH = 7.4), brightness at maximum absorption and triplet excited state energies.

| | TRIS buffer pH = 7.4 | | | 77K$^a$ T$_{0-0}$/ |
|---|---|---|---|---|
| | $\lambda^{max}_{abs}$/ nm | ε/M$^{-1}$·cm$^{-1}$ | Brightness$^a$ M$^{-1}$·cm$^{-1}$ | nm (cm$^{-1}$) |
| [Eu(H(2,2)-1,2HOPO)]$^0$ | 341 | 18,200 | 655 | 21,980 |
| [Eu(H(3,2)-1,2HOPO)]$^0$ | 339 | 17,700 | 655 | 21,900 |
| [Eu(H(4,2)-1,2HOPO)]$^0$ | 337 | 17,900 | 555 | 22,390 |
| [Eu(H(5O,2)-1,2HOPO)]$^0$ | 337 | 15,900 | 1065 | 22,000 |
| [Eu(H(8O2,2)-1,2HOPO)]$^0$ | 336 | 15,350 | 1720 | 22,320 |
| [Eu(H(11O3,2)-1,2HOPO)]$^0$ | 334 | 15,070 | 2485 | 22,120 |
| [Eu(H(14O4,2)-1,2HOPO)]$^0$ | 336 | 15,200 | 2920 | 22,020 |
| [Eu(H(17O5,2)-1,2HOPO)]$^0$ | 336 | 15,000 | 2940 | 21,690 |
| [Eu(5LIN$^{Me}$-1,2HOPO)$_2$]$^0$ | 332 | 18,050 | 3120 | 22,010 |

$^a$determined in a solid matrix at 77K (methanol/ethanol 1/4) using the Gd complexes.

It should be noticed that no differences were observed when comparing the UV/visible absorption spectra of the gadolinium and europium complexes. Furthermore, inspection of the UV/visible properties of the free ligand in the same conditions reveals the same blue shift of the absorption maximum upon increasing the length of the central bridge. This result shows that the effect observed with europium (and gadolinium) arises from an interaction between the terminal 5LIN$^{Me}$-1,2-HOPO motifs within one octadentate ligand. Regarding nomenclature, it is noted that "EU(H11-3)" is equivalent to "Eu(H(11O3,2)-1,2HOPO)" and similarly for the other compounds.

Luminescence of Gd Complexes

Estimation of the energies of the ligand based triplet excited state were determined using the Gd(III) complexes. Gadolinium was chosen because it is a 4f$^7$ lanthanide cation having a similar 4f electronic configuration and size as the europium cation (4f$^6$), but lacking an accessible metal based low energy electronic excited state. At room temperature, only a broad weak emission centered between 380-400 nm can be seen for the Gd(III) complexes. This emission can be attributed to the poorly emissive singlet excited state of the 1,2-HOPO chromophore in complex with the gadolinium cation.

Figure 8:
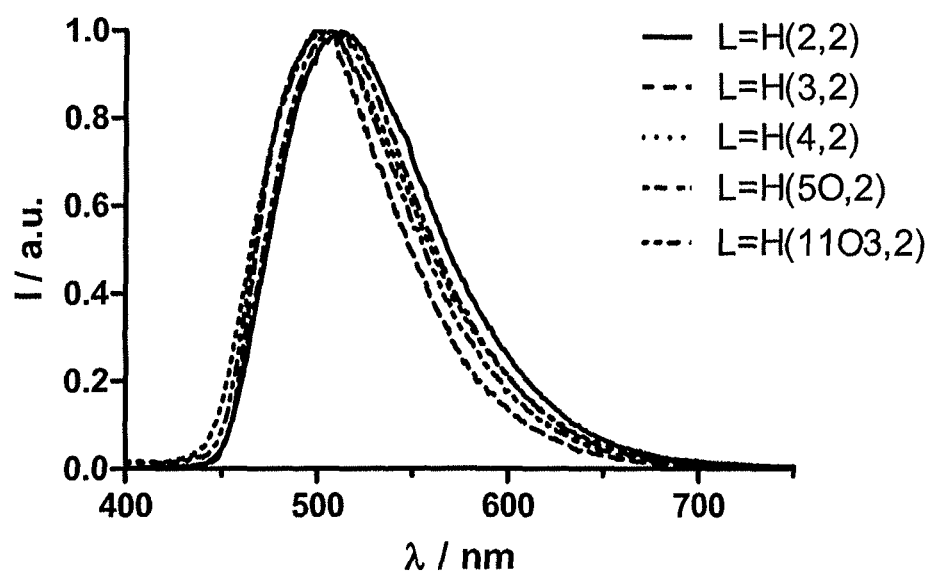
FIG. 8 shows time gated spectra of $[Gd(H(2,2)-1,2-HOPO)]^0$ (–), $[Gd(H(3,2)-1,2-HOPO)]^0$ (–), $[Gd(H(4,2)-1,2-HOPO)]^0$ (–), $[Gd(H(5O,2)-1,2-HOPO)]^0$ (–) and $[Gd(H(11O3,2)-1,2-HOPO)]^0$ (–) in methanol/ethanol (1/4) at 77K ($\lambda_{ex}$=330 nm, delay: 0.1 ms).

At 77K, in solid matrix, an emission band at approx. 500 nm can be seen (FIG. 8). This emission, red-shifted compared to the singlet excited state, can be assigned to phosphorescence from the triplet excited state, lower in energy than the singlet excited state observed at room temperature. Selective time gated phosphorescence spectra (delay 0.1 ms) of the gadolinium complexes at 77K are depicted in FIG. 8. From these spectra, it appears the triplet excited states of the complexes are almost at the same energy (22,110+/−210 cm$^{-1}$). This result suggests that the small interaction observed on the singlet excited state is absent (or weak enough to not be observed). Such little differences in triplet excited state energies should not provide large sensitization efficiency differences since all the triplet excited states possess almost the same energy gap with respect to the $^5D_2$ (E=21,519 cm$^{-1}$) and the $^5D_1$ (E=19,028 cm$^{-1}$) accepting levels of europium.

Luminescence of Eu Complexes

Figure 9A:
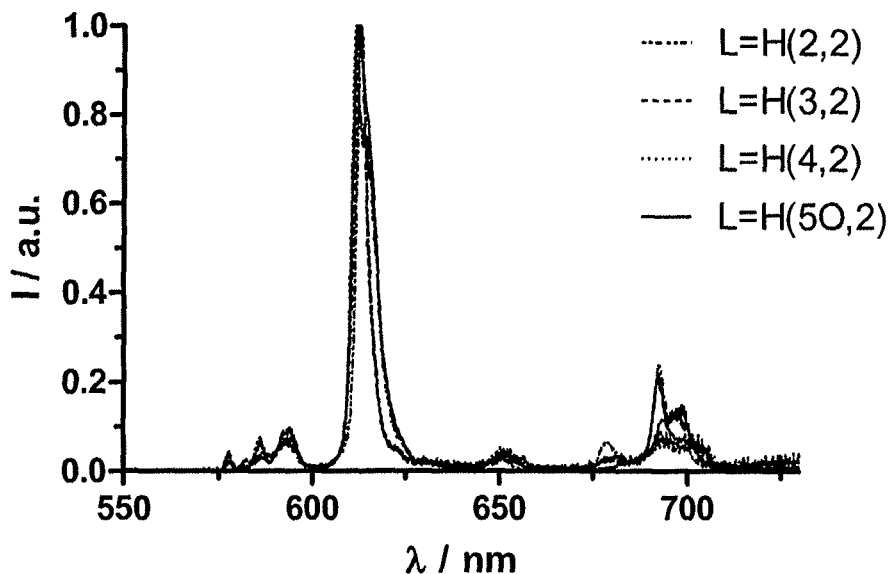
FIG. 9 shows (a) luminescence spectra of $[Eu(H(2,2)-1,2-HOPO)]^0$ (–), $[Eu(H(3,2)-1,2-HOPO)]^0$ (–), $[Eu(H(4,2)-1,2-HOPO)]^0$ (–) and $[Eu(H(5O,2)-1,2-HOPO)]^0$ (–); (b) $[Eu(H(8O2,2)-1,2-HOPO)]^0$ (–), $[Eu(H(11O3,2)-1,2-HOPO)]^0$ (–), $[Eu(H(14O4,2)-1,2-HOPO)]^0$ (–) and $[Eu(H(17O5,2)-1,2-HOPO)]^0$ (–) at room temperature in 0.1 M TRIS buffer at pH=7.4 ($\lambda_{ex}$ =340 nm).
Figure 9B:
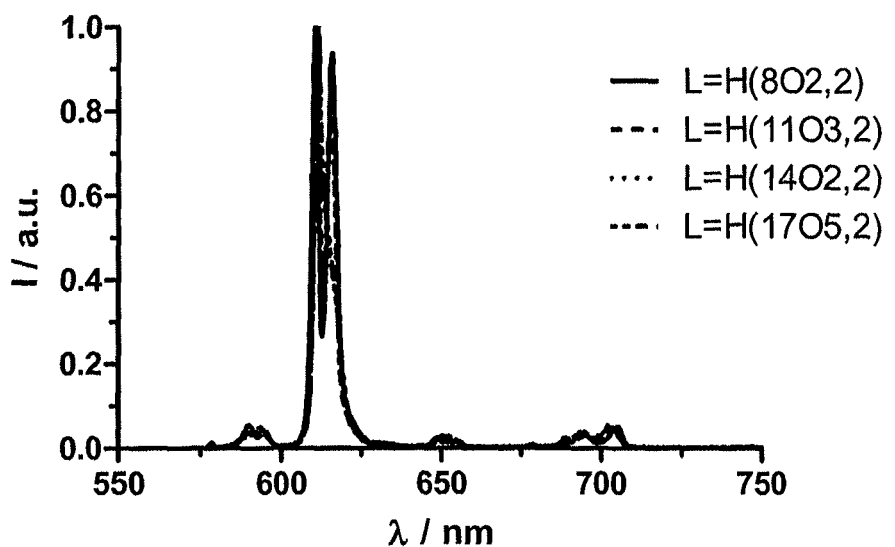
Figure 10B:
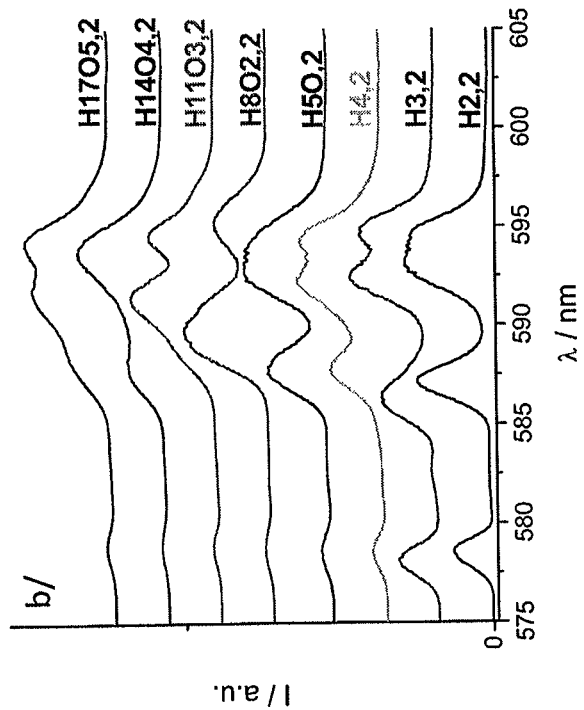
FIG. 10 shows (a) luminescence spectra and highlight of the J=0 and J=1 transitions of $[Eu(H(2,2)-1,2-HOPO)]^0$ (–), $[Eu(H(3,2)-1,2-HOPO)]^0$ (–), $[Eu(H(4,2)-1,2-HOPO)]^0$ (–) and $[Eu(H(5O,2)-1,2-HOPO)]^0$ (–); $[Eu(H(8O2,2)-1,2-HOPO)]^0$ (–), $[Eu(H(11O3,2)-1,2-HOPO)]^0$ (–), $[Eu(H(14O4,2)-1,2-HOPO)]^0$ (–) and $[Eu(H(17O5,2)-1,2-HOPO)]^0$ (–) at 77K in solid matrix (Ethanol:Methanol 4:1) ($\lambda_{ex}$=340 nm).
Figure 10A:
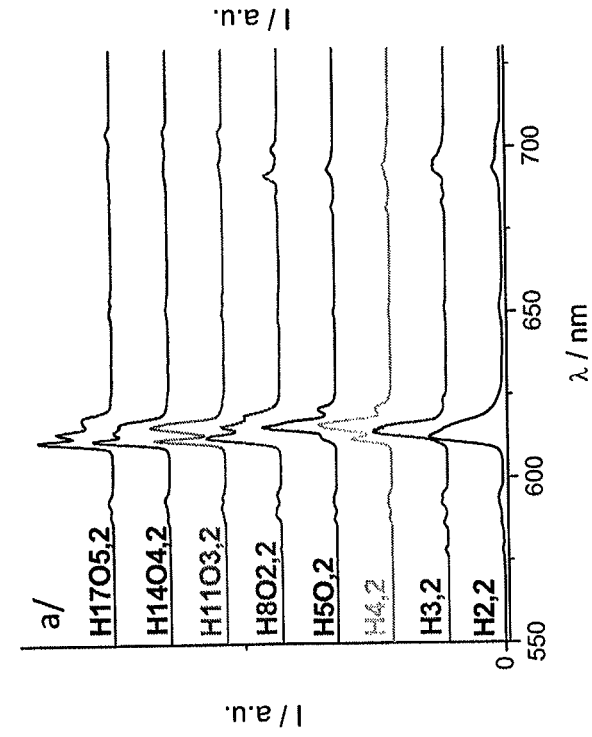

As expected from the difference in crystal field, the nona-coordinated and octa-coordinated complexes present some differences in the luminescence pattern with different relative intensities and splitting for all transitions (see FIG. 9) giving an unusual type of spectrum for [Eu(H(2,2)-1,2-HOPO)]$^0$ compared to all 1,2-HOPO octa-coordinated derivatives. For all octa-coordinated complexes, as can be seen in FIG. 9, the emission spectra are typical with very intense J=2 transition ($^5D_0 \to ^7F_5$). The intensity of the J=1 band ($^5D_0 \to ^7F_1$) changes as compared to the overall intensity (FIG. 9), yielding different luminescence radiative parameters (vide infra). Also the pattern of the J=1 changes, that indicates a change in the geometry around the metal centre. Of interest is also the similarities in pattern and spectra of [Eu(H(2,2)-1,2-HOPO)]$^0$ and [Eu(H(3,2)-1,2-HOPO)]$^0$, with intense J=1 and J=4 (when compared to the J=2) suggesting that the emission observed for [Eu(H(3,2)-1,2-HOPO)]$^0$ arises from a nona-coordinated species (as previously observed for [Eu(H(2,2)-1,2-HOPO)]$^0$). For [Eu(H(4,2)-1,2-HOPO)]$^0$, one can see on FIG. 10 that the J=4 transition is intermediate between [Eu(H(2,2)-1,2-HOPO)]$^0$ and [Eu(H(5O,2)-1,2-HOPO)]$^0$ (as all other complexes with longer bridges) suggesting that there are two different emitting species in solution (one nona- and the other octa. -coordinated). This change in pattern is also observed at 77K, in solid matrix, supporting the change of geometry around the Eu(III) ion (FIG. 10b). Importantly, the position of the J=0 transitions is unique for all differing emitting complexes in solution, but the broadness of this transition in this case (even at 77K) precludes any definitive conclusion. As shown in FIG. 10b, the $^5D_0 \to ^7F_1$ transition is composed of three peaks for all europium (III) complexes at room temperature and at 77K in solid matrix. While the broadness of the transition again precludes a definitive determination of the exact point group of the complex, such multiplicity suggests that from the three most common coordination polyhedra, the best match to the observed luminescence spectra is obtained for the bicapped trigonal prism (C$_{2v}$) geometry as noted elsewhere for similar derivatives. The differences of splitting intensities and of splitting energies in the J=1 transition (previously used to reveal the crystal field symmetry) shows that although the geometry changes from one complex to the other, the general crystal field is unaffected since the multiplicity of the splitting remains unchanged.

In addition to the steady state emission spectra, the luminescence quantum yields and luminescence lifetimes of the Eu(III) complexes were also measured in aqueous solution with 0.1 M TRIS buffer pH=7.4 and in deuterated solution to estimate the number of inner sphere water molecule (i.e. q) using the improved Horrock's equations. All photophysical characterizations are summarized in Table 5.

Figure 13A:
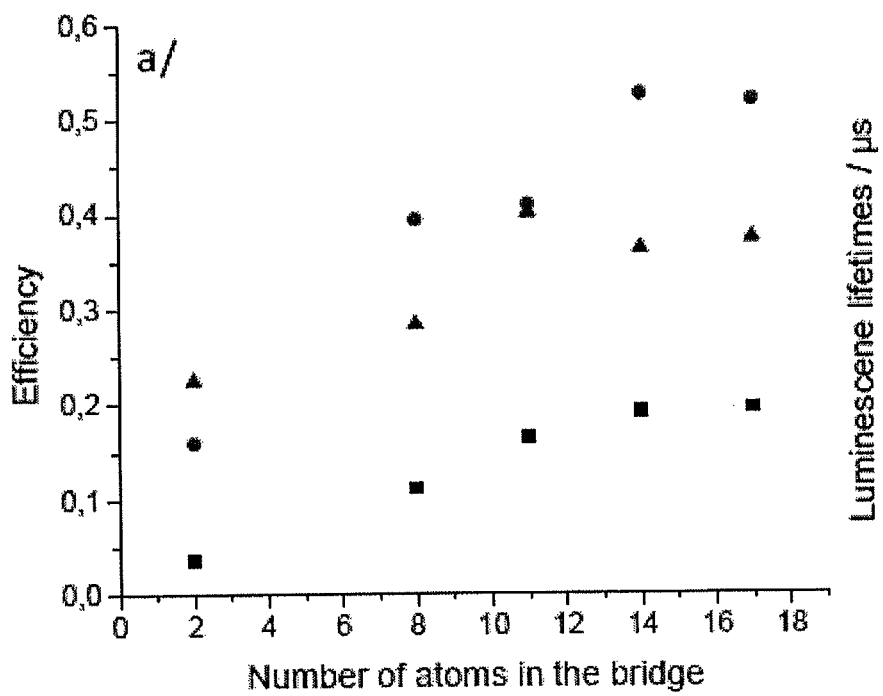
FIG. 13 shows (a) Variation of the luminescence quantum yield (■), metal centered efficiency (●) and sensitization efficiency (▲) as a function of the number of atoms in the central bridge; (b) Variation of the luminescence lifetimes (■) [in the square, ●: second component of the luminescence lifetimes] and radiative luminescence lifetimes (▲) as a function of the number of atoms in the central bridge.

As can be readily seen, the central bridge by inducing constraint on the complexation geometry (for short bridges) influences all the luminescence properties. Increasing the chain length results in a subsequent increase of the luminescence efficiency (going from 0.031 to 0.197 for [Eu(H(4,2)-1,2-HOPO)]$^0$ and [Eu(H(17O5,2)-1,2-HOPO)]$^0$, respectively, FIG. 13a). More into details, the luminescence quantum yields are in the same order from [Eu(H(2,2)-1,2-HOPO)]$^0$ through [Eu(H(4,2)-1,2-HOPO)]$^0$ then, a constant increase is observed until reaching a plateau for [Eu(H(14O4,2)-1,2-HOPO)]$^0$ and [Eu(H(17O5,2)-1,2-HOPO)]$^0$ (FIG. 13a). Noticeably, the maximum quantum yield obtained is higher than that of the model bis-tetradentate complex ([Eu(5LIN$^{Me}$-1,2HOPO)$_2$]$^0$) suggesting that the geometry of the complexed ligand is different in octadentate-structures versus bis-tetradentate-structures.

As demonstrated elsewhere, the luminescence lifetime of [Eu(H(2,2)-1,2-HOPO)]$^0$ is short because of the single water molecule in its inner sphere ($\tau$=480 µs). For the shorter central bridge, from [Eu(H(3,2)-1,2-HOPO)]$^0$ to [Eu(H(5O,2)-1,2-HOPO)]$^0$, the luminescence decay traces only gave satisfactory fits when modelled as biexponential decays, composed of a short component ($\tau$=253 µs, 236 µs, 304 µs for [Eu(H(3,2)-1,2-HOPO)]$^0$, [Eu(H(4,2)-1,2-HOPO)]$^0$, [Eu(H(5O,2)-1,2-HOPO)]$^0$ respectively) and a longer one ($\tau$=552 µs, 649 µs, 651 µs for [Eu(H(3,2)-1,2-HOPO)]$^0$, [Eu(H(4,2)-1,2-HOPO)]$^0$, [Eu(H(5O,2)-1,2-HOPO)]$^0$ respectively). This biexponential behavior emphasizes the presence of two different species in solution with these shorter bridges. From [Eu(H(8O2,2)-1,2-HOPO)]$^0$ to [Eu(H(17O5,2)-1,2-HOPO)]$^0$, the measured luminescence lifetimes are monoexponential and are in the same range (between 650 µs to 720 µs) in 0.1 M TRIS buffer solution (pH=7.4) while in deuterated water, the luminescence lifetimes vary from 825 µs to 915 µs (Table 5, FIG. 13b).

the presence of two type of complexes, one hydrated and one not. This can be explained by the constraint that is due to the central bridge; the H(2,2) bridge allows only the formation of hydrated complex while the extension of the chain length of the bridge allows better protection of the metal center after complexation by increasing the degrees of freedom between the two terminal 5LIN$^{Me}$-1,2-HOPO motifs. This latter fact is supported by the q=0.3 for [Eu(H(3,2)-1,2-HOPO)]$^0$ which suggests that the propyl chain favors the formation of both an eight and nine coordinate species since the chain is not long enough to form a single eight coordinate complex species, but is too long to form a single nine coordinate complex as obtained for [Eu(H(2,2)-1,2-HOPO)]$^0$.

Luminescence lifetimes were also determined at 77K, in a solid matrix (Table 5), which have allowed us to determine whether back energy transfer between the donor triplet excited state and the acceptor manifold excited state of the lanthanide is present, or alternately whether quenching via low lying LMCT state occurs. In the present case, as can be seen from Table 5, no such quenching can be evidenced since there is only a small difference between the luminescence lifetimes in solution and in solid state (77K).

Since the luminescence quantum yield does not take into account the absorptivity of the molecule, a more accurate way to rank the overall efficiency for these compounds is to examine their brightness, typically defined as the product of the luminescence quantum yield with the molar absorption coefficient.

TABLE 5

Photophysical data of the investigated Eu complexes.

| | 0.1M TRIS buffer pH = 7.4 | | | | 77K[a] |
|---|---|---|---|---|---|
| | $\phi_{Tot}$ | $\tau$/µs | $\tau^D$/µs | q | $\tau$/µs |
| [Eu(H(2,2)-1,2HOPO)]$^0$ | 0.036 | 480 | 1222 | 1.1 | 914 |
| [Eu(H(3,2)-1,2HOPO)]$^0$ | 0.037 | 552; 253 | 811; 369 | 0.3; 1.0 | 1040; 781 |
| [Eu(H(4,2)-1,2HOPO)]$^0$ | 0.031 | 649; 236 | 803; 338 | 0; 1.1 | 902; 645 |
| [Eu(H(5O,2)-1,2HOPO)]$^0$ | 0.067 | 651; 304 | 825; 462 | 0; 1.1 | 823; 608 |
| [Eu(H(8O2,2)-1,2HOPO)]$^0$ | 0.112 | 697 | 913 | 0 | 748 |
| [Eu(H(11O3,2)-1,2HOPO)]$^0$ | 0.165 | 668 | 888 | 0.1 | 765 |
| [Eu(H(14O4,2)-1,2HOPO)]$^0$ | 0.192 | 700 | 961 | 0.1 | 819 |
| [Eu(H(17O5,2)-1,2HOPO)]$^0$ | 0.196 | 704 | 962 | 0.1 | 826 |
| [Eu(5LIN$^{Me}$-1,2HOPO)$_2$]$^0$ | 0.173[b] | 728[b] | 1000[b] | 0.1[b] | 860 |

[a]measured in a solid matrix at 77K (methanol/ethanol 1/4).

Figure 11:
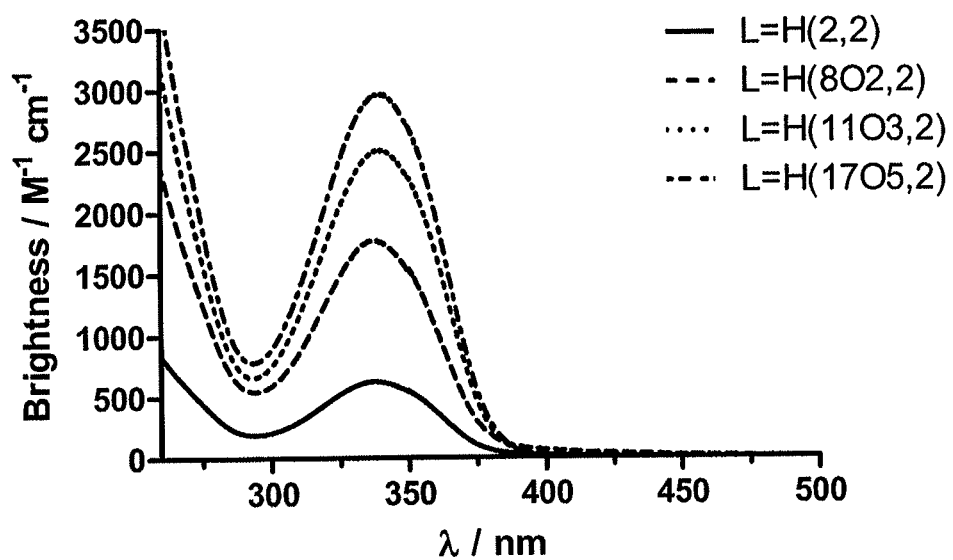
FIG. 11 shows brightness of $[Eu(H(2,2)-1,2-HOPO)]^0$ (–), $[Eu(H(8O2,2)-1,2-HOPO)]^0$ (–), $[Eu(H(11O3,2)-1,2-HOPO)]^0$ (–) and $[Eu(H(17O4,2)-1,2-HOPO)]^0$ (–) in 0.1 M aqueous TRIS buffer at pH=7.4.

These lifetime differences (between TRIS water and deuterated water) can be related to the hydration states of the complexes. Estimates of q reveal no water molecule in the inner sphere for all complexes with bridge longer than the [Eu(H(8O2,2)-1,2-HOPO)]$^0$. Importantly, the obvious luminescence quantum yield differences between [Eu(H(8O2,2)-1,2-HOPO)]$^0$ and [Eu(H(17O5,2)-1,2-HOPO)]$^0$ are not accompanied by any relevant changes in their luminescence lifetimes. This suggests that, while the triplet excited state energies undoubtedly play an important role in the sensitization process differences, the efficiency of the intersystem crossing and the "quantity of energy" accessing to the triplet excited state is also a crucial factor that affect the luminescence quantum yield. As explained above, from [Eu(H(3,2)-1,2-HOPO)]$^0$ through [Eu(H(5O,2)-1,2-HOPO)]$^0$, biexponential decays were obtained (in TRIS at pH=7.4, in deuterated water or at 77K in solid matrix) revealing the presence of two emitting species with those ligands having from three to five atoms in the central bridge. The subsequent measured luminescence lifetimes in deuterated water reveal For these complexes, as highlighted in the UV/visible absorption study, the molar absorption coefficient decreases by 15% going from the short [Eu(H(2,2)-1,2-HOPO)]$^0$ to the longer derivatives (from [Eu(H(8O2,2)-1,2-HOPO)]$^0$ to [Eu(H(17O5,2)-1,2-HOPO)]$^0$, vide supra). This advantage to the shorter bridge complexes is counterbalanced by the large difference in quantum yield going from 3% to almost 20% for the longer bridged complexes. This results in increased brightness by extending the central bridge of these types of chelators going from 655 M$^{-1}$·cm$^{-1}$ for [Eu(H(2,2)-1,2-HOPO)]$^0$ to 2940 M$^{-1}$·cm$^{-1}$ for [Eu(H(17O5,2)-1,2-HOPO)]$^0$, respectively (FIG. 11). This latter brightness value is as large as the one obtained for the best bis-tetradentate ligands as illustrated by [Eu(5LIN$^{Me}$-1,2-HOPO)$_2$]$^0$ (3400 M$^{-1}$·cm$^{-1}$).

Calculation of Eu Parameters

As demonstrated elsewhere, the efficiency of the sensitization can be estimated using a method that defines the overall luminescence quantum yield ($\phi_{Eu}$) as the product of the efficiency of the intersystem crossing ($\eta_{ISC}$), the efficiency of the energy transfer ($\eta_{ET}$) and the efficiency of metal centred luminescence ($\eta_{Eu}$): $\phi_{Eu}=\eta_{ISC}\ \eta_{ET}\ \eta_{Eu}=\eta_{sens}\ \eta_{Eu}$. In this equation, the $\eta_{ISC}\ \eta_{ET}$ term is termed the sensitization efficiency, $\eta_{sens}$ ($\eta_{sens}=\eta_{ISC}\ \eta_{ET}$). All the luminescence parameters $\tau_R$ (the pure radiative luminescence lifetime), $k_r$ and $k_{nR}$ (the radiative and non-radiative constant rate) can be deduced. These parameters were calculated for five of the octadentate complexes and the model complex that present only one species in solution at pH=7.4 and are reported in Table 6.

TABLE 6

Photophysical data of the investigated complexes containing only one species in aqueous TRIS pH = 7.4 (see supplementary information for details).

| | $\phi_{Tot}$ | $\tau/\mu s$ | $\tau_{rad}/\mu s$ | $k_r/s^{-1}$ | $k_{nr}/s^{-1}$ | $\eta^{Eu}$ | $\eta^{sens}$ |
|---|---|---|---|---|---|---|---|
| [Eu(H(22)-1,2-HOPO)] | 0.036 | 480 | 3000 | 333 | 1750 | 0.160 | 0.225 |
| [Eu(H(8O2,2)-1,2-HOPO)] | 0.112 | 697 | 1770 | 566 | 869 | 0.395 | 0.284 |
| [Eu(H(11O3,2)-1,2-HOPO)] | 0.165 | 668 | 1630 | 615 | 882 | 0.411 | 0.402 |
| [Eu(H(14O4,2)-1,2-HOPO)] | 0.192 | 700 | 1326 | 754 | 674 | 0.528 | 0.364 |
| [Eu(H(17O5,2)-1,2-HOPO)] | 0.196 | 704 | 1348 | 742 | 679 | 0.522 | 0.375 |
| [Eu(5LIN$^{Me}$-1,2-HOPO)$_2$] | 0.173 | 728 | 1770 | 566 | 807 | 0.412 | 0.420 |

Figure 12:
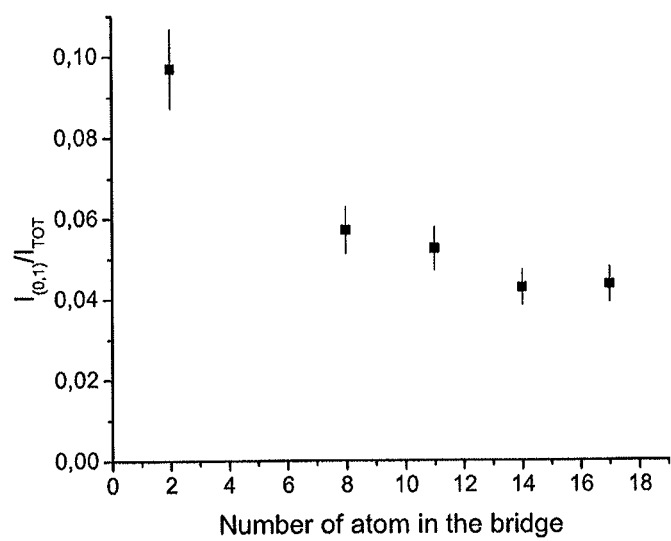
FIG. 12 shows variation of the ratio $I_{(0,1)}/I_{TOT}$ as a function of the number of atoms in the central bridge. The vertical bars represent the error on each point.

As detailed earlier (vide supra), the geometric changes around the Eu(III) ion can be seen by integrating the J=1 transition over the all spectrum resulting in a decrease of the intensity of $I_{(0,1)}/I_{TOT}$ (FIG. 12) for all complexes as a function of the number of atoms in the central bridge.

Figure 13B:
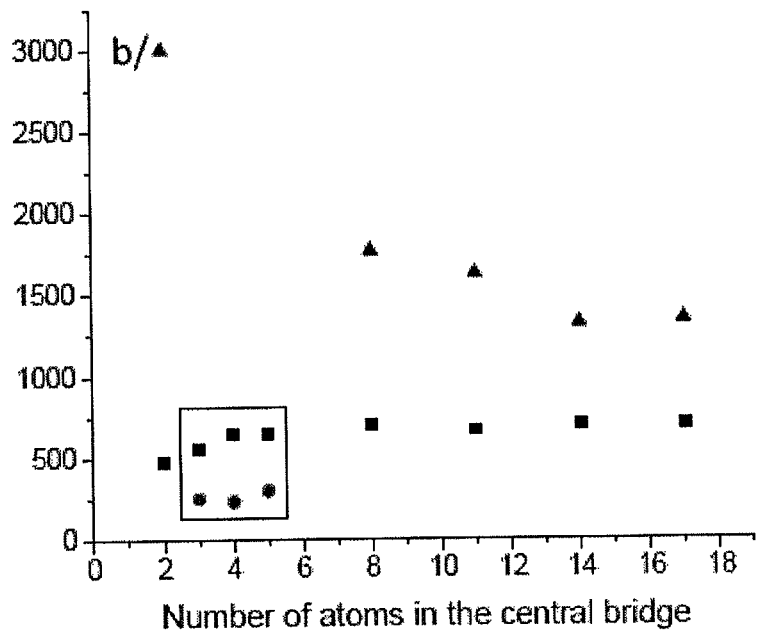

As can be readily seen from Table 6, there are some striking similarities among the $k_r$ and $k_{nr}$ values that can be also found for the previously reported [Eu(5LIN$^{Me}$-1,2-HOPO)$_2$]$^0$. In detail, the radiative decay is smaller than the non-radiative decay for all complexes until [Eu(H(14O4,2)-1,2-HOPO)]$^0$ yielding a metal centred efficiency inferior to 50% while for [Eu(H(14O4,2)-1,2-HOPO)]$^0$ and [Eu(H(17O5,2)-1,2-HOPO)]$^0$, the radiative and non-radiative decay are equal allowing to obtain an optimized metal centred efficiency around 50%. This limitation is in line with the results already published for tetradentate 1,2-HOPO derivatives where 50% efficiency seems to be a limit in TRIS buffer for the 1,2-HOPO derivatives. Indeed, as can be noticed, this increase of the sensitization efficiency by increasing the chain length can partially explain the change of the luminescence quantum yield (FIG. 13a) but these changes can not only be attributed to this phenomenon. The other limitation results from the sensitization process efficiency as illustrated by the 28.4% for [Eu(H(8O2,2)-1,2-HOPO)]$^0$ vs. 40.2% for)[Eu(H(11O3,2)-1,2-HOPO)]$^0$. This results demonstrates that the change in geometry between [Eu(H(8O2,2)-1,2-HOPO)]$^0$ and [Eu(H(11O3,2)-1,2-HOPO)]$^0$ (both complexes being octa-coordinated) strongly affects the metal centered efficiency as expected and also influences the sensitization efficiency. This metal centered efficiency can be further evidenced by looking at the evolution of the radiative lifetimes as a function of the bridge length (FIG. 13b).

Furthermore, the values obtained for [Eu(H(11O3,2)-1,2-HOPO)]$^0$ are very close to the one obtained for [Eu(5LIN$^{Me}$-1,2-HOPO)$_2$]$^0$ (as the luminescence quantum yield) put forward the close symmetry of these two complexes. But, [Eu(H(14O4,2)-1,2-HOPO)]$^0$ and [Eu(H(17O5,2)-1,2-HOPO)]$^0$ evidence that [Eu(5LIN$^{Me}$-1,2-HOPO)$_2$]$^0$ is not a good model since the properties that we previously considered to be a higher limits are surpassed by the two latter octadentate complexes.

The stability of a series of complexes has been shown to be identical or even higher than the one of the benchmark DTPA allowing the use of these complexes at low concentration without apparent decomplexation.

It was also demonstrated that all the steps of the antenna effect have to be optimized and that not only the triplet excited state energy drives the sensitization process but also the efficiency of intersystem crossing has to be considered. Other factors such as the symmetry and the geometry of the ligand also need to be taken into account. In the present case, the increase of the central bridge length of octadentate ligands based on 1,2-HOPO chelator results in increased photophysical properties. This is apparent in the first instance by removing the water molecule in the inner sphere of [Eu(H(2,2-1,2-HOPO)]$^0$ and therefore, increasing the radiative decay steps relative to the non-radiative decay. In the second instance, the increase of the luminescence properties is also attributed to the changes of the geometry around the metal center. This yields some interesting luminescence properties for [Eu(H(14O4,2)-1,2-HOPO)]$^0$ and [Eu(H(17O5,2)-1,2-HOPO)]$^0$ which also have high thermodynamic stabilities in aqueous solution at pH=7.4. These properties are even better than the model compound [Eu(5LIN$^{Me}$-1,2-HOPO)$_2$]$^0$ resulting in optimized luminescence properties for an octadentate structure containing the 1,2-HOPO moiety, with a brightness that is large enough yielding complexes that may be useful for in vitro, and in cellulo biological measurements.

The articles "a," "an" and "the" as used herein do not exclude a plural number of the referent, unless context clearly dictates otherwise. The conjunction "or" is not mutually exclusive, unless context clearly dictates otherwise. The term "include" is used to refer to non-exhaustive examples.

All publications, patents, and patent applications cited herein are hereby incorporated by reference in their entirety for all purposes.

REFERENCES

1. Mathis G: HTRF(R) Technology. J Biomol Screen 1999; 4(6): 309-314.
2. Beeby A, Botchway S W, Clarkson I M, et al.: Luminescence imaging microscopy and lifetime mapping using kinetically stable lanthanide(III) complexes. J Photochem Photobiol B 2000; 57(2-3): 83-9.
3. Vereb G, Jares-Erijman E, Selvin P R, Jovin T M: Temporally and spectrally resolved imaging microscopy of lanthanide chelates. Biophys J 1998; 74(5): 2210-22.
4. Smith L M, Sanders J Z, Kaiser R J, et al.: Fluorescence detection in automated DNA sequence analysis. Nature 1986; 321(6071): 674-9.
5. Prober J M, Trainor G L, Dam R J, et al.: A system for rapid DNA sequencing with fluorescent chain-terminating dideoxynucleotides. Science 1987; 238(4825): 336-41.
6. Moore E G, Xu J, Jocher C J, Werner E J, Raymond K N: "Cymothoe sangaris": an extremely stable and highly luminescent 1,2-hydroxypyridinonate chelate of Eu(III). J Am Chem Soc 2006; 128(33): 10648-9.
7. Glazer A N: Light harvesting by phycobilisomes. Annu Rev Biophys Biophys Chem 1985; 14: 47-77.
8. Batard P, Szollosi J, Luescher I, Cerottini J C, MacDonald R, Romero P: Use of phycoerythrin and allophycocyanin for fluorescence resonance energy transfer analyzed by flow cytometry: advantages and limitations. Cytometry 2002; 48(2): 97-105.
9. Bruchez M, Jr., Moronne M, Gin P, Weiss S, Alivisatos A P: Semiconductor nanocrystals as fluorescent biological labels. Science 1998; 281(5385): 2013-6.
10. Chan W C, Nie S: Quantum dot bioconjugates for ultrasensitive nonisotopic detection. Science 1998; 281 (5385): 2016-8.
11. Mattoussi H, Mauro J M, Goldman E R, et al.: Self-assembly of CdSe—ZnS quantum dot bioconjugates using an engineered recombinant protein, Journal of the American Chemical Society 2000; 122(49): 12142-12150.
12. Tsien R Y: The green fluorescent protein. Annu Rev Biochem 1998; 67: 509-44.
13. Wang L, Xie J, Deniz A A, Schultz P G: Unnatural amino acid mutagenesis of green fluorescent protein. J. Org. Chem. 2003; 68(1): 174-6.
14. Collins F S, Green E D, Guttmacher A E, Guyer M S: A vision for the future of genomics research. Nature 2003; 422(6934): 835-47.
15. Ju J, Ruan C, Fuller C W, Glazer A N, Mathies R A: Fluorescence energy transfer dye-labeled primers for DNA sequencing and analysis. Proc Natl Acad Sci USA 1995; 92(10): 4347-51.
16. Metzker M L, Lu J, Gibbs R A: Electrophoretically uniform fluorescent dyes for automated DNA sequencing. Science 1996; 271(5254): 1420-2.
17. Lee L G, Spurgeon S L, Heiner C R, et al.: New energy transfer dyes for DNA sequencing. Nucleic Acids Res 1997; 25(14): 2816-22.
18. Brumley R L, Jr., Smith L M: Rapid DNA sequencing by horizontal ultrathin gel electrophoresis. Nucleic Acids Res 1991; 19(15): 4121-6.
19. Kheterpal I, Scherer J R, Clark S M, et al.: DNA sequencing using a four-color confocal fluorescence capillary array scanner. Electrophoresis 1996; 17(12): 1852-9.
20. Metzker M L: Emerging technologies in DNA sequencing. Genome Res 2005; 15(12): 1767-76.
21. Nunnally B K, He H, Li L C, Tucker S A, McGown L B: Characterization of visible dyes for four-decay fluorescence detection in DNA sequencing. Anal Chem 1997; 69(13): 2392-7.
22. Lieberwirth U, Arden-Jacob J, Drexhage K H, et al.: Multiplex dye DNA sequencing in capillary gel electrophoresis by diode laser-based time-resolved fluorescence detection. Anal Chem 1998; 70(22): 4771-9.
23. Lassiter S J, Stryjewski W, Legendre B L, Jr., et al.: Time-resolved fluorescence imaging of slab gels for lifetime base-calling in DNA sequencing applications. Anal Chem 2000; 72(21): 5373-82.
24. Alayerdian L, Alayerdian S, Bilenko O, et al.: A family of novel DNA sequencing instruments based on single-photon detection. Electrophoresis 2002; 23(16): 2804-17.
25. Kling J: Ultrafast DNA sequencing. Nat Biotechnol 2003; 21(12): 1425-7.
26. Selvin P R: Principles and biophysical applications of lanthanide-based probes. Annu Rev Biophys Biomol Struct 2002; 31: 275-302.
27. Petoud S, Cohen S M, Bunzli J C, Raymond K N: Stable lanthanide luminescence agents highly emissive in aqueous solution: multidentate 2-hydroxyisophthalamide complexes of Sm(3+), Eu(3+), Tb(3+), Dy(3+). J Am Chem Soc 2003; 125(44): 13324-5.
28. Hemmila I, Dakubu S, Mukkala V M, Siitari H, Lovgren T: Europium as a label in time-resolved immunofluorometric assays. Anal Biochem 1984; 137(2): 335-43.
29. Allicotti G, Borras E, Pinilla C: A time-resolved fluorescence immunoassay (DELFIA) increases the sensitivity of antigen-driven cytokine detection. J Immunoassay Immunochem 2003; 24(4): 345-58.
30. Schoket B, Doty W A, Vincze I, et al.: Increased sensitivity for determination of polycyclic aromatic hydrocarbon-DNA adducts in human DNA samples by dissociation-enhanced lanthanide fluoroimmunoassay (DELFIA). Cancer Epidemiol Biomarkers Prev 1993; 2(4): 349-53.
31. Poole R A, Bobba G, Cann M J, Frias J C, Parker D, Peacock R D: Synthesis and characterisation of highly emissive and kinetically stable lanthanide complexes suitable for usage "in cellulo". Org Biomol Chem 2005; 3(6): 1013-24.
32. Comby S, Imbert D, Chauvin A S, Bunzli J C: Stable 8-hydroxyquinolinate-based podates as efficient sensitizers of lanthanide near-infrared luminescence. Inorg Chem 2006; 45(2): 732-43.
33. Jaakkola L, Peuralahti J, Hakala H, et al.: Solid-phase synthesis of oligonucleotides labeled with luminescent lanthanide(III) chelates. Bioconjug Chem 2005; 16(3): 700-9.
34. Weibel N, Charbonniere L J, Guardigli M, Roda A, Ziessel R: Engineering of highly luminescent lanthanide tags suitable for protein labeling and time-resolved luminescence imaging. J Am Chem Soc 2004; 126(15): 4888-96.
35. Chen J, Selvin P R: Thiol-reactive luminescent chelates of terbium and europium. Bioconjug Chem 1999; 10(2): 311-5.
36. Doble D M, Melchior M, O'Sullivan B, et al.: Toward optimized high-relaxivity MRI agents: the effect of ligand basicity on the thermodynamic stability of hexadentate hydroxypyridonate/catecholate gadolinium(III) complexes. Inorg Chem 2003; 42(16): 4930-7.
37. Mathis G: Rare earth cryptates and homogeneous fluoroimmunoassays with human sera. Clin Chem 1993; 39(9): 1953-9.
38. Brunet E, Juanes O, Sedano R, Rodriguez-Ubis J C: Lanthanide complexes of polycarboxylate-bearing dipyrazolylpyridine ligands with near-unity luminescence quantum yields: the effect of pyridine substitution. Photochem Photobiol Sci 2002; 1(8): 613-8.
39. Alpha B, Balzani V, Lehn J M, Perathoner S, Sabbatini N: Quantitative photophysical results of luminescence studies: Eu3+ and Tb3+ cryptates of macrobicyclic polypyridine ligands. Angewandte Chemie, International Edition 1987; 26: 1266.
40. Hemmila I: Luminescent Lanthanide Chelates—a Way to More Sensitive Diagnostic Methods. Journal of Alloys and Compounds 1995; 225(1-2): 480-485.
41. Selvin P R, Hearst J E: Luminescence energy transfer using a terbium chelate: improvements on fluorescence energy transfer. Proc Natl Acad Sci USA 1994; 91(21): 10024-8.
42. Takalo H, Mukkala V M, Mikola H, Liitti P, Hemmila I: Synthesis of europium(III) chelates suitable for labeling of bioactive molecules. Bioconjug Chem 1994; 5(3): 278-82.
43. Hemmila I: LANCE: homogeneous assay platform for HTS. Journal of Biomolecular Screening 1999; 4(6): 303-307.

44. Mikola H, Takalo H, Hemmila I: Syntheses and properties of luminescent lanthanide chelate labels and labeled haptenic antigens for homogeneous immunoassays. Bioconjug Chem 1995; 6(3): 235-41.
45. Hemmila Iowa: Immunochem. 1997: 193-214.
46. Allicotti G, Borras E, Pinilla C J: Immunoassay Immunochem. 2003; 24: 345-358.
47. Moore E G, Jocher C J, Xu J, Werner E J, Raymond K N: An octadentate luminescent Eu(III) 1,2-HOPO chelate with potent aqueous stability. Inorg Chem 2007; 46(14): 5468-70.
48. Clarke E T, Martell A E, Reibenspies J: Crystal structure of the tris 1,2-dimethyl-3-hydroxy-4-pyridinone (DMHP) complex with the Fe (III) ion. Inorganica chimica acta 1992; 196(177-183).
49. Li Y J, Martell A E: Potentiometric and spectrophotometric determination of stabilities of the 1-hydroxy-2-pyridinone complexes of trivalent and divalent metal ions. Inorganica chimica acta 1993; 214: 103-111.
50. Farkas E, Kozman E, Petho M, Herlihy K M, Micera G: Equilibrium studies on copper(II)- and iron(III)-monohydroxamates. Polyhedron 1998; 17: 3331-3342.
51. Xu J, Churchill D G, Botta M, Raymond K N: Gadolinium(III) 1,2-hydroxypyridonate-based complexes: toward MRI contrast agents of high relaxivity. Inorg Chem 2004; 43(18): 5492-4.
52. Hermansen G: Bioconjugate techniques: Academic Press, 1996.
53. Demas J N, Crosby G A: The measurement of photoluminescence quantum yields. Journal Phys. Chem. 1971; 75: 991-1024.
54. Mugabe C, Azghani A, Omri A: Liposome-mediated gentamicin delivery: development and activity against resistant strains of Pseudomonas aeruginosa isolated from cystic fibrosis patients. J Antimicrob Chemother 2005; 55(2): 269-271.
55. Pierre V C, Botta M, Aime S, Raymond K N: Substituent effects on Gd(III)-based MRI contrast agents: optimizing the stability and selectivity of the complex and the number of coordinated water molecules. Inorg Chem 2006; 45(20): 8355-64.

What is claimed is:

1. A compound having a structure according to Formula II:

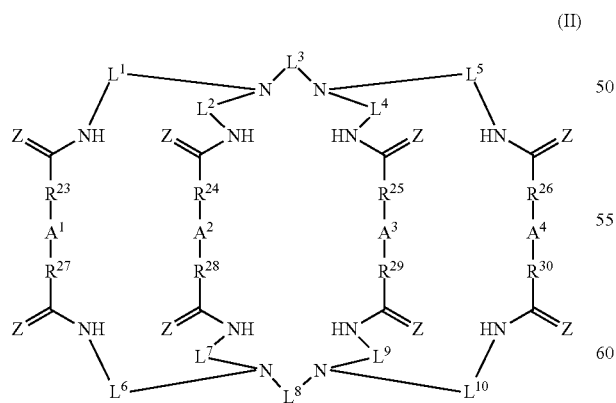

wherein each Z is independently selected from O and S;
L$^3$ comprises —(CH$_2$CH$_2$O)$_m$R$^{31}$— and L$^8$ comprises —(CH$_2$CH$_2$O)$_n$R$^{32}$— wherein m and n are integers independently selected from 0, 1, 2, 3, 4, 5, 6, 7, 8 and 9;

A$^1$, A$^2$, A$^3$, A$^4$, L$^1$, L$^2$, L$^4$, L$^5$, L$^6$, L$^7$, L$^9$, L$^{10}$, R$^{31}$ and R$^{32}$ are independently selected from substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

R$^{23}$, R$^{24}$, R$^{25}$, R$^{26}$, R$^{27}$, R$^{28}$, R$^{29}$ and R$^{30}$ are independently selected from a bond, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

at least one of A$^1$, A$^2$, A$^3$ and A$^4$ is selected from

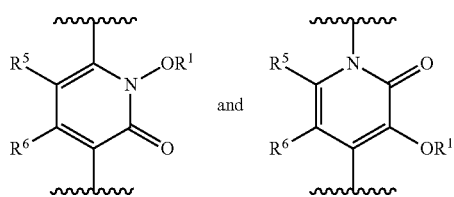

wherein each R$^1$ is independently selected from H, an enzymatically labile group, a hydrolytically labile group, a metabolically labile group, a photolytic group and a single negative charge;

each R$^5$ and R$^6$ is independently selected from H, substituted or unsubstituted alkyl, substituted or unsubstituted heteroalkyl, halogen, CN, CF$_3$, acyl, —SO$_2$NR$^{17}$R$^{18}$, —NR$^{17}$R$^{18}$, —OR$^{17}$, —S(O)$_2$R$^{17}$, —COOR$^{17}$, —S(O)$_2$OR$^{17}$, —OC(O)R$^{17}$, —C(O)NR$^{17}$R$^{18}$, —NR$^{17}$C(O)R$^{18}$, —NR$^{17}$SO$_2$R$^{18}$, and —NO$_2$, R$^5$ and R$^6$ are optionally joined to form a ring system which is a member selected from substituted or unsubstituted cycloalkyl, substituted or unsubstituted heterocycloalkyl, substituted or unsubstituted aryl and substituted or unsubstituted heteroaryl; and R$^{17}$ and R$^{18}$ are independently selected from H, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl;

R$^{17}$ and R$^{18}$, together with the atoms to which they are attached, are optionally joined to form a 5- to 7-membered ring.

2. A complex formed between at least one metal ion and the compound of claim 1.

3. A method of detecting an analyte in a sample, said method comprising:
(a) contacting said analyte with a solid support comprising the complex of claim 2, wherein said analyte forms an analyte complex;
(b) exciting said complex such that said complex transfers excitation energy to said analyte complex; and
(c) detecting energy emitted by said analyte complex, thereby detecting said analyte.

4. The compound of claim 1, wherein $A^1$, $A^2$, $A^3$ and $A^4$ are independently selected from

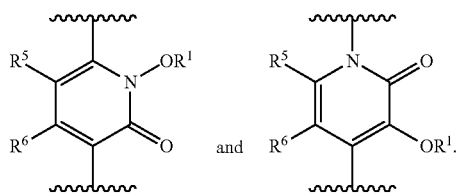

5. The compound of claim 1, wherein $A^1$, $A^2$, $A^3$ and $A^4$ have the same relative orientation; and (a) $A^1$, $A^2$, $A^3$ and $A^4$ are each independently

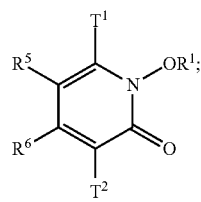

or (b) $A^1$, $A^2$, $A^3$ and $A^4$ are each independently

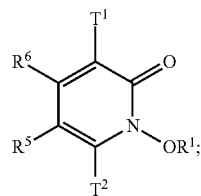

or (c) $A^1$, $A^2$, $A^3$ and $A^4$ are each independently

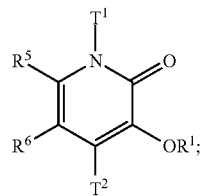

or (d) $A^1$, $A^2$, $A^3$ and $A^4$ are each independently

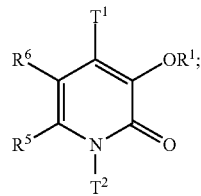

wherein $T^1$ is a bond to a linker having the structure:

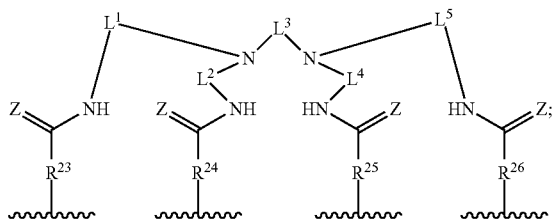

and $T^2$ is a bond to a linker having the structure:

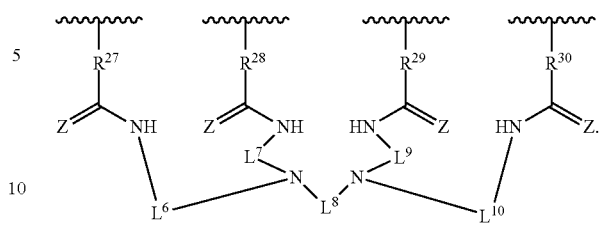

6. The compound of claim 1, wherein Z is O.

7. The compound of claim 1, wherein $R^5$, $R^6$ or both are H.

8. The compound of claim 1, wherein $R^1$ is H or a negative charge.

9. The compound of claim 1, wherein $R^{23}$, $R^{24}$, $R^{25}$, $R^{26}$, $R^{27}$, $R^{28}$, $R^{29}$ and $R^{30}$ are independently selected from a bond, substituted or unsubstituted alkyl, substituted or unsubstituted heteroalkyl.

10. The compound of claim 9, wherein $R^{23}$, $R^{24}$, $R^{25}$ and $R^{26}$ are a bond.

11. The compound of claim 9, wherein $R^{27}$, $R^{28}$, $R^{29}$, and $R^{30}$ are unsubstituted alkyl.

12. The compound of claim 11, wherein $R^{27}$, $R^{28}$, $R^{29}$ and $R^{30}$ are methyl.

13. The compound of claim 1, wherein m, n or both are an integer independently selected from 1, 2, 3, 4, 5, 6, 7, 8 and 9.

14. The compound of claim 1, wherein at least one of $L^1$, $L^2$, $L^3$, $L^4$, $L^5$, $L^6$, $L^7$, $L^8$, $L^9$ and $L^{10}$ comprises a cleavable group or an activatable group.

15. The compound of claim 1, wherein $L^3$, $L^8$ or both are independently substituted or unsubstituted heteroalkyl.

16. The compound of claim 1, wherein $L^1$, $L^2$, $L^4$, $L^5$, $L^6$, $L^7$, $L^9$, $L^{10}$, $R^{31}$ and $R^{32}$ are independently selected from substituted or unsubstituted $C_1$ to $C_6$ alkyl.

17. The compound of claim 16, wherein $L^1$, $L^2$, $L^4$, $L^5$, $L^6$, $L^7$, $L^9$, $L^{10}$, $R^{31}$ and $R^{32}$ are independently selected from substituted or unsubstituted ethyl.

18. The compound of claim 1, wherein at least one of $L^1$, $L^2$, $L^3$, $L^4$, $L^5$, $L^6$, $L^7$, $L^8$, $L^9$, $L^{10}$, is substituted by -$L^{11}$-X, wherein L is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl; and X is a functional moiety.

19. The compound of claim 18, wherein one or more groups selected from $L^1$, $L^2$, $L^3$, $L^4$, $L^5$, $L^6$, $L^7$, $L^8$, $L^9$ and $L^{10}$ is ethyl substituted by -$L^{11}$-X and each of the unselected groups is unsubstituted ethyl.

20. The compound of claim 18, wherein $L^3$, $L^8$ or both are independently substituted by -$L^{11}$-X.

21. The compound of claim 18, wherein $L^{11}$ is selected from substituted or unsubstituted alkyl and substituted or unsubstituted heteroalkyl.

22. The compound of claim 18, wherein X is selected from —$NH_2$ and —C(O)OH.

23. The compound of claim 18, wherein -$L^{11}$-X is selected from

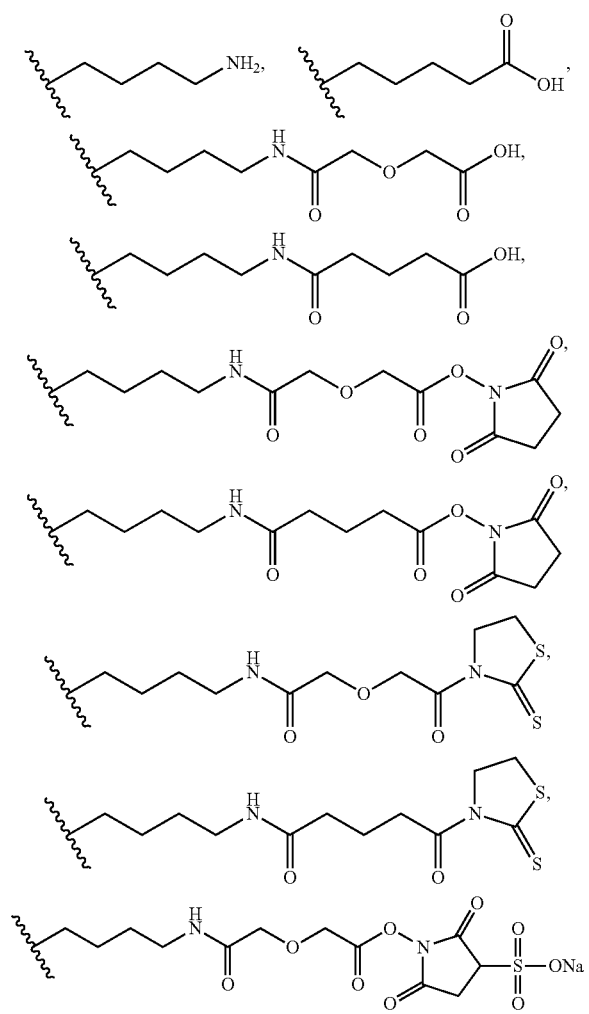
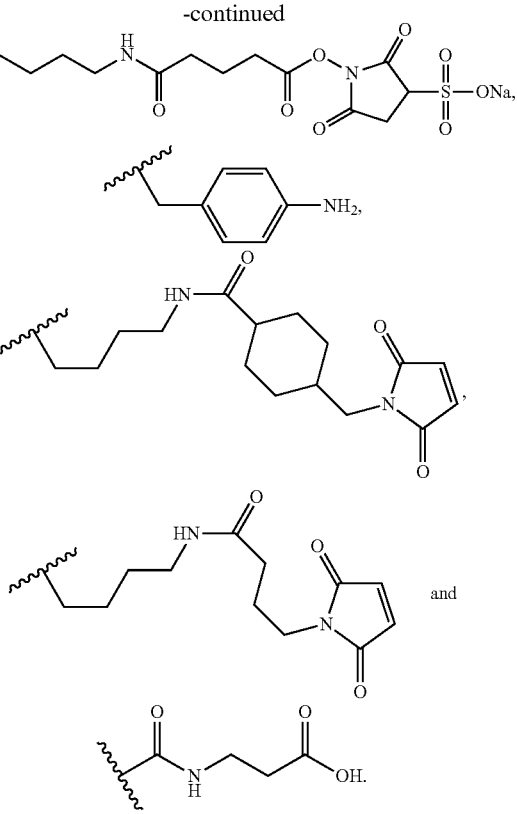
24. The compound of claim 18, wherein X comprises a linkage to a species selected from a fluorophore, a carrier moiety and a solid support.
25. The compound of claim 18, wherein $L^3$ is selected from $-(CH_2CH_2O)_3(CH_2)_2-$, $-(CH_2CH_2O)_4(CH_2)_2-$ and $-(CH_2CH_2O)_5(CH_2)_2-$, wherein any H is optionally replaced by $-L^{11}-X$.
26. The compound of claim 1, having a structure selected from:
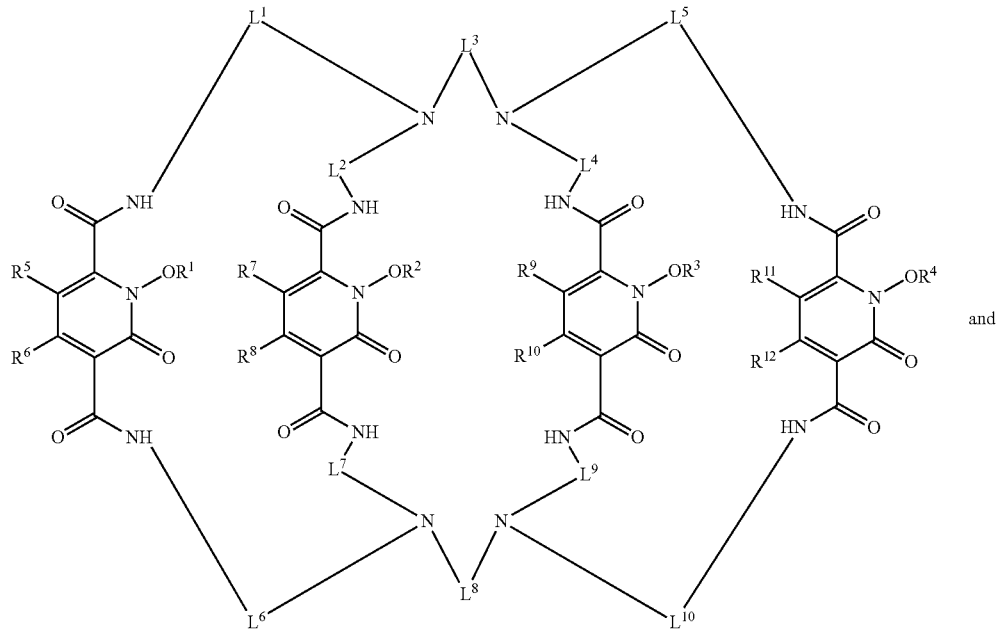

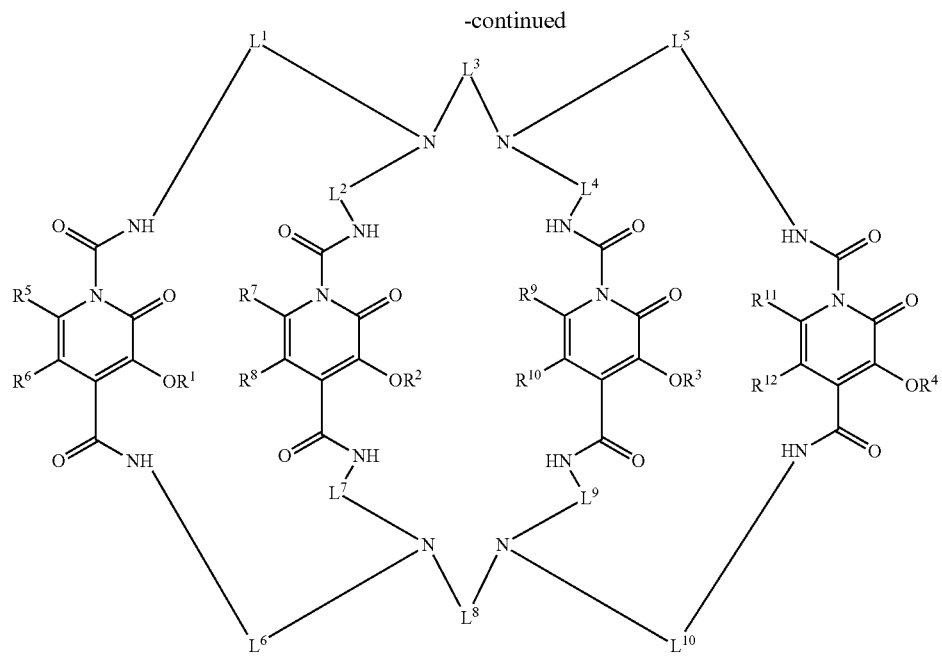

wherein $R^1$, $R^2$, $R^3$ and $R^4$ are members independently selected from H, an enzymatically labile group, a hydrolyticany labile group, a metabolically labile group, a photolytic group and a single negative charge; and $R^5$, $R^6$, $R^7$, $R^8$, $R^9$, $R^{10}$, $R^{11}$ and $R^{12}$ are members independently selected from H, substituted or unsubstituted alkyl, substituted or unsubstituted heteroalkyl, halogen, CN, $CF_3$, acyl, $-SO_2NR^{17}R^{18}$, $-NR^{17}R^{18}$, $-OR^{17}$, $-S(O)_2R^{17}$, $-COOR^{17}$, $-S(O)_2OR^{17}$, $-OC(O)R^{17}$, $-C(O)NR^{17}R^{18}$, $-NR^{17}C(O)R^{18}$, $-NR^{17}SO_2R^{18}$, and $-NO_2$, wherein each of pairs $R^7$ and $R^8$, $R^9$ and $R^{10}$, and $R^{11}$ and $R^{12}$ is optionally joined to form a ring system. which is a member selected from substituted or unsubstituted cycloalkyl, substituted or unsubstituted heterocycioalkyl, substituted or unsubstituted aryl and substituted or unsubstituted heteroaryl; and $R^{17}$ and $R^{18}$ are members independently selected from H, substituted or unsubstituted alkyl, substituted or unsubstituted heteroalkyl, substituted or unsubstituted cycloalkyl, substituted or unstibstituted heterocycloalkyl, substituted or unstibstituted aryl and substituted or unsubstituted heteroaryk and $R^{17}$ and $R^{18}$, together with the atoms to which they are attached, are optionally joined to form a 5- to 7-membered ring.

27. The compound of claim 26, having a structure that is selected from:

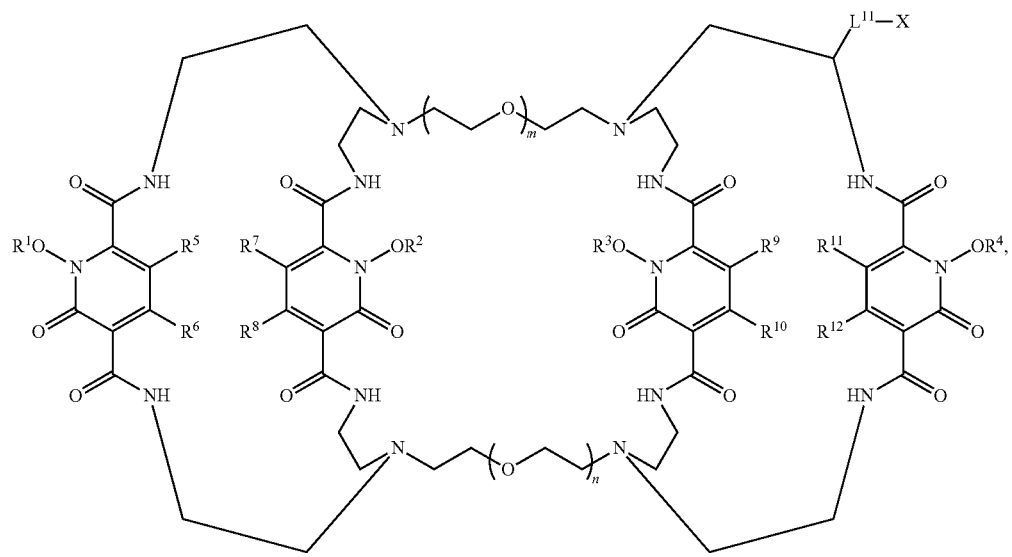

-continued
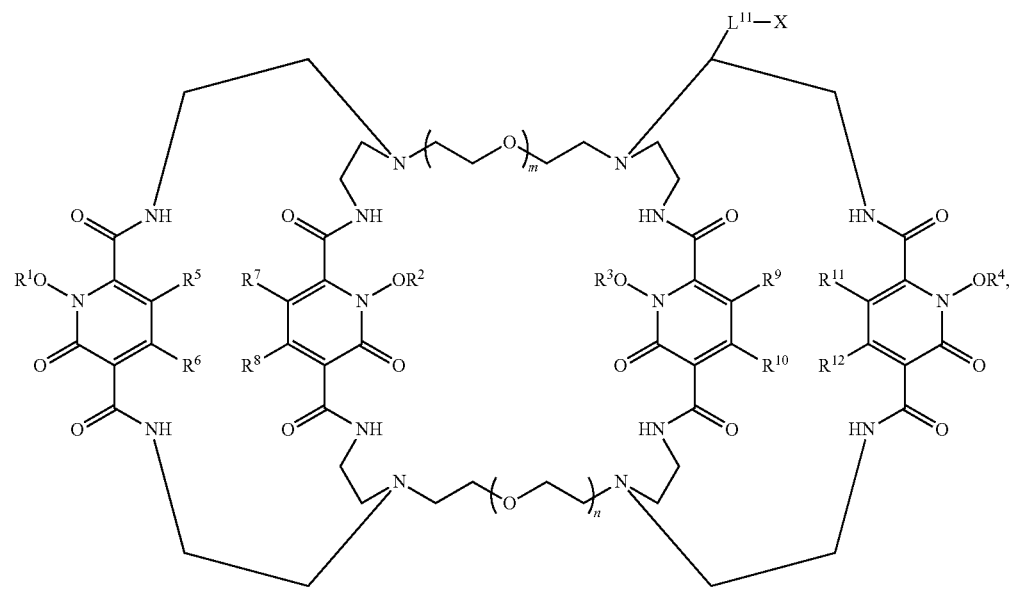
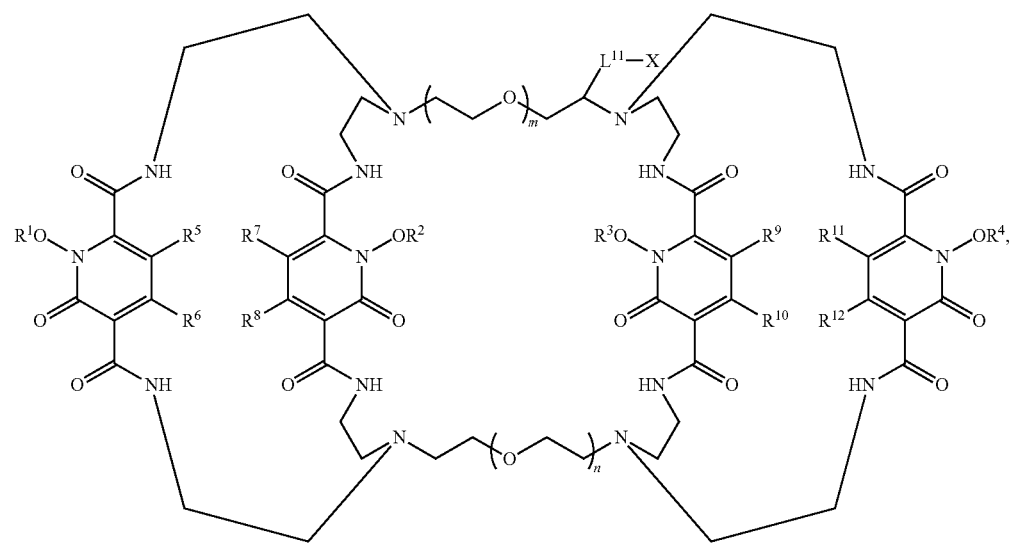
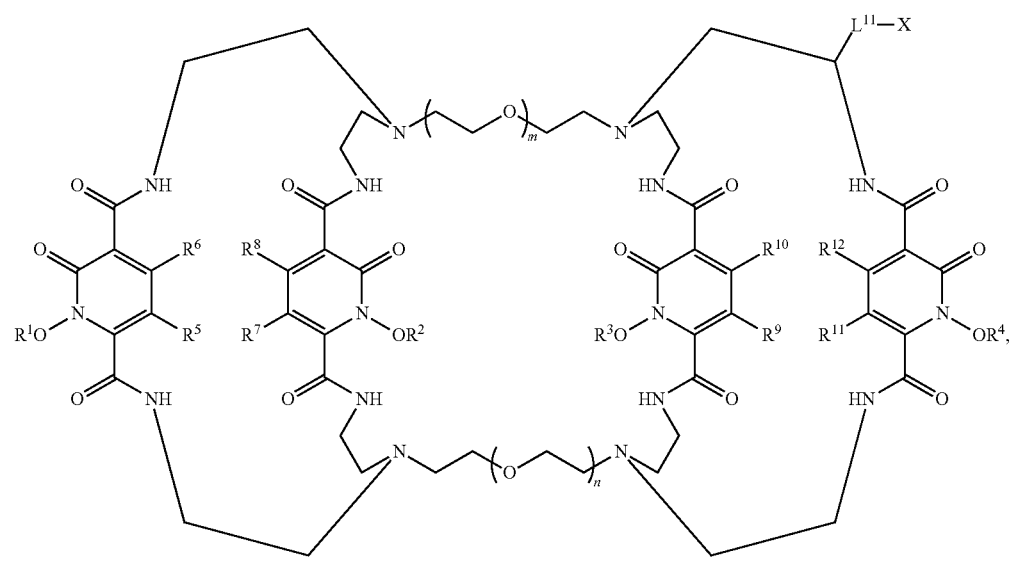

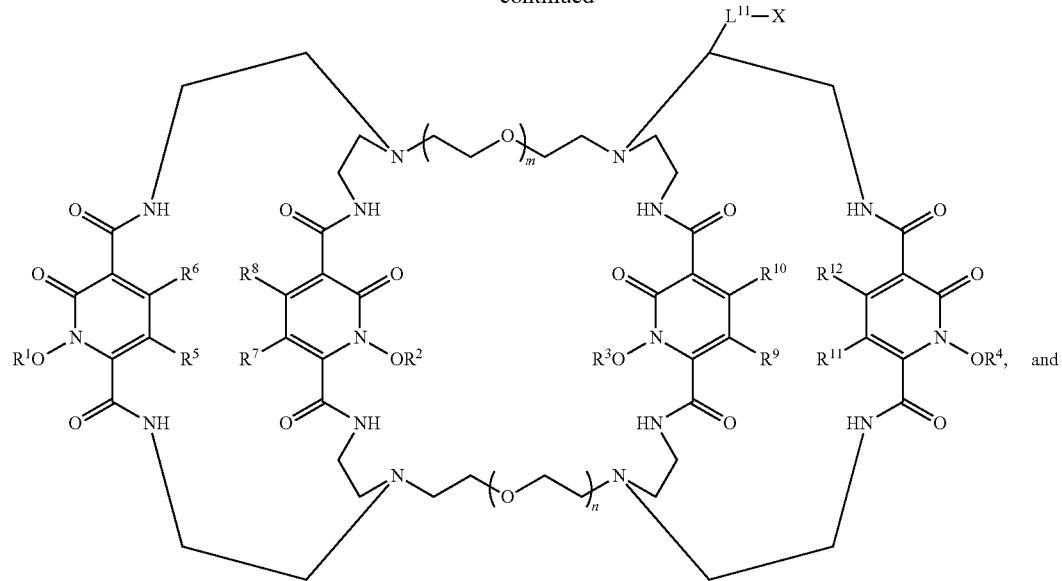

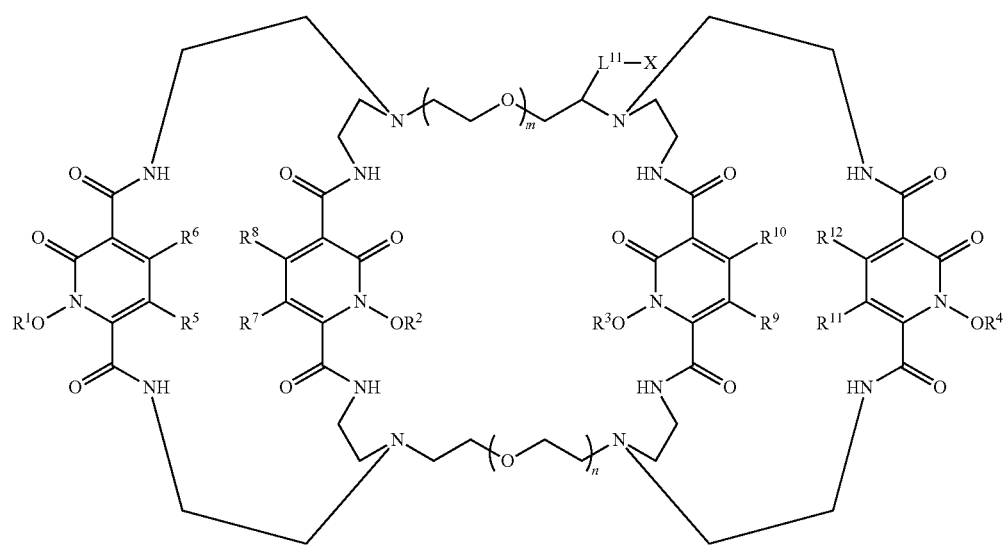

wherein m and n are integers independently selected from 0, 1, 2, 3, 4, 5, 6, 7, 8 and 9 and wherein at least one of m and n is not 0;

L is selected from a bond, acyl, substituted or unsubstituted alkyl, substituted or unsubstituted heteroalkyl, substituted or unsubstituted cycloalkyl, substituted or unsubstituted heterocycloalkyl, substituted or unsubstituted an and substituted or unsubstituted heteroaryl; and X is a functional moiety.

28. The compound of claim 27, wherein $R^1$, $R^2$, $R^3$, and $R^4$ are H or a single negative charge; and $R^5$, $R^6$, $R^7$, $R^8$, $R^9$, $R^{10}$, $R^{11}$ and $R^{12}$ are H.

29. The compound of claim 1, having the structure:
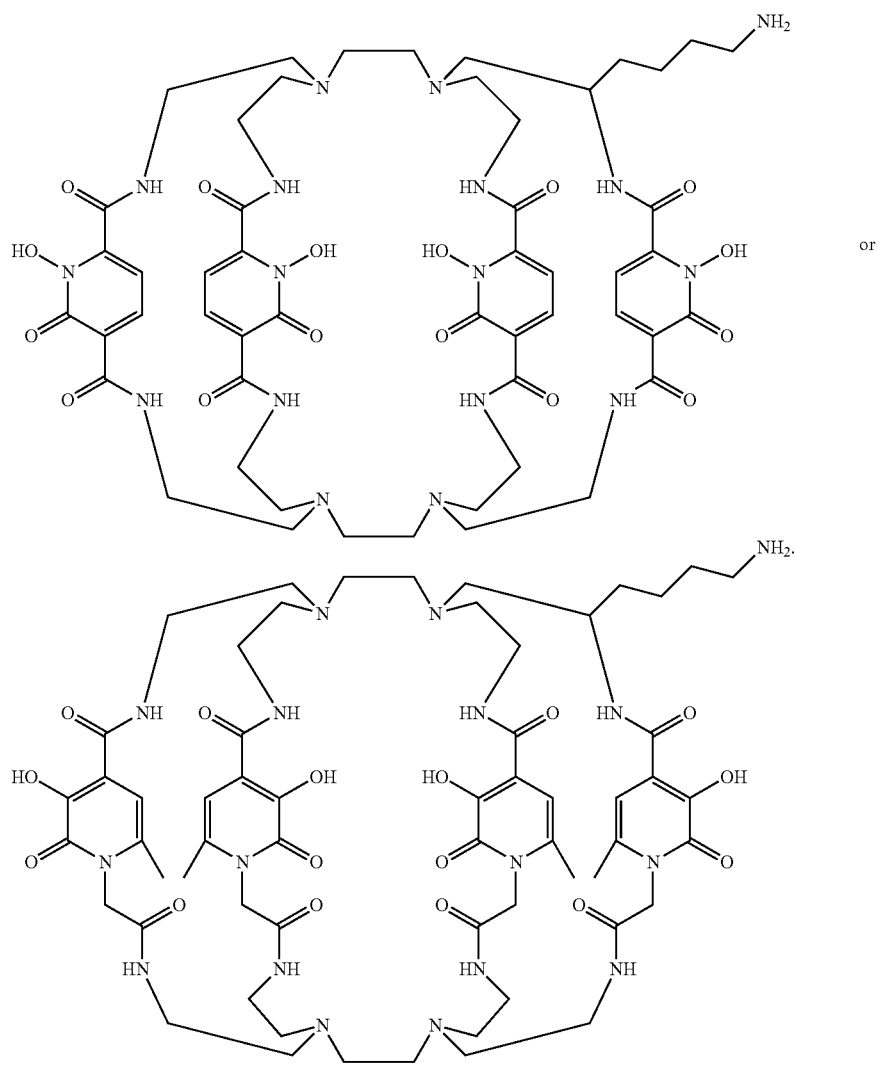
or
30. The complex of claim 2, wherein said metal ion is a lanthanide ion.
31. The complex of claim 30, wherein the lanthanide is a member selected from neodymium (Nd), samarium (Sm), europium (Eu), gadolinium (Gd), terbium (Tb), dysprosium (Dy) and ytterbium (Yb).
* * * * *